United States Patent
Beckman et al.

(10) Patent No.: US 11,832,903 B2
(45) Date of Patent: *Dec. 5, 2023

(54) ROBOTIC SURGICAL TOOL WITH REPLACEABLE CARRIAGE

(71) Applicant: Cilag GmbH International, Zug (CH)

(72) Inventors: Andrew T. Beckman, Cincinnati, OH (US); Charles J. Scheib, Loveland, OH (US)

(73) Assignee: Cilag GmbH International, Zug (CH)

( * ) Notice: Subject to any disclaimer, the term of this patent is extended or adjusted under 35 U.S.C. 154(b) by 605 days.

This patent is subject to a terminal disclaimer.

(21) Appl. No.: 16/936,809

(22) Filed: Jul. 23, 2020

(65) Prior Publication Data

US 2022/0022975 A1    Jan. 27, 2022

(51) Int. Cl.

| | |
|---|---|
| A61B 34/30 | (2016.01) |
| B25J 5/00 | (2006.01) |
| B25J 5/02 | (2006.01) |
| B25J 15/04 | (2006.01) |
| B25J 9/10 | (2006.01) |

(52) U.S. Cl.
CPC ............... *A61B 34/30* (2016.02); *B25J 5/007* (2013.01); *B25J 5/02* (2013.01); *B25J 9/1035* (2013.01); *B25J 15/045* (2013.01); *A61B 2034/301* (2016.02); *A61B 2034/302* (2016.02); *B25J 9/1025* (2013.01)

(58) Field of Classification Search
CPC .............. A61B 34/30; A61B 2034/301; A61B 2034/302; B25J 5/007; B25J 5/02; B25J 9/1025; B25J 9/1035; B25J 15/045
See application file for complete search history.

(56) References Cited

U.S. PATENT DOCUMENTS

| | | |
|---|---|---|
| 2011/0040150 A1 | 2/2011 | Govari et al. |
| 2019/0192129 A1 | 6/2019 | Xu et al. |

(Continued)

FOREIGN PATENT DOCUMENTS

| | | | |
|---|---|---|---|
| CN | 108742848 A | 11/2018 | |
| WO | 2019191396 A1 | 10/2019 | |
| WO | WO-2019191420 A1 * | 10/2019 | ....... A61B 17/00234 |

OTHER PUBLICATIONS

ISR-WO for related matter PCT/IB2021/056552 dated Dec. 9, 2021.

*Primary Examiner* — Pamela M. Bays
*Assistant Examiner* — Megan T Fedorky
(74) *Attorney, Agent, or Firm* — Vorys, Sater, Seymour, and Pease LLP

(57) ABSTRACT

A method of assembling a robotic surgical tool includes providing a handle having first and second ends, a lead screw, and a spline extendable between the first and second ends. The lead screw is rotated in a first direction to translate an elevator layer of a carriage proximally along a longitudinal axis of the handle, the elevator layer being movably mounted to the lead screw at a carriage nut. One or more additional layers of the carriage are removably coupled to the elevator layer and an elongate shaft extends distally from the additional layers, and an end effector is arranged at a distal end of the shaft. The elevator layer is penetrated by the end effector and the shaft upon coupling the additional layers to the elevator layer, and the lead screw is rotated in a second direction opposite the first direction to translate the carriage distally.

16 Claims, 44 Drawing Sheets

(56) References Cited

U.S. PATENT DOCUMENTS

2019/0298464 A1* 10/2019 Abbott .................. A61B 34/70
2021/0015572 A1  1/2021 Gomez et al.
2021/0022815 A1* 1/2021 Abbott .................. A61B 34/71

* cited by examiner

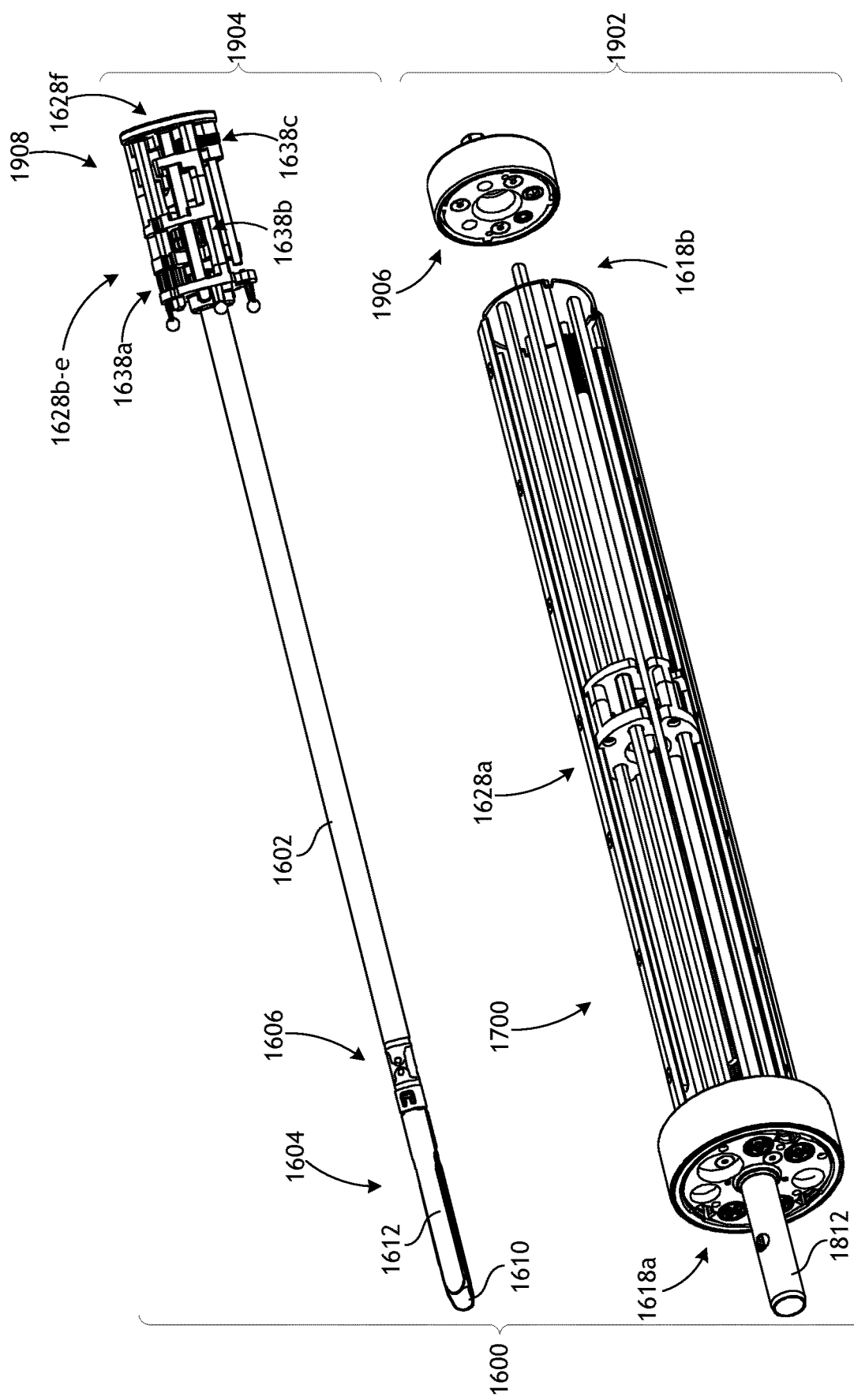

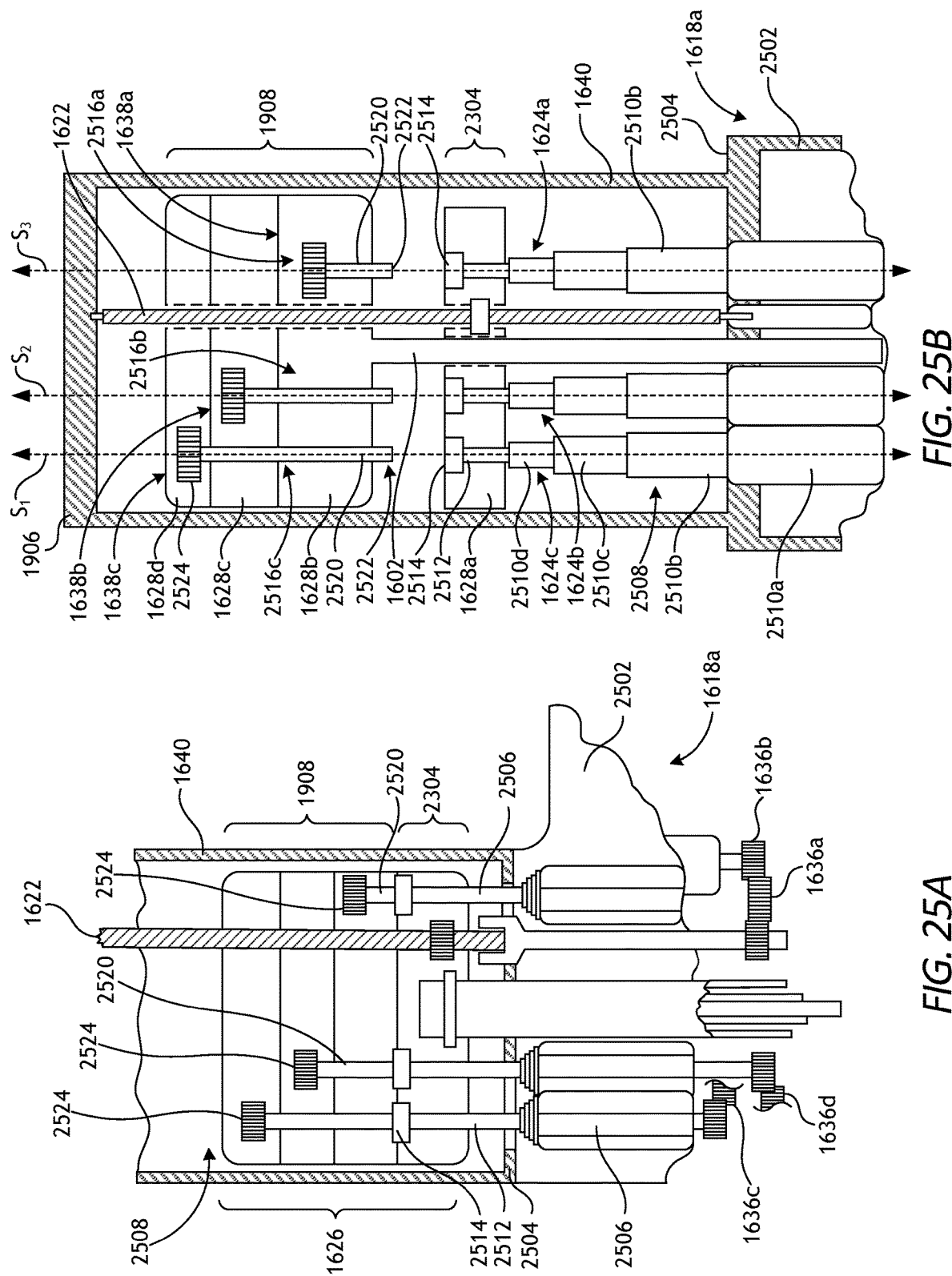

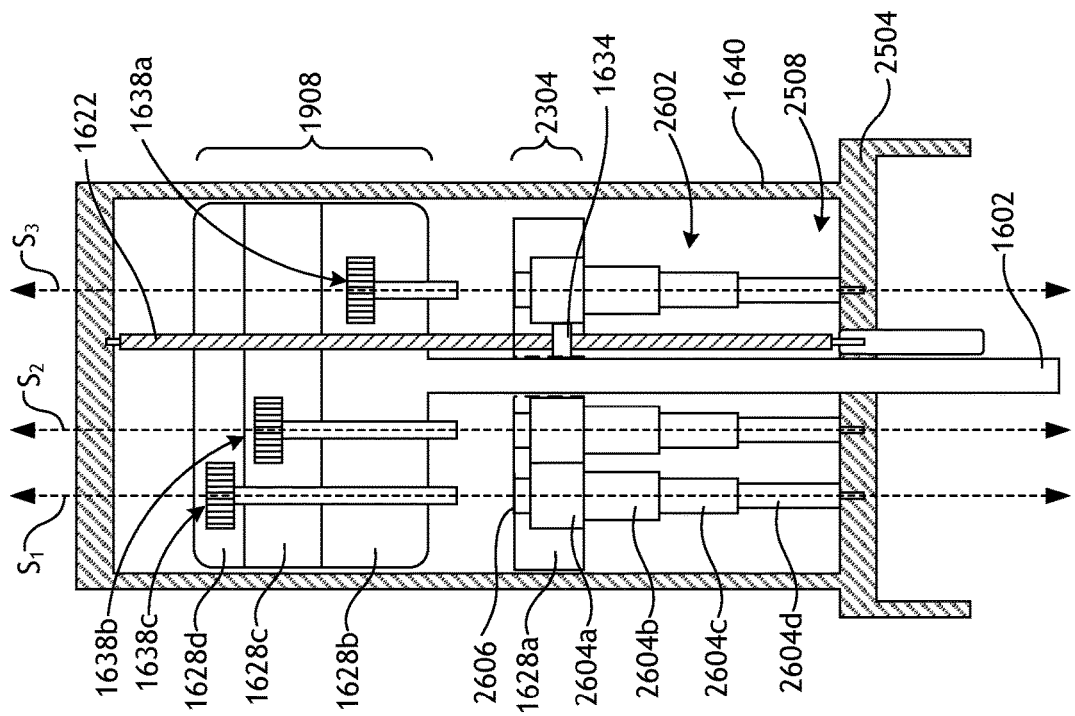
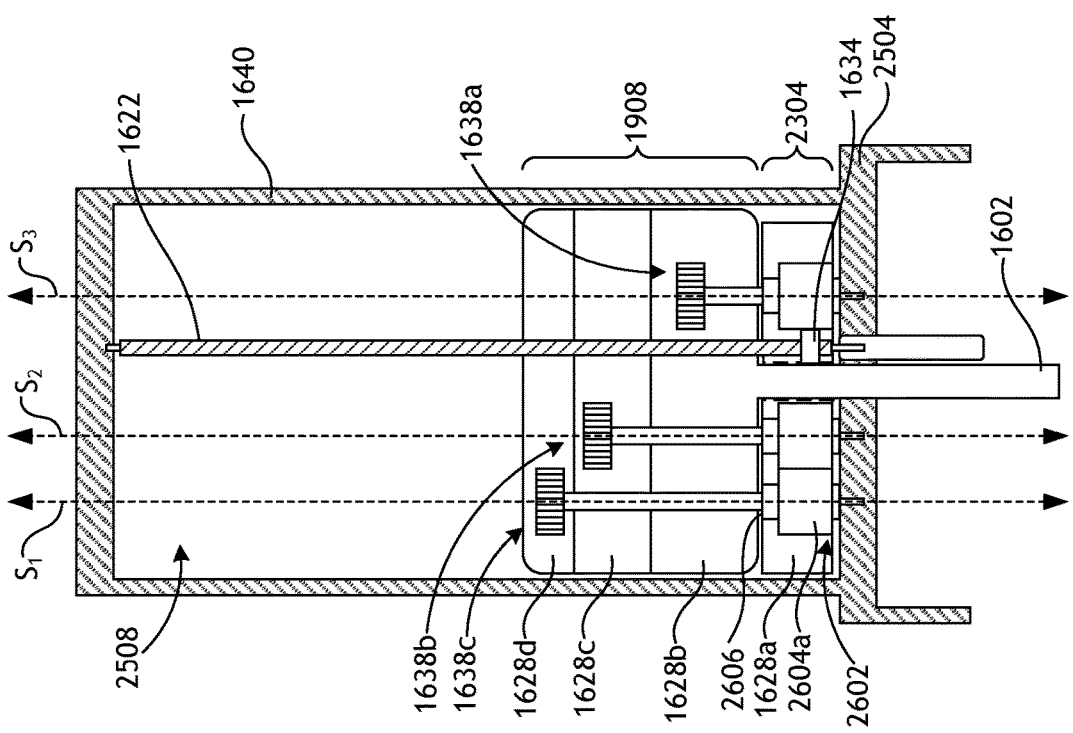

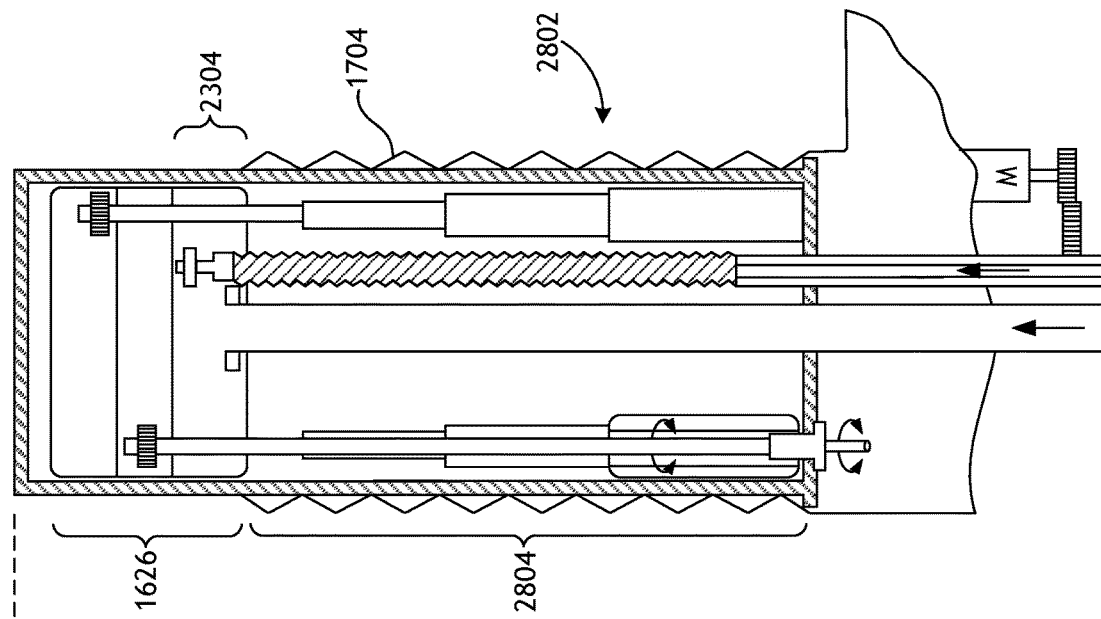
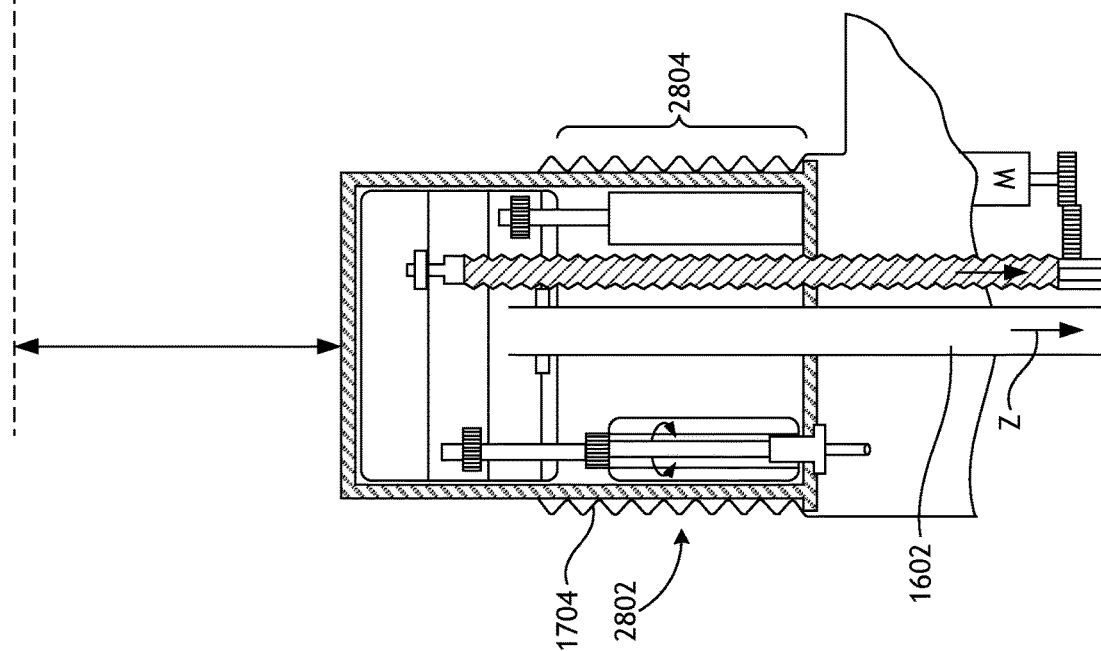
FIG. 28A
FIG. 28B

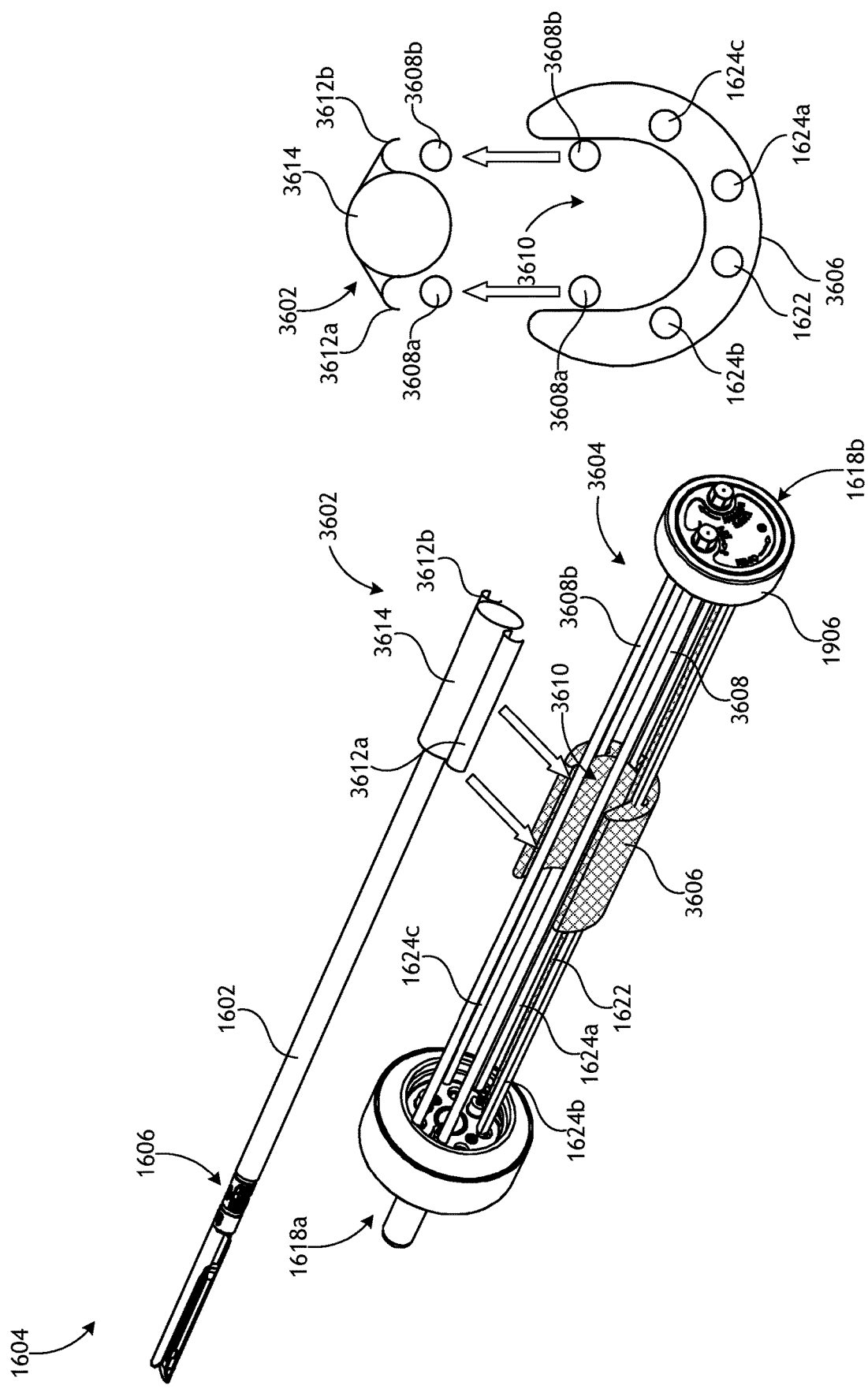

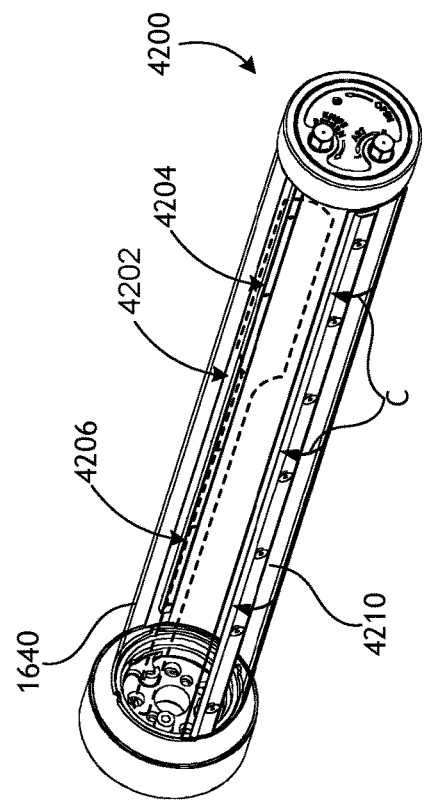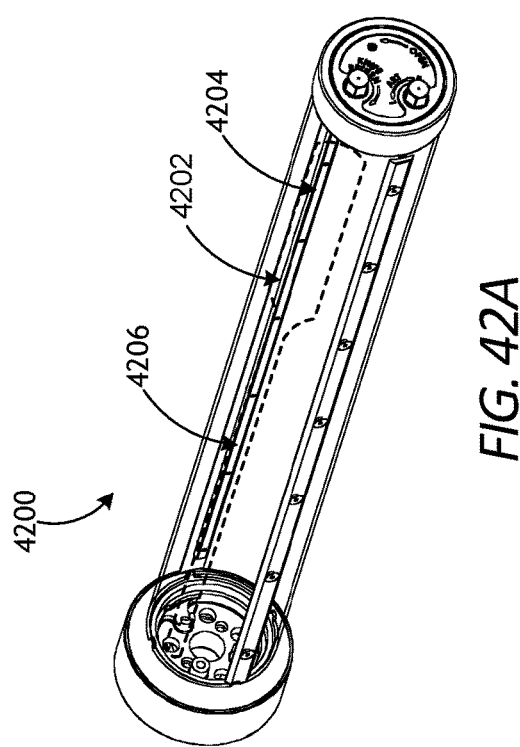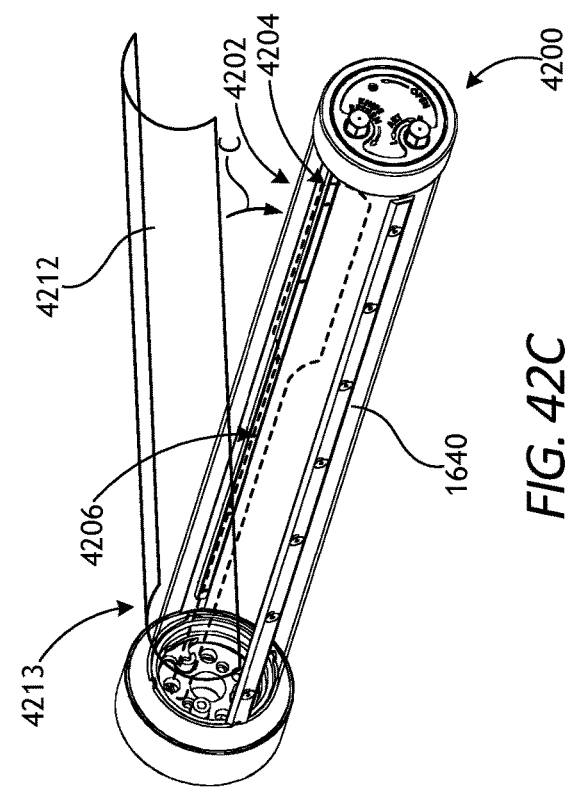

ROBOTIC SURGICAL TOOL WITH REPLACEABLE CARRIAGE

TECHNICAL FIELD

The systems and methods disclosed herein are directed to surgical tools and, more particularly to, a robotic surgical tool having a stage portion and an instrument portion removably secured to the stage portion.

BACKGROUND

Minimally invasive surgical (MIS) instruments are often preferred over traditional open surgical devices due to the reduced post-operative recovery time and minimal scarring. The most common MIS procedure may be endoscopy, and the most common form of endoscopy is laparoscopy, in which one or more small incisions are formed in the abdomen of a patient and a trocar is inserted through the incision to form a pathway that provides access to the abdominal cavity. The cannula and sealing system of the trocar is used to introduce various instruments and tools into the abdominal cavity, as well as to provide insufflation to elevate the abdominal wall above the organs. The instruments can be used to engage and/or treat tissue in a number of ways to achieve a diagnostic or therapeutic effect.

Each surgical tool typically includes an end effector arranged at its distal end. Example end effectors include clamps, graspers, scissors, staplers, suction irrigators, blades (i.e., RF), and needle holders, and are similar to those used in conventional (open) surgery except that the end effector of each tool is separated from its handle by an approximately 12-inch long shaft. A camera or image capture device, such as an endoscope, is also commonly introduced into the abdominal cavity to enable the surgeon to view the surgical field and the operation of the end effectors during operation. The surgeon is able to view the procedure in real-time by means of a visual display in communication with the image capture device.

Various robotic systems have recently been developed to assist in MIS procedures. Robotic systems can allow for more intuitive hand movements by maintaining natural eye-hand axis. Robotic systems can also allow for more degrees of freedom in movement by including a "wrist" joint that creates a more natural hand-like articulation and allows for access to hard to reach spaces. The instrument's end effector can be articulated (moved) using motors and actuators forming part of a computerized motion system. A user (e.g., a surgeon) is able to remotely operate an instrument's end effector by grasping and manipulating in space one or more controllers that communicate with an instrument driver coupled to the surgical instrument. User inputs are processed by a computer system incorporated into the robotic surgical system and the instrument driver responds by actuating the motors and actuators of the motion system. Moving the drive cables and/or other mechanical mechanisms manipulates the end effector to desired positions and configurations.

Improvements to robotically-enabled medical systems will provide physicians with the ability to perform endoscopic and laparoscopic procedures more effectively and with improved ease.

SUMMARY OF DISCLOSURE

Various details of the present disclosure are hereinafter summarized to provide a basic understanding. This summary is not an extensive overview of the disclosure and is neither intended to identify certain elements of the disclosure, nor to delineate the scope thereof. Rather, the primary purpose of this summary is to present some concepts of the disclosure in a simplified form prior to the more detailed description that is presented hereinafter.

Embodiments disclosed herein include a method of assembling a surgical tool. The method includes providing a handle having a first end, a second end, and a lead screw and at least one spline extendable between the first and second ends. The method may further include rotating the lead screw in a first direction and thereby translating an elevator layer of a carriage proximally along a longitudinal axis of the handle, wherein the elevator layer is movably mounted to the lead screw at a carriage nut, removably coupling one or more additional layers of the carriage to the elevator layer, wherein an elongate shaft extends distally from the one or more additional layers and an end effector is arranged at a distal end of the elongate shaft, penetrating the elevator layer with the end effector and the elongate shaft upon coupling the one or more additional layers to the elevator layer, and rotating the lead screw in a second direction opposite the first direction and thereby translating the carriage distally along the longitudinal axis. In a further embodiment, the method also includes coupling a cap to the second end. In another further embodiment, the step of coupling the cap to the second end further includes receiving an end of the at least one spline in at least one spline coupling provided on the cap upon coupling the cap to the second end, and receiving an end of the lead screw in a stage coupling provided on the cap upon coupling the cap to the second end. In another further embodiment, a drive gear and an activating mechanism are housed in the carriage and operatively coupled together such that rotation of the drive gear correspondingly actuates the activating mechanism, and the method further includes inserting the at least one spline through the drive gear and thereby operatively coupling the drive gear to the at least one spline such that the drive gear is rotatable with rotation of the at least one spline. In another further embodiment, the method also includes rotating the at least one spline by actuating a drive input arranged at the first end and operatively coupled to the at least one spline to thereby rotate the drive gear, and actuating the activating mechanism as the drive gear rotates. In another further embodiment, the method also includes mating an instrument driver with the handle at the first end, the instrument driver being arranged at an end of a robotic arm, mating a drive output of the instrument driver with the drive input as the instrument driver is mated to the handle, and actuating the drive output to rotate the drive input and thereby actuate the activating mechanism. In another further embodiment, the method also includes mating the instrument driver with the handle at the first end comprises inserting the shaft and the end effector through a central aperture defined longitudinally through the instrument driver. In another further embodiment, the method also includes advancing at least a portion of the elevator layer past the second end before removably coupling the one or more additional layers of the carriage to the elevator layer. In another further embodiment, the method also includes penetrating the first end with the end effector and the shaft as the carriage translates distally. In another further embodiment, the method also includes removing a cap from the second end to expose a floor of the elevator layer before removably coupling the one or more additional layers of the carriage to the elevator layer. In another further embodiment, one or more snaps extend from the one or more additional layers for engaging corresponding opening in the elevator layer, and the method further includes inserting the one or more snaps of the one or more additional layers into the corresponding openings in the elevator layer and thereby securing the one or more additional layers on the elevator floor. In another further embodiment, the method also includes retaining the one or more snaps of the one or more additional layers into the corresponding openings in the elevator layer as the carriage distally translates. In another further embodiment, the handle includes a shroud within which the carriage translates, and the method further includes advancing the elevator layer such that the elevator floor and the corresponding openings extend outside of the shroud before removably coupling the one or more additional layers of the carriage to the elevator layer. In another further embodiment, the method also includes securing the one or more snaps of the one or more additional layers within the corresponding openings in the elevator layer as the carriage pulls the one or more snaps and corresponding openings into the shroud. In another further embodiment, the method also includes detaching the one or more additional layers from the elevator layer and thereby removing the one or more additional layers, the elongate shaft, and the end effector from the handle. In another further embodiment, the method also includes removably coupling one or more additional new layers of the carriage to the elevator layer, wherein a new elongate shaft extends distally from the one or more additional new layers and a new end effector is arranged at a distal end of the new elongate shaft, and penetrating the elevator layer with the new end effector and the new elongate shaft upon coupling the one or more additional new layers to the elevator layer.

Embodiments disclosed herein may further include a method that includes providing a handle having a first end, a second end, a lead screw and at least one spline extendable between the first and second ends, and an elevator layer movably mounted to the lead screw at a carriage nut, inserting the at least one spline through a drive gear housed in at least one additional layer and thereby operatively coupling the drive gear and the at least one spline such that the drive gear is rotatable with the at least one spline, and removably coupling the at least one additional layer to the elevator layer to define a carriage, wherein an elongate shaft extends distally from the one or more additional layers and an end effector is arranged at a distal end of the elongate shaft, and wherein an activating mechanism is housed in the at least one additional layer and operatively coupled to the drive gear such that rotation of the drive gear correspondingly actuates the activating mechanism. In a further embodiment, the method includes rotating the at least one spline by actuating a drive input arranged at the first end and operatively coupled to the at least one spline to thereby rotate the drive gear, and actuating the activating mechanism as the drive gear rotates.

Embodiments disclosed herein may further include a method that includes removing an end cap from a stage portion of the surgical tool, where the stage portion includes a handle having a first end and a second end, a lead screw and at least one spline extendable between the first and second ends, and an elevator layer of a carriage movably mounted to the lead screw and the at least one spline. The method may further include advancing the carriage to the second end and detaching a first instrument portion from the stage portion, where the first instrument portion includes one or more first additional layers removably coupled to the elevator layer, and a first elongate shaft extending distally from the one or more first additional layers and having a first end effector arranged at a distal end of the first shaft. The method may further include replacing the first instrument portion with a second instrument portion coupled to the stage portion, where the second instrument portion includes one or more second additional layers removably coupleable to the elevator layer, and a second elongate shaft extending distally from the one or more second additional layers and having a second end effector arranged at a distal end of the second shaft. In a further embodiment, a shroud may extend between the first and second ends, and advancing the carriage to the second end comprises advancing the carriage until the elevator layer at least partially protrudes from the shroud.

BRIEF DESCRIPTION OF THE DRAWINGS

The disclosed aspects will hereinafter be described in conjunction with the appended drawings, provided to illustrate and not to limit the disclosed aspects, wherein like designations denote like elements.

FIG. 19 illustrates the surgical tool of FIGS. 16-17 having a stage portion and an instrument portion when removed from a stage portion, according to one or more embodiments.

FIGS. 25A-25B illustrate splines configured to telescope from a handle interface when in a nested condition and when in an at least partially unnested condition, respectively, according to one or more embodiments of the present disclosure.

FIGS. 26A-26B illustrate splines configured to telescope from an elevator of the carriage when in a nested condition and when in an at least partially unnested condition, respectively, according to one or more embodiments of the present disclosure.

FIGS. 28A-28B illustrate a shroud configured to expand and contract with the telescoping splines in respective collapsed and expanded positions, according to one or more embodiments.

FIG. 36 illustrates the surgical tool having a stage sub-assembly on which a modular handle sub-assembly may be installed, according to various embodiments.

FIG. 37 illustrates an exemplary installation of the handle sub-assembly on the stage sub-assembly shown in FIG. 36.

FIGS. 42A-42D illustrate various means of providing access through which a handle sub-assembly may be dropped on or angled into a stage sub-assembly, according to various embodiments.

DETAILED DESCRIPTION

1. Overview.

Aspects of the present disclosure may be integrated into a robotically-enabled medical system capable of performing a variety of medical procedures, including both minimally invasive (e.g., laparoscopy) and non-invasive (e.g., endoscopy) procedures. Among endoscopy procedures, the system may be capable of performing bronchoscopy, ureteroscopy, gastroscopy, etc.

In addition to performing the breadth of procedures, the system may provide additional benefits, such as enhanced imaging and guidance to assist the physician. Additionally, the system may provide the physician with the ability to perform the procedure from an ergonomic position without the need for awkward arm motions and positions. Still further, the system may provide the physician with the ability to perform the procedure with improved ease of use such that one or more of the instruments of the system can be controlled by a single user.

Various embodiments will be described below in conjunction with the drawings for purposes of illustration. It should be appreciated that many other implementations of the disclosed concepts are possible, and various advantages can be achieved with the disclosed implementations. Headings are included herein for reference and to aid in locating various sections. These headings are not intended to limit the scope of the concepts described with respect thereto. Such concepts may have applicability throughout the entire specification.

A. Robotic System—Cart.

Figure 1:
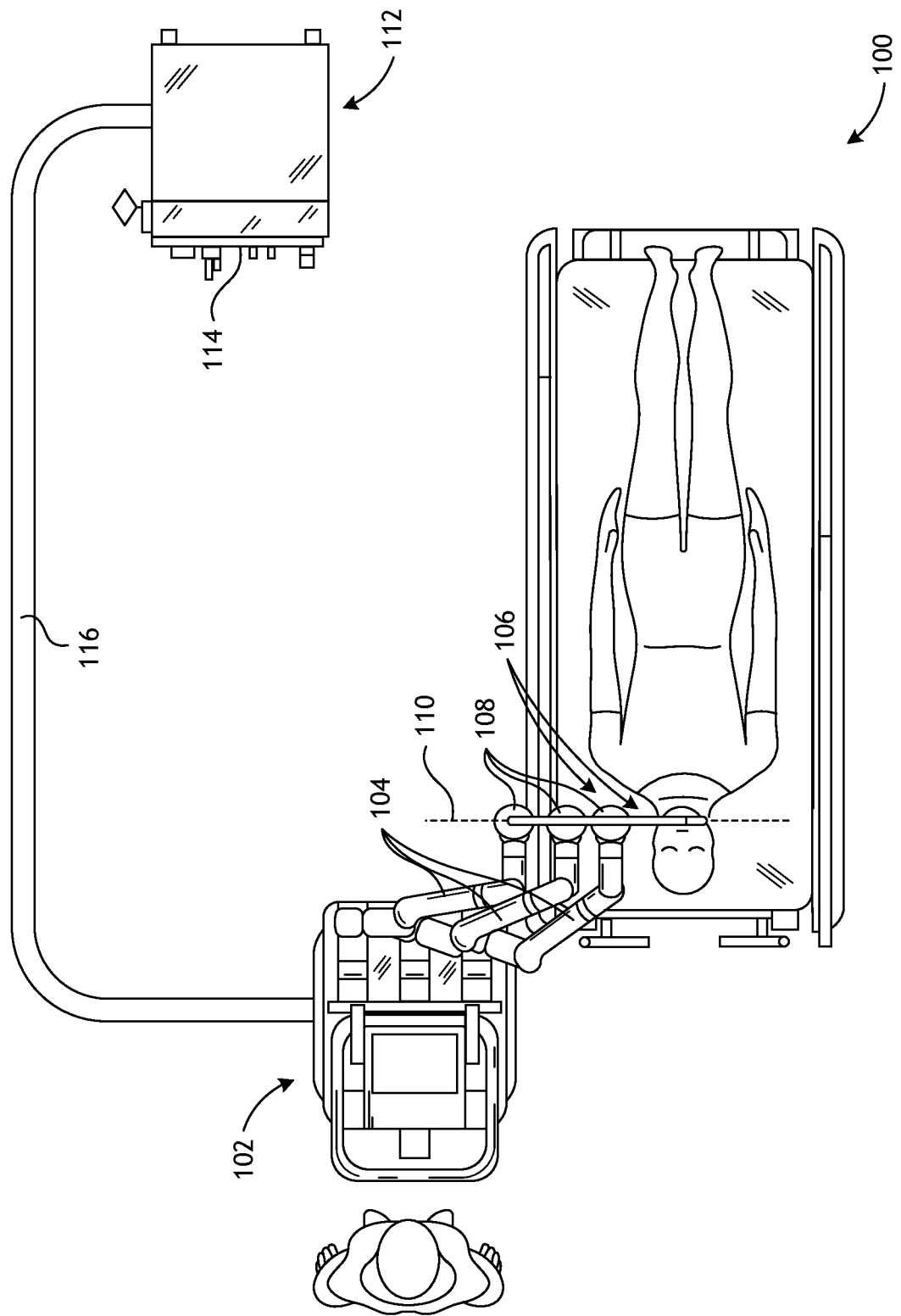
FIG. 1 illustrates an embodiment of a cart-based robotic system arranged for diagnostic and/or therapeutic bronchoscopy procedure(s).

The robotically-enabled medical system may be configured in a variety of ways depending on the particular procedure. FIG. 1 illustrates an embodiment of a cart-based robotically-enabled system 100 arranged for a diagnostic and/or therapeutic bronchoscopy procedure. For a bronchoscopy procedure, the robotic system 100 may include a cart 102 having one or more robotic arms 104 (three shown) to deliver a medical instrument (alternately referred to as a "surgical tool"), such as a steerable endoscope 106 (e.g., a procedure-specific bronchoscope for bronchoscopy), to a natural orifice access point (i.e., the mouth of the patient) to deliver diagnostic and/or therapeutic tools. As shown, the cart 102 may be positioned proximate to the patient's upper torso in order to provide access to the access point. Similarly, the robotic arms 104 may be actuated to position the bronchoscope relative to the access point. The arrangement in FIG. 1 may also be utilized when performing a gastro-intestinal (GI) procedure with a gastroscope, a specialized endoscope for GI procedures.

Once the cart 102 is properly positioned adjacent the patient, the robotic arms 104 are operated to insert the steerable endoscope 106 into the patient robotically, manually, or a combination thereof. The steerable endoscope 106 may comprise at least two telescoping parts, such as an inner leader portion and an outer sheath portion, where each portion is coupled to a separate instrument driver of a set of instrument drivers 108 (alternately referred to as "tool drivers"). As illustrated, each instrument driver 108 is coupled to the distal end of a corresponding one of the robotic arms 104. This linear arrangement of the instrument drivers 108, which facilitates coaxially aligning the leader portion with the sheath portion, creates a "virtual rail" 110 that may be repositioned in space by manipulating the robotic arms 104 into different angles and/or positions. Translation of the instrument drivers 108 along the virtual rail 110 telescopes the inner leader portion relative to the outer sheath portion, thus effectively advancing or retracting the endoscope 106 relative to the patient.

As illustrated, the virtual rail 110 (and other virtual rails described herein) is depicted in the drawings using dashed lines, thus not constituting any physical structure of the system 100. The angle of the virtual rail 110 may be adjusted, translated, and pivoted based on clinical application or physician preference. For example, in bronchoscopy, the angle and position of the virtual rail 110 as shown represents a compromise between providing physician access to the endoscope 106 while minimizing friction that results from bending the endoscope 106 into the patient's mouth.

After insertion into the patient's mouth, the endoscope 106 may be directed down the patient's trachea and lungs using precise commands from the robotic system 100 until reaching a target destination or operative site. In order to enhance navigation through the patient's lung network and/or reach the desired target, the endoscope 106 may be manipulated to telescopically extend the inner leader portion from the outer sheath portion to obtain enhanced articulation and greater bend radius. The use of separate instrument drivers 108 also allows the leader portion and sheath portion to be driven independent of each other.

For example, the endoscope 106 may be directed to deliver a biopsy needle to a target, such as, for example, a lesion or nodule within the lungs of a patient. The needle may be deployed down a working channel that runs the length of the endoscope 106 to obtain a tissue sample to be analyzed by a pathologist. Depending on the pathology results, additional tools may be deployed down the working channel of the endoscope for additional biopsies. After identifying a tissue sample to be malignant, the endoscope 106 may endoscopically deliver tools to resect the potentially cancerous tissue. In some instances, diagnostic and therapeutic treatments can be delivered in separate procedures. In those circumstances, the endoscope 106 may also be used to deliver a fiducial marker to "mark" the location of a target nodule as well. In other instances, diagnostic and therapeutic treatments may be delivered during the same procedure.

The system 100 may also include a movable tower 112, which may be connected via support cables to the cart 102 to provide support for controls, electronics, fluidics, optics, sensors, and/or power to the cart 102. Placing such functionality in the tower 112 allows for a smaller form factor cart 102 that may be more easily adjusted and/or re-positioned by an operating physician and his/her staff. Additionally, the division of functionality between the cart/table and the support tower 112 reduces operating room clutter and facilitates improving clinical workflow. While the cart 102 may be positioned close to the patient, the tower 112 may alternatively be stowed in a remote location to stay out of the way during a procedure.

In support of the robotic systems described above, the tower 112 may include component(s) of a computer-based control system that stores computer program instructions, for example, within a non-transitory computer-readable storage medium such as a persistent magnetic storage drive, solid state drive, etc. The execution of those instructions, whether the execution occurs in the tower 112 or the cart 102, may control the entire system or sub-system(s) thereof. For example, when executed by a processor of the computer system, the instructions may cause the components of the robotics system to actuate the relevant carriages and arm mounts, actuate the robotics arms, and control the medical instruments. For example, in response to receiving the control signal, motors in the joints of the robotic arms 104 may position the arms into a certain posture or angular orientation.

The tower 112 may also include one or more of a pump, flow meter, valve control, and/or fluid access in order to provide controlled irrigation and aspiration capabilities to the system 100 that may be deployed through the endoscope 106. These components may also be controlled using the computer system of the tower 112. In some embodiments, irrigation and aspiration capabilities may be delivered directly to the endoscope 106 through separate cable(s).

The tower 112 may include a voltage and surge protector designed to provide filtered and protected electrical power to the cart 102, thereby avoiding placement of a power transformer and other auxiliary power components in the cart 102, resulting in a smaller, more movable cart 102.

The tower 112 may also include support equipment for sensors deployed throughout the robotic system 100. For example, the tower 112 may include opto-electronics equipment for detecting, receiving, and processing data received from optical sensors or cameras throughout the robotic system 100. In combination with the control system, such opto-electronics equipment may be used to generate real-time images for display in any number of consoles deployed throughout the system, including in the tower 112. Similarly, the tower 112 may also include an electronic subsystem for receiving and processing signals received from deployed electromagnetic (EM) sensors. The tower 112 may also be used to house and position an EM field generator for detection by EM sensors in or on the medical instrument.

The tower 112 may also include a console 114 in addition to other consoles available in the rest of the system, e.g., a console mounted to the cart 102. The console 114 may include a user interface and a display screen (e.g., a touch-screen) for the physician operator. Consoles in the system 100 are generally designed to provide both robotic controls as well as pre-operative and real-time information of the procedure, such as navigational and localization information of a medical tool. When the console 114 is not the only console available to the physician, it may be used by a second operator, such as a nurse, to monitor the health or vitals of the patient and the operation of system, as well as provide procedure-specific data, such as navigational and localization information. In other embodiments, the console 114 may be housed in a body separate from the tower 112.

The tower 112 may be coupled to the cart 102 and endoscope 106 through one or more cables 116 connections. In some embodiments, support functionality from the tower 112 may be provided through a single cable 116 extending to the cart 102, thus simplifying and de-cluttering the operating room. In other embodiments, specific functionality may be coupled in separate cabling and connections. For example, while power may be provided through a single power cable to the cart 102, support for controls, optics, fluidics, and/or navigation may be provided through one or more separate cables.

Figure 2:
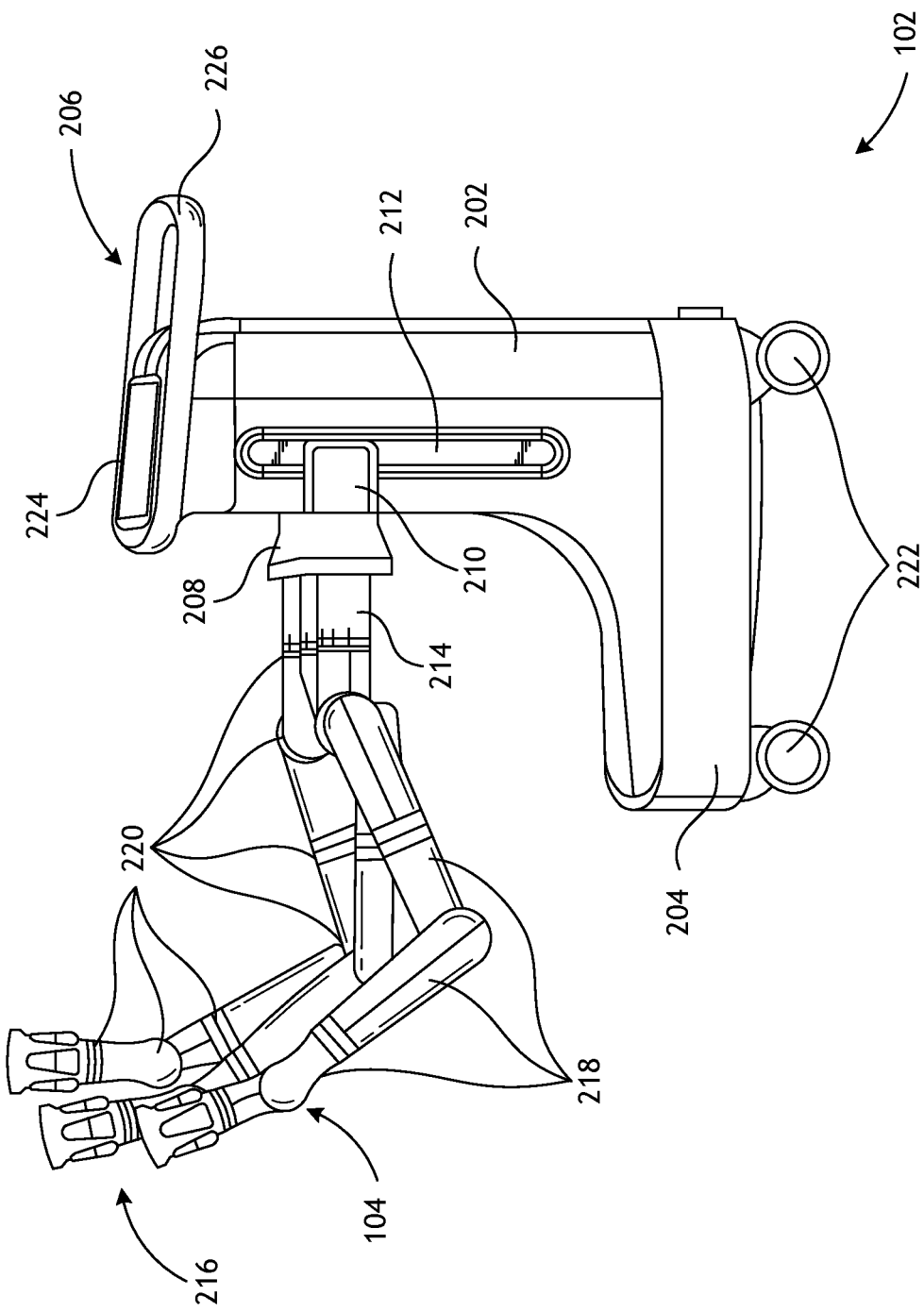
FIG. 2 depicts further aspects of the robotic system of FIG. 1.

FIG. 2 provides a detailed illustration of an embodiment of the cart 102 from the cart-based robotically-enabled system 100 of FIG. 1. The cart 102 generally includes an elongated support structure 202 (also referred to as a "column"), a cart base 204, and a console 206 at the top of the column 202. The column 202 may include one or more carriages, such as a carriage 208 (alternatively "arm support") for supporting the deployment of the robotic arms 104. The carriage 208 may include individually configurable arm mounts that rotate along a perpendicular axis to adjust the base 214 of the robotic arms 104 for better positioning relative to the patient. The carriage 208 also includes a carriage interface 210 that allows the carriage 208 to vertically translate along the column 202.

The carriage interface 210 is connected to the column 202 through slots, such as slot 212, that are positioned on opposite sides of the column 202 to guide the vertical translation of the carriage 208. The slot 212 contains a vertical translation interface to position and hold the carriage 208 at various vertical heights relative to the cart base 204. Vertical translation of the carriage 208 allows the cart 102 to adjust the reach of the robotic arms 104 to meet a variety of table heights, patient sizes, and physician preferences. Similarly, the individually configurable arm mounts on the carriage 208 allow a base 214 of the robotic arms 104 to be angled in a variety of configurations.

In some embodiments, the slot 212 may be supplemented with slot covers (not shown) that are flush and parallel to the slot surface to prevent dirt and fluid ingress into the internal chambers of the column 202 and the vertical translation interface as the carriage 208 vertically translates. The slot covers may be deployed through pairs of spring spools positioned near the vertical top and bottom of the slot 212. The covers are coiled within the spools until deployed to extend and retract from their coiled state as the carriage 208 vertically translates up and down. The spring-loading of the spools provides force to retract the cover into a spool when carriage 208 translates towards the spool, while also maintaining a tight seal when the carriage 208 translates away from the spool. The covers may be connected to the carriage 208 using, for example, brackets in the carriage interface 210 to ensure proper extension and retraction of the cover as the carriage 208 translates.

The column 202 may internally comprise mechanisms, such as gears and motors, that are designed to use a vertically aligned lead screw to translate the carriage 208 in a mechanized fashion in response to control signals generated in response to user inputs, e.g., inputs from the console 206.

The robotic arms 104 may generally comprise robotic arm bases 214 and end effectors 216 (three shown), separated by a series of linkages 218 connected by a corresponding series of joints 220, each joint 220 including an independent actuator, and each actuator including an independently controllable motor. Each independently controllable joint 220 represents an independent degree of freedom available to the corresponding robotic arm 104. In the illustrated embodiment, each arm 104 has seven joints 220, providing seven degrees of freedom. A multitude of joints 220 result in a multitude of degrees of freedom, allowing for "redundant" degrees of freedom. Redundant degrees of freedom allow the robotic arms 104 to position its respective end effectors 216 at a specific position, orientation, and trajectory in space using different linkage positions and joint angles. This allows for the system 100 to position and direct a medical instrument from a desired point in space while allowing the physician to move the arm joints 220 into a clinically advantageous position away from the patient to create greater access, while avoiding arm collisions.

The cart base 204 balances the weight of the column 202, carriage 208, and arms 104 over the floor. Accordingly, the cart base 204 houses heavier components, such as electronics, motors, power supply, as well as components that either enable movement and/or immobilize the cart. For example, the cart base 204 includes rollable casters 222 that allow for the cart 102 to easily move around a room prior to a procedure. After reaching an appropriate position, the casters 222 may be immobilized using locks to hold the cart 102 in place during the procedure.

Positioned at the vertical end of the column 202, the console 206 allows for both a user interface for receiving user input and a display screen (or a dual-purpose device such as, for example, a touchscreen 224) to provide the physician user with both pre-operative and intra-operative data. Potential pre-operative data on the touchscreen 224 may include pre-operative plans, navigation and mapping data derived from pre-operative computerized tomography (CT) scans, and/or notes from pre-operative patient interviews. Intra-operative data on the touchscreen 224 may include optical information provided from the tool, sensor and coordinate information from sensors, as well as vital patient statistics, such as respiration, heart rate, and/or pulse. The console 206 may be positioned and tilted to allow a physician to access the console from the side of the column 202 opposite carriage 208. From this position, the physician may view the console 206, the robotic arms 104, and the patient while operating the console 206 from behind the cart 102. As shown, the console 206 also includes a handle 226 to assist with maneuvering and stabilizing cart 102.

Figure 3A:
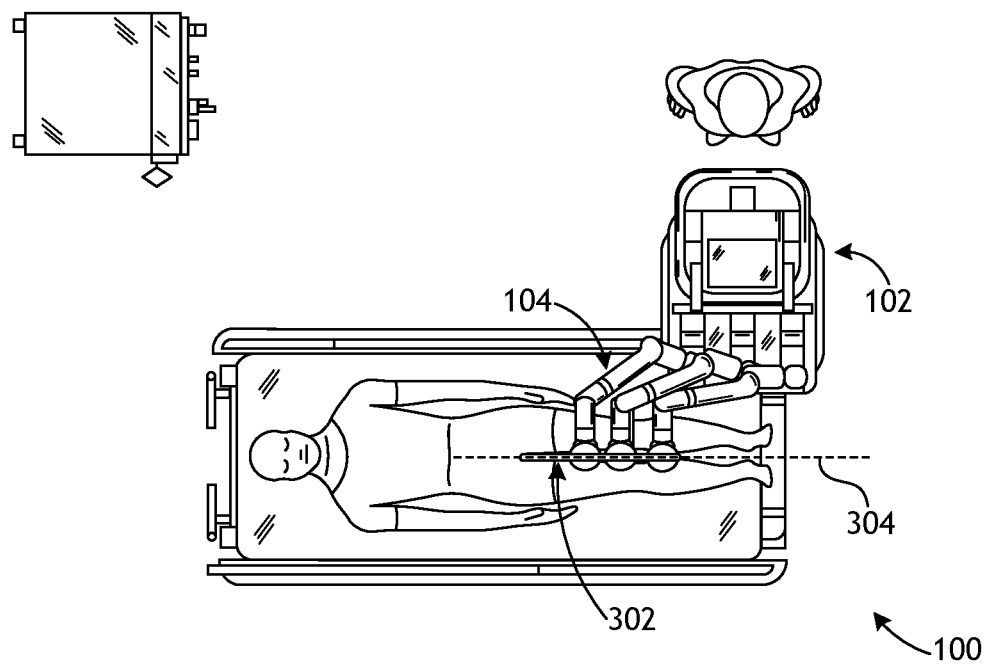
FIG. 3A illustrates an embodiment of the robotic system of FIG. 1 arranged for ureteroscopy.

FIG. 3A illustrates an embodiment of the system 100 of FIG. 1 arranged for ureteroscopy. In a ureteroscopic procedure, the cart 102 may be positioned to deliver a ureteroscope 302, a procedure-specific endoscope designed to traverse a patient's urethra and ureter, to the lower abdominal area of the patient. In ureteroscopy, it may be desirable for the ureteroscope 302 to be directly aligned with the patient's urethra to reduce friction and forces on the sensitive anatomy. As shown, the cart 102 may be aligned at the foot of the table to allow the robotic arms 104 to position the ureteroscope 302 for direct linear access to the patient's urethra. From the foot of the table, the robotic arms 104 may insert the ureteroscope 302 along a virtual rail 304 directly into the patient's lower abdomen through the urethra.

After insertion into the urethra, using similar control techniques as in bronchoscopy, the ureteroscope 302 may be navigated into the bladder, ureters, and/or kidneys for diagnostic and/or therapeutic applications. For example, the ureteroscope 302 may be directed into the ureter and kidneys to break up kidney stone build-up using a laser or ultrasonic lithotripsy device deployed down a working channel of the ureteroscope 302. After lithotripsy is complete, the resulting stone fragments may be removed using baskets deployed down the working channel of the ureteroscope 302.

Figure 3B:
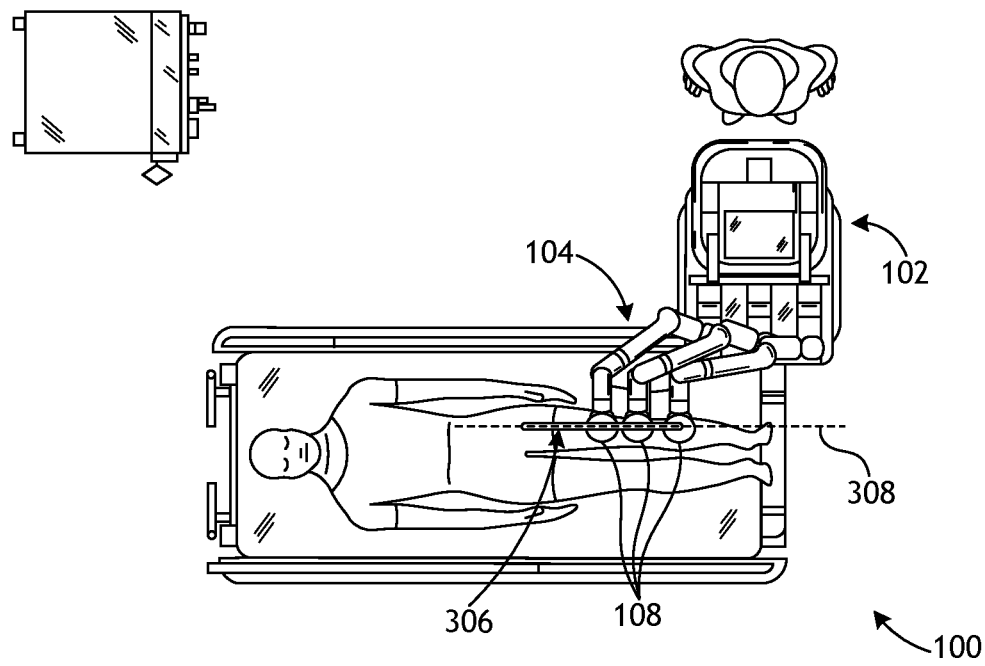
FIG. 3B illustrates an embodiment of the robotic system of FIG. 1 arranged for a vascular procedure.

FIG. 3B illustrates another embodiment of the system 100 of FIG. 1 arranged for a vascular procedure. In a vascular procedure, the system 100 may be configured such that the cart 102 may deliver a medical instrument 306, such as a steerable catheter, to an access point in the femoral artery in the patient's leg. The femoral artery presents both a larger diameter for navigation as well as a relatively less circuitous and tortuous path to the patient's heart, which simplifies navigation. As in an ureteroscopic procedure, the cart 102 may be positioned towards the patient's legs and lower abdomen to allow the robotic arms 104 to provide a virtual rail 308 with direct linear access to the femoral artery access point in the patient's thigh/hip region. After insertion into the artery, the medical instrument 306 may be directed and advanced by translating the instrument drivers 108. Alternatively, the cart 102 may be positioned around the patient's upper abdomen in order to reach alternative vascular access points, such as, for example, the carotid and brachial arteries near the patient's shoulder and wrist.

B. Robotic System—Table.

Figure 4:
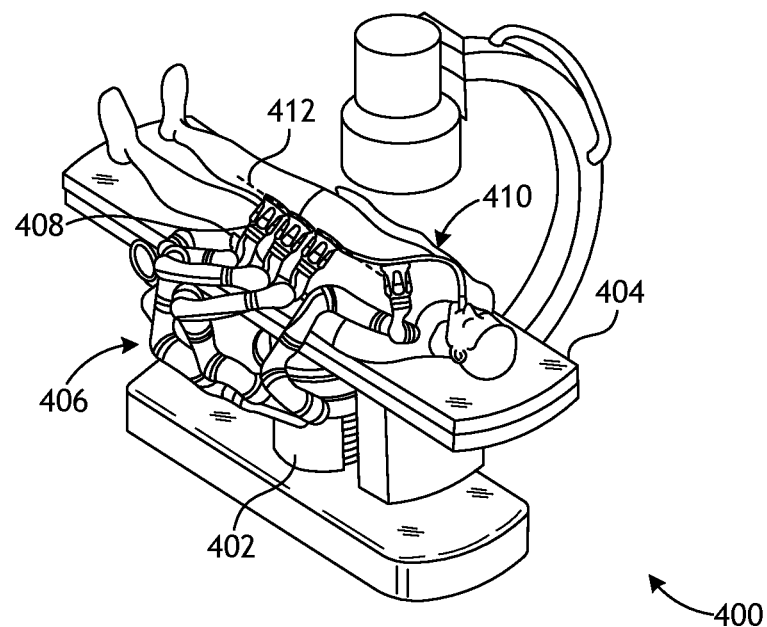
FIG. 4 illustrates an embodiment of a table-based robotic system arranged for a bronchoscopy procedure.

Embodiments of the robotically-enabled medical system may also incorporate the patient's table. Incorporation of the table reduces the amount of capital equipment within the operating room by removing the cart, which allows greater access to the patient. FIG. 4 illustrates an embodiment of such a robotically-enabled system 400 arranged for a bronchoscopy procedure. As illustrated, the system 400 includes a support structure or column 402 for supporting platform 404 (shown as a "table" or "bed") over the floor. Much like in the cart-based systems 100, end effectors of the robotic arms 406 of the system 400 comprise instrument drivers 408 (alternately referred to as "tool drivers") that are designed to manipulate an elongated medical instrument, such as a bronchoscope 410, through or along a virtual rail 412 formed from the linear alignment of the instrument drivers 408. In practice, a C-arm for providing fluoroscopic imaging may be positioned over the patient's upper abdominal area by placing the emitter and detector around the table 404.

Figure 5:
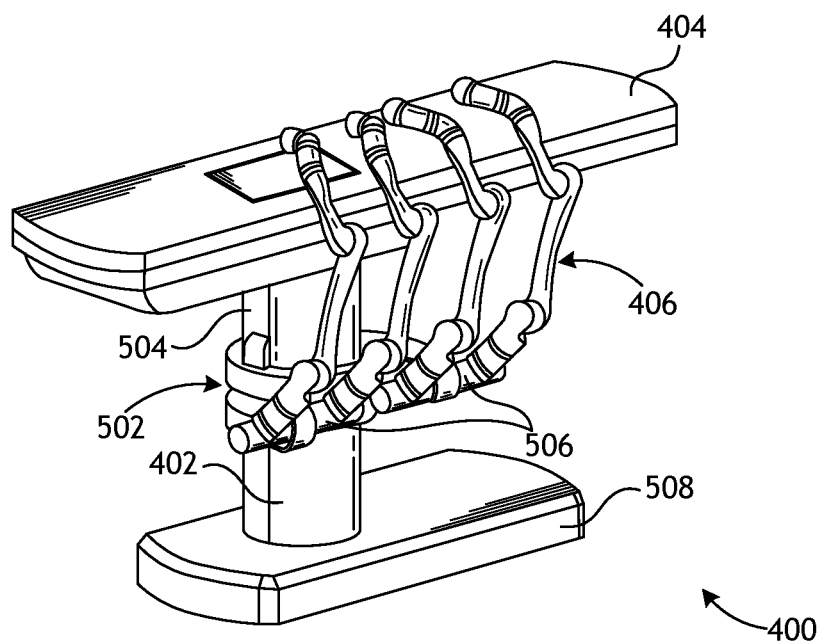
FIG. 5 provides an alternative view of the robotic system of FIG. 4.

FIG. 5 provides an alternative view of the system 400 without the patient and medical instrument for discussion purposes. As shown, the column 402 may include one or more carriages 502 shown as ring-shaped in the system 400, from which the one or more robotic arms 406 may be based. The carriages 502 may translate along a vertical column interface 504 that runs the length (height) of the column 402 to provide different vantage points from which the robotic arms 406 may be positioned to reach the patient. The carriage(s) 502 may rotate around the column 402 using a mechanical motor positioned within the column 402 to allow the robotic arms 406 to have access to multiples sides of the table 404, such as, for example, both sides of the patient. In embodiments with multiple carriages 502, the carriages 502 may be individually positioned on the column 402 and may translate and/or rotate independent of the other carriages 502. While carriages 502 need not surround the column 402 or even be circular, the ring-shape as shown facilitates rotation of the carriages 502 around the column 402 while maintaining structural balance. Rotation and translation of the carriages 502 allows the system 400 to align medical instruments, such as endoscopes and laparoscopes, into different access points on the patient.

In other embodiments (discussed in greater detail below with respect to FIG. 9A), the system 400 can include a patient table or bed with adjustable arm supports in the form of bars or rails extending alongside it. One or more robotic arms 406 (e.g., via a shoulder with an elbow joint) can be attached to the adjustable arm supports, which can be vertically adjusted. By providing vertical adjustment, the robotic arms 406 are advantageously capable of being stowed compactly beneath the patient table or bed, and subsequently raised during a procedure.

The arms 406 may be mounted on the carriages 502 through a set of arm mounts 506 comprising a series of joints that may individually rotate and/or telescopically extend to provide additional configurability to the robotic arms 406. Additionally, the arm mounts 506 may be positioned on the carriages 502 such that when the carriages 502 are appropriately rotated, the arm mounts 506 may be positioned on either the same side of the table 404 (as shown in FIG. 5), on opposite sides of table 404 (as shown in FIG. 7B), or on adjacent sides of the table 404 (not shown).

The column 402 structurally provides support for the table 404, and a path for vertical translation of the carriages 502. Internally, the column 402 may be equipped with lead screws for guiding vertical translation of the carriages, and motors to mechanize the translation of said carriages based the lead screws. The column 402 may also convey power and control signals to the carriage 502 and robotic arms 406 mounted thereon.

A table base 508 serves a similar function as the cart base 204 of the cart 102 shown in FIG. 2, housing heavier components to balance the table/bed 404, the column 402, the carriages 502, and the robotic arms 406. The table base 508 may also incorporate rigid casters to provide stability during procedures. Deployed from the bottom of the table base 508, the casters may extend in opposite directions on both sides of the base 508 and retract when the system 400 needs to be moved.

In some embodiments, the system 400 may also include a tower (not shown) that divides the functionality of system 400 between table and tower to reduce the form factor and bulk of the table 404. As in earlier disclosed embodiments, the tower may provide a variety of support functionalities to the table 404, such as processing, computing, and control capabilities, power, fluidics, and/or optical and sensor processing. The tower may also be movable to be positioned away from the patient to improve physician access and de-clutter the operating room. Additionally, placing components in the tower allows for more storage space in the table base 508 for potential stowage of the robotic arms 406. The tower may also include a master controller or console that provides both a user interface for user input, such as keyboard and/or pendant, as well as a display screen (or touchscreen) for pre-operative and intra-operative information, such as real-time imaging, navigation, and tracking information. In some embodiments, the tower may also contain holders for gas tanks to be used for insufflation.

Figure 6:
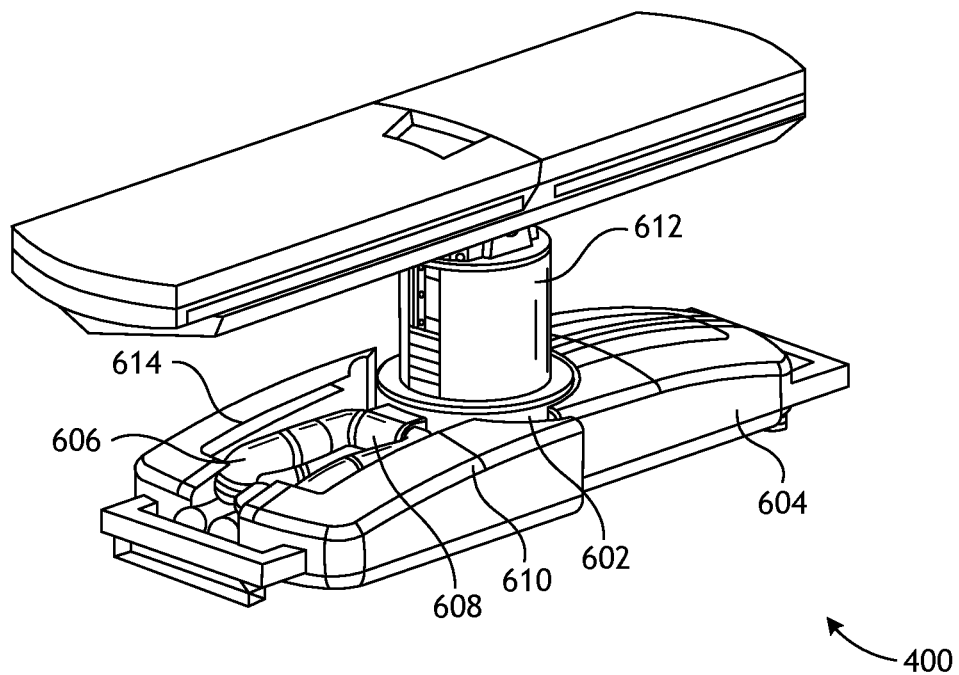
FIG. 6 illustrates an example system configured to stow robotic arm(s).

In some embodiments, a table base may stow and store the robotic arms when not in use. FIG. 6 illustrates an embodiment of the system 400 that is configured to stow robotic arms 606 within a table base 406. In the system 400, one or more carriages 602 (one shown) may be vertically translated into a base 604 to stow one or more robotic arms 606, one or more arm mounts 608, and the carriages 602 within the base 604. Base covers 610 may be translated and retracted open to deploy the carriages 602, the arm mounts 608, and the arms 606 around the column 612, and closed to stow and protect them when not in use. The base covers 610 may be sealed with a membrane 614 along the edges of its opening to prevent dirt and fluid ingress when closed.

Figure 7A:
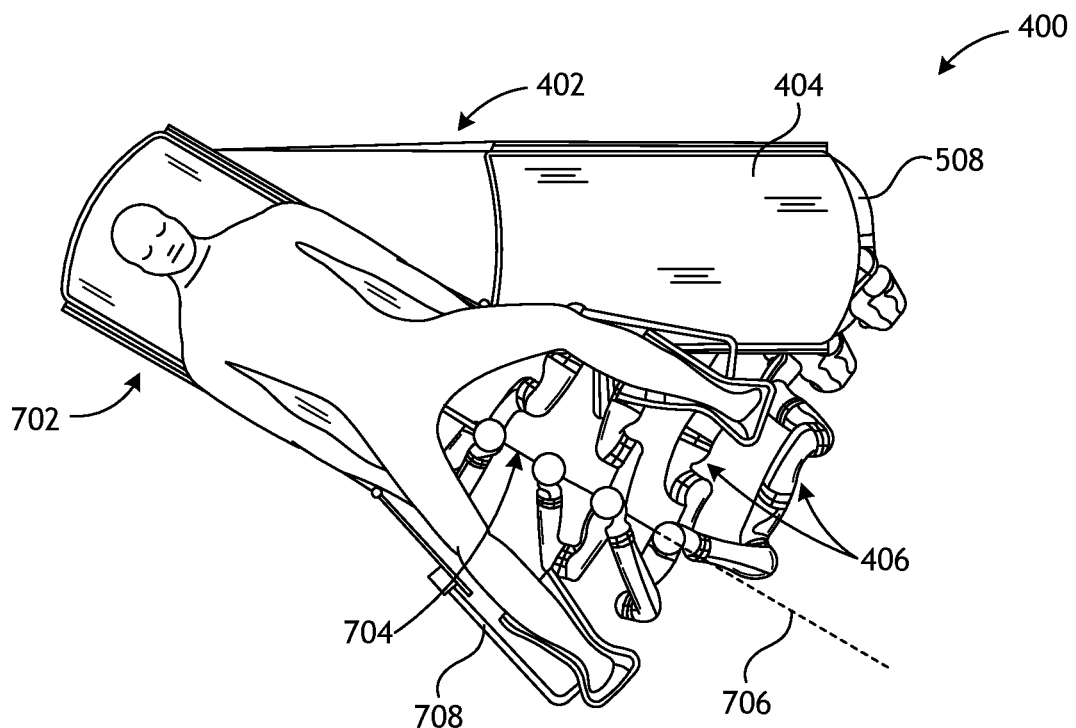
FIG. 7A illustrates an embodiment of a table-based robotic system configured for a ureteroscopy procedure.
Figure 7B:
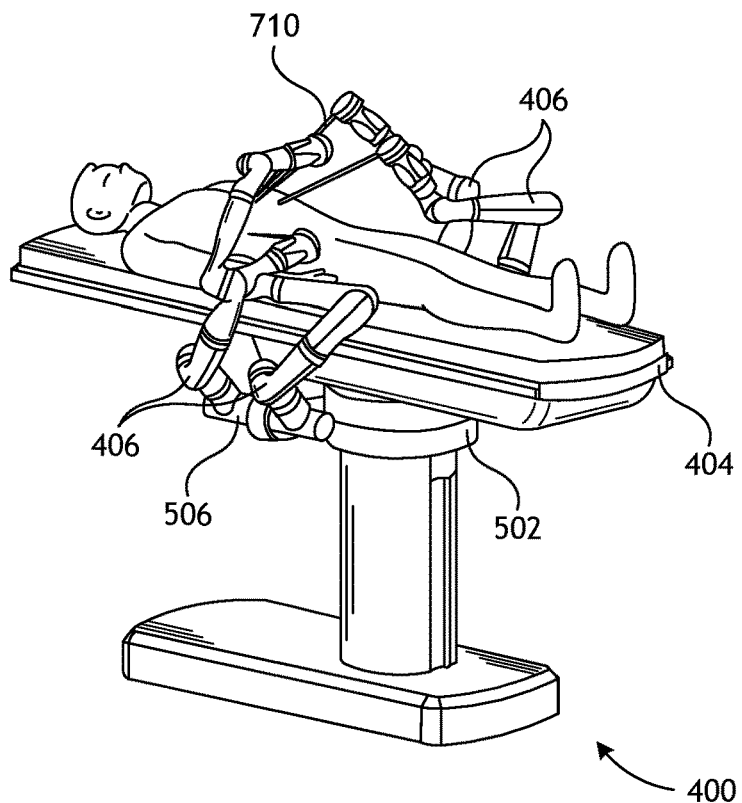
FIG. 7B illustrates an embodiment of a table-based robotic system configured for a laparoscopic procedure.

FIG. 7A illustrates an embodiment of the robotically-enabled table-based system 400 configured for a ureteroscopy procedure. In ureteroscopy, the table 404 may include a swivel portion 702 for positioning a patient off-angle from the column 402 and the table base 508. The swivel portion 702 may rotate or pivot around a pivot point (e.g., located below the patient's head) in order to position the bottom portion of the swivel portion 702 away from the column 402. For example, the pivoting of the swivel portion 702 allows a C-arm (not shown) to be positioned over the patient's lower abdomen without competing for space with the column (not shown) below table 404. By rotating the carriage (not shown) around the column 402, the robotic arms 406 may directly insert a ureteroscope 704 along a virtual rail 706 into the patient's groin area to reach the urethra. In ureteroscopy, stirrups 708 may also be fixed to the swivel portion 702 of the table 404 to support the position of the patient's legs during the procedure and allow clear access to the patient's groin area.

FIG. 7B illustrates an embodiment of the system 400 configured for a laparoscopic procedure. In a laparoscopic procedure, through small incision(s) in the patient's abdominal wall, minimally invasive instruments may be inserted into the patient's anatomy. In some embodiments, the minimally invasive instruments comprise an elongated rigid member, such as a shaft, which is used to access anatomy within the patient. After inflation of the patient's abdominal cavity, the instruments may be directed to perform surgical or medical tasks, such as grasping, cutting, ablating, suturing, etc. In some embodiments, the instruments can comprise a scope, such as a laparoscope. As shown in FIG. 7B, the carriages 502 of the system 400 may be rotated and vertically adjusted to position pairs of the robotic arms 406 on opposite sides of the table 404, such that an instrument 710 may be positioned using the arm mounts 506 to be passed through minimal incisions on both sides of the patient to reach his/her abdominal cavity.

Figure 7C:
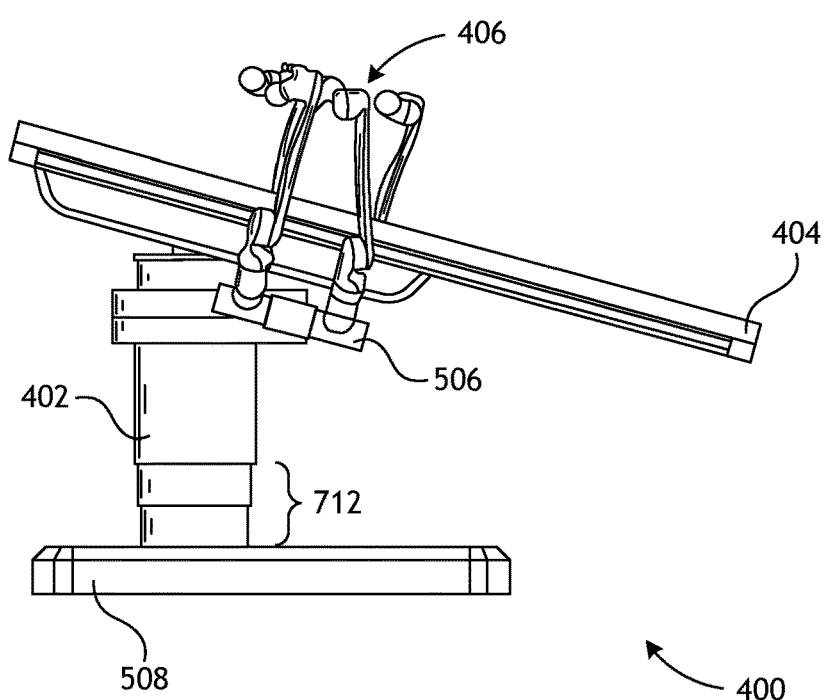
FIG. 7C illustrates an embodiment of the table-based robotic system of FIGS. 4-7B with pitch or tilt adjustment.

To accommodate laparoscopic procedures, the system 400 may also tilt the platform to a desired angle. FIG. 7C illustrates an embodiment of the system 400 with pitch or tilt adjustment. As shown in FIG. 7C, the system 400 may accommodate tilt of the table 404 to position one portion of the table 404 at a greater distance from the floor than the other. Additionally, the arm mounts 506 may rotate to match the tilt such that the arms 406 maintain the same planar relationship with table 404. To accommodate steeper angles, the column 402 may also include telescoping portions 712 that allow vertical extension of the column 402 to keep the table 404 from touching the floor or colliding with the base 508.

Figure 8:
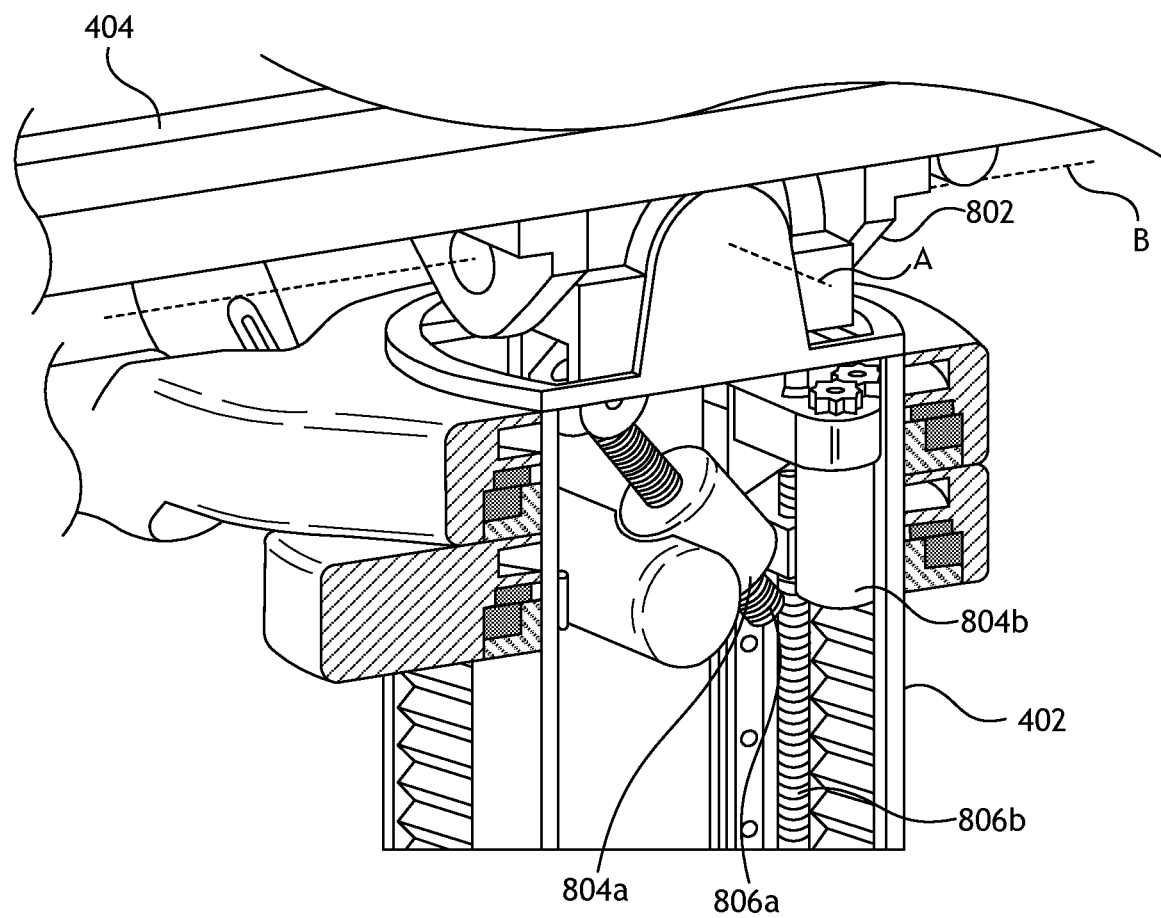
FIG. 8 provides a detailed illustration of the interface between the table and the column of the table-based robotic system of FIGS. 4-7.

FIG. 8 provides a detailed illustration of the interface between the table 404 and the column 402. Pitch rotation mechanism 802 may be configured to alter the pitch angle of the table 404 relative to the column 402 in multiple degrees of freedom. The pitch rotation mechanism 802 may be enabled by the positioning of orthogonal axes A and B at the column-table interface, each axis actuated by a separate motor 804a and 804b responsive to an electrical pitch angle command. Rotation along one screw 806a would enable tilt adjustments in one axis A, while rotation along another screw 806b would enable tilt adjustments along the other axis B. In some embodiments, a ball joint can be used to alter the pitch angle of the table 404 relative to the column 402 in multiple degrees of freedom.

For example, pitch adjustments are particularly useful when trying to position the table in a Trendelenburg position, i.e., position the patient's lower abdomen at a higher position from the floor than the patient's lower abdomen, for lower abdominal surgery. The Trendelenburg position causes the patient's internal organs to slide towards his/her upper abdomen through the force of gravity, clearing out the abdominal cavity for minimally invasive tools to enter and perform lower abdominal surgical or medical procedures, such as laparoscopic prostatectomy.

Figure 9A:
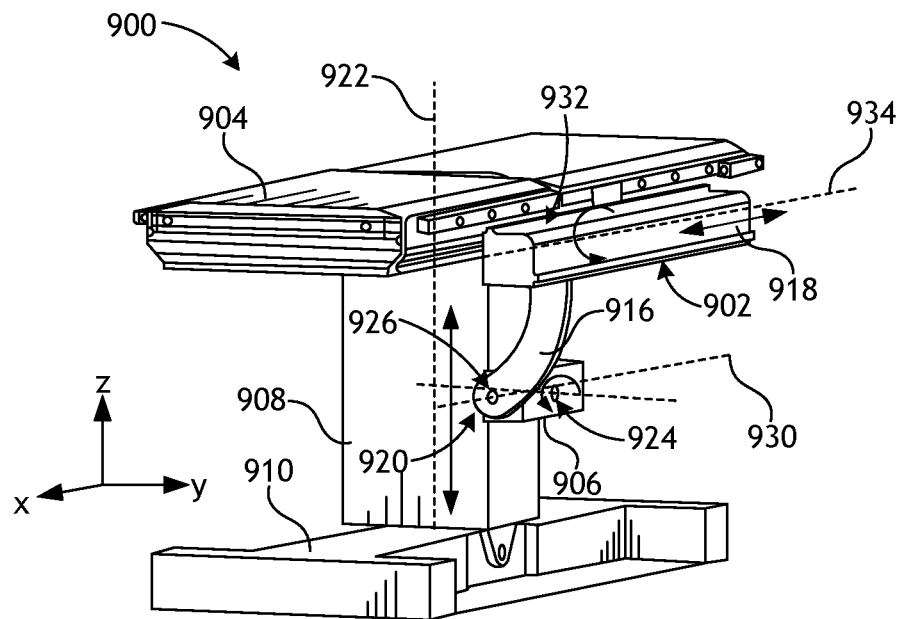
FIG. 9A illustrates an alternative embodiment of a table-based robotic system.
Figure 9B:
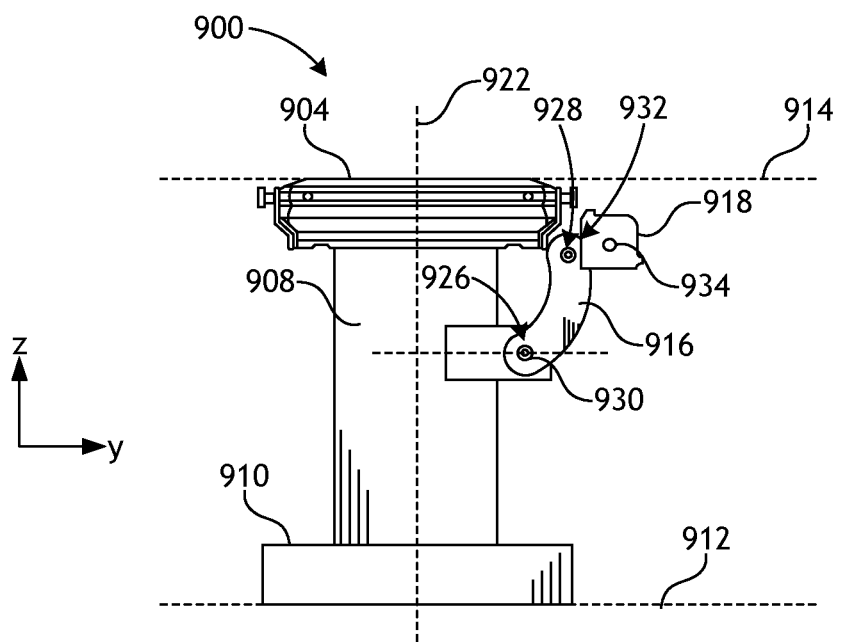
FIG. 9B illustrates an end view of the table-based robotic system of FIG. 9A.

FIGS. 9A and 9B illustrate isometric and end views, respectively, of an alternative embodiment of a table-based surgical robotics system 900. The surgical robotics system 900 includes one or more adjustable arm supports 902 that can be configured to support one or more robotic arms (see, for example, FIG. 9C) relative to a table 904. In the illustrated embodiment, a single adjustable arm support 902 is shown, though an additional arm support can be provided on an opposite side of the table 904. The adjustable arm support 902 can be configured so that it can move relative to the table 904 to adjust and/or vary the position of the adjustable arm support 902 and/or any robotic arms mounted thereto relative to the table 904. For example, the adjustable arm support 902 may be adjusted in one or more degrees of freedom relative to the table 904. The adjustable arm support 902 provides high versatility to the system 900, including the ability to easily stow the one or more adjustable arm supports 902 and any robotics arms attached thereto beneath the table 904. The adjustable arm support 902 can be elevated from the stowed position to a position below an upper surface of the table 904. In other embodiments, the adjustable arm support 902 can be elevated from the stowed position to a position above an upper surface of the table 904.

The adjustable arm support 902 can provide several degrees of freedom, including lift, lateral translation, tilt, etc. In the illustrated embodiment of FIGS. 9A and 9B, the arm support 902 is configured with four degrees of freedom, which are illustrated with arrows in FIG. 9A. A first degree of freedom allows for adjustment of the adjustable arm support 902 in the z-direction ("Z-lift"). For example, the adjustable arm support 902 can include a carriage 906 configured to move up or down along or relative to a column 908 supporting the table 904. A second degree of freedom can allow the adjustable arm support 902 to tilt. For example, the adjustable arm support 902 can include a rotary joint, which can allow the adjustable arm support 902 to be aligned with the bed in a Trendelenburg position. A third degree of freedom can allow the adjustable arm support 902 to "pivot up," which can be used to adjust a distance between a side of the table 904 and the adjustable arm support 902. A fourth degree of freedom can permit translation of the adjustable arm support 902 along a longitudinal length of the table.

The surgical robotics system 900 in FIGS. 9A and 9B can comprise a table 904 supported by a column 908 that is mounted to a base 910. The base 910 and the column 908 support the table 904 relative to a support surface. A floor axis 912 and a support axis 914 are shown in FIG. 9B.

The adjustable arm support 902 can be mounted to the column 908. In other embodiments, the arm support 902 can be mounted to the table 904 or the base 910. The adjustable arm support 902 can include a carriage 906, a bar or rail connector 916 and a bar or rail 918. In some embodiments, one or more robotic arms mounted to the rail 918 can translate and move relative to one another.

The carriage 906 can be attached to the column 908 by a first joint 920, which allows the carriage 906 to move relative to the column 908 (e.g., such as up and down a first or vertical axis 922). The first joint 920 can provide the first degree of freedom ("Z-lift") to the adjustable arm support 902. The adjustable arm support 902 can include a second joint 924, which provides the second degree of freedom (tilt) for the adjustable arm support 902. The adjustable arm support 902 can include a third joint 926, which can provide the third degree of freedom ("pivot up") for the adjustable arm support 902. An additional joint 928 (shown in FIG. 9B) can be provided that mechanically constrains the third joint 926 to maintain an orientation of the rail 918 as the rail connector 916 is rotated about a third axis 930. The adjustable arm support 902 can include a fourth joint 932, which can provide a fourth degree of freedom (translation) for the adjustable arm support 902 along a fourth axis 934.

Figure 9C:
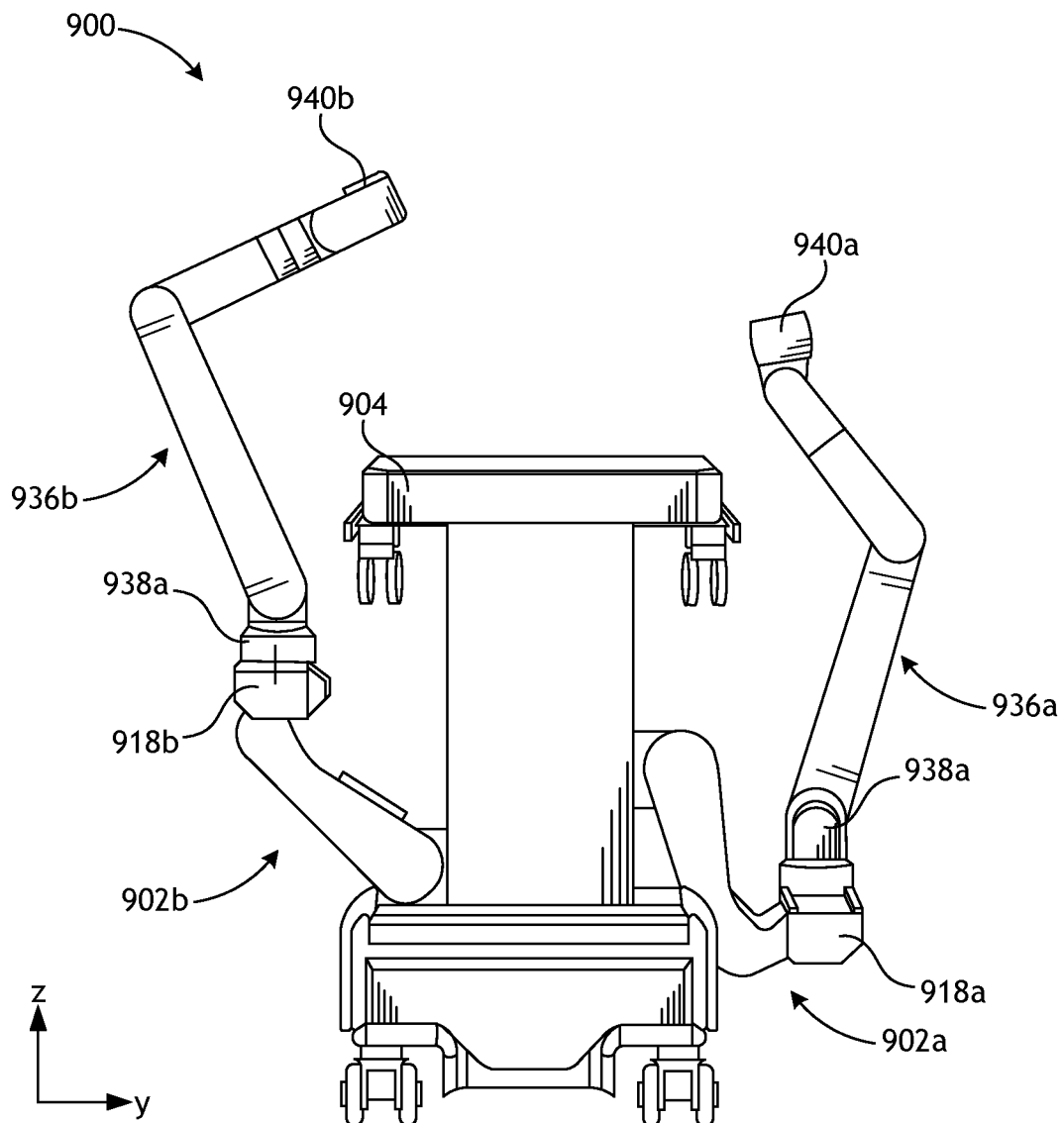
FIG. 9C illustrates an end view of a table-based robotic system with robotic arms attached thereto.

FIG. 9C illustrates an end view of the surgical robotics system 900 with two adjustable arm supports 902a and 902b mounted on opposite sides of the table 904. A first robotic arm 936a is attached to the first bar or rail 918a of the first adjustable arm support 902a. The first robotic arm 936a includes a base 938a attached to the first rail 918a. The distal end of the first robotic arm 936a includes an instrument drive mechanism or input 940a that can attach to one or more robotic medical instruments or tools. Similarly, the second robotic arm 936b includes a base 938a attached to the second rail 918b. The distal end of the second robotic arm 936b includes an instrument drive mechanism or input 940b configured to attach to one or more robotic medical instruments or tools.

In some embodiments, one or more of the robotic arms 936a,b comprises an arm with seven or more degrees of freedom. In some embodiments, one or more of the robotic arms 936a,b can include eight degrees of freedom, including an insertion axis (1-degree of freedom including insertion), a wrist (3-degrees of freedom including wrist pitch, yaw and roll), an elbow (1-degree of freedom including elbow pitch), a shoulder (2-degrees of freedom including shoulder pitch and yaw), and base 938a,b (1-degree of freedom including translation). In some embodiments, the insertion degree of freedom can be provided by the robotic arm 936a,b, while in other embodiments, the instrument itself provides insertion via an instrument-based insertion architecture.

C. Instrument Driver & Interface.

The end effectors of a system's robotic arms comprise (i) an instrument driver (alternatively referred to as "tool driver," "instrument drive mechanism," "instrument device manipulator," and "drive input") that incorporate electro-mechanical means for actuating the medical instrument and, (ii) a removable or detachable medical instrument, which may be devoid of any electro-mechanical components, such as motors. This dichotomy may be driven by the need to sterilize medical instruments used in medical procedures, and the inability to adequately sterilize expensive capital equipment due to their intricate mechanical assemblies and sensitive electronics. Accordingly, the medical instruments may be designed to be detached, removed, and interchanged from the instrument driver (and thus the system) for individual sterilization or disposal by the physician or the physician's staff. In contrast, the instrument drivers need not be changed or sterilized, and may be draped for protection.

Figure 10:
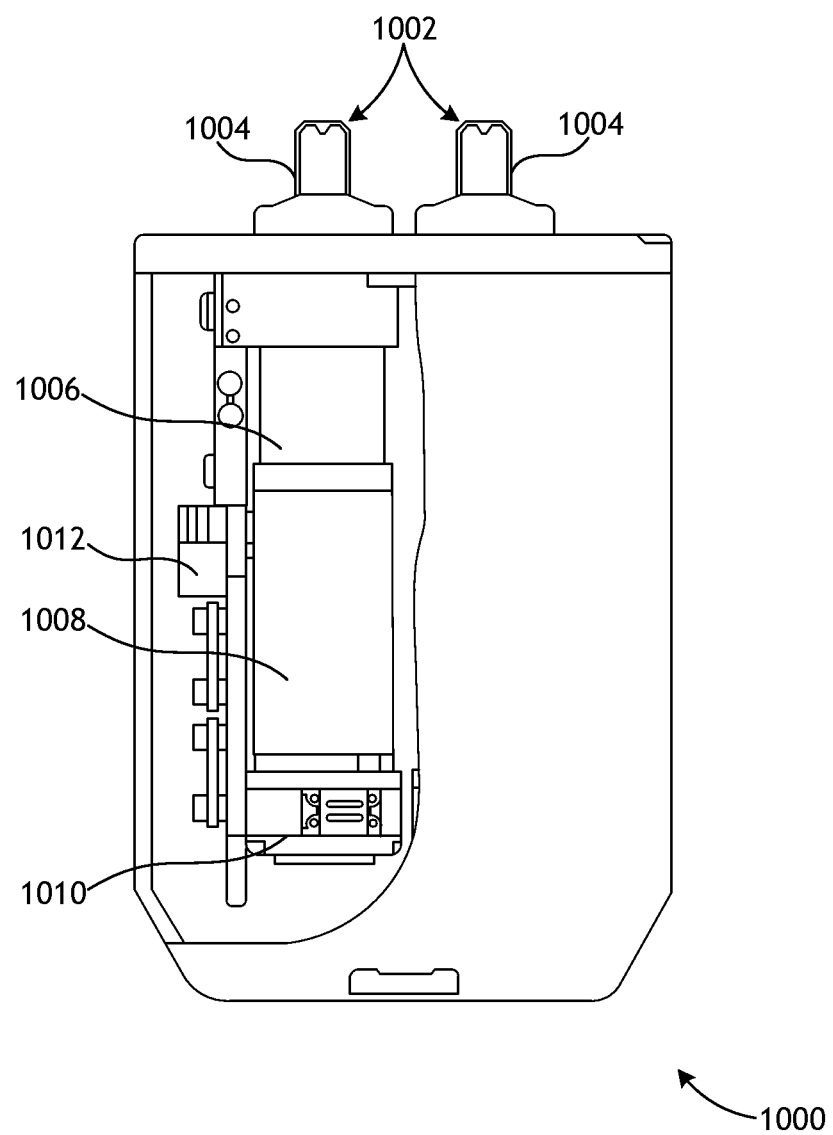
FIG. 10 illustrates an exemplary instrument driver.

FIG. 10 illustrates an example instrument driver 1000, according to one or more embodiments. Positioned at the distal end of a robotic arm, the instrument driver 1000 comprises of one or more drive output 1002 arranged with parallel axes to provide controlled torque to a medical instrument via corresponding drive shafts 1004. Each drive output 1002 comprises an individual drive shaft 1004 for interacting with the instrument, a gear head 1006 for converting the motor shaft rotation to a desired torque, a motor 1008 for generating the drive torque, and an encoder 1010 to measure the speed of the motor shaft and provide feedback to control circuitry 1012, which can also be used for receiving control signals and actuating the drive output 1002. Each drive output 1002 being independent controlled and motorized, the instrument driver 1000 may provide multiple (at least two shown in FIG. 10) independent drive outputs to the medical instrument. In operation, the control circuitry 1012 receives a control signal, transmits a motor signal to the motor 1008, compares the resulting motor speed as measured by the encoder 1010 with the desired speed, and modulates the motor signal to generate the desired torque.

For procedures that require a sterile environment, the robotic system may incorporate a drive interface, such as a sterile adapter connected to a sterile drape, that sits between the instrument driver and the medical instrument. The chief purpose of the sterile adapter is to transfer angular motion from the drive shafts of the instrument driver to the drive inputs of the instrument while maintaining physical separation, and thus sterility, between the drive shafts and drive inputs. Accordingly, an example sterile adapter may comprise of a series of rotational inputs and outputs intended to be mated with the drive shafts of the instrument driver and drive inputs on the instrument. Connected to the sterile adapter, the sterile drape, comprised of a thin, flexible material such as transparent or translucent plastic, is designed to cover the capital equipment, such as the instrument driver, robotic arm, and cart (in a cart-based system) or table (in a table-based system). Use of the drape would allow the capital equipment to be positioned proximate to the patient while still being located in an area not requiring sterilization (i.e., non-sterile field). On the other side of the sterile drape, the medical instrument may interface with the patient in an area requiring sterilization (i.e., sterile field).

D. Medical Instrument.

Figure 11:
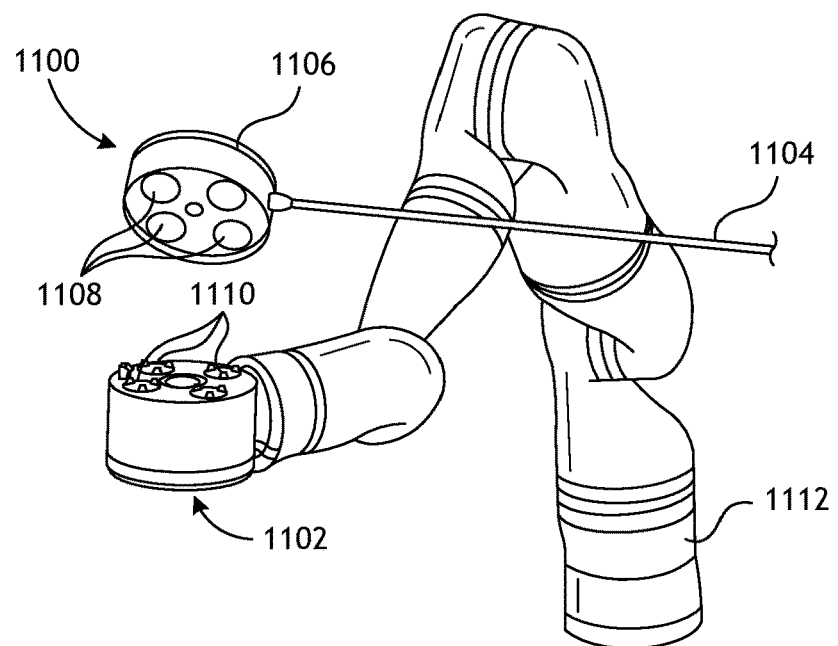
FIG. 11 illustrates an exemplary medical instrument with a paired instrument driver.

FIG. 11 illustrates an example medical instrument 1100 with a paired instrument driver 1102. Like other instruments designed for use with a robotic system, the medical instrument 1100 (alternately referred to as a "surgical tool") comprises an elongated shaft 1104 (or elongate body) and an instrument base 1106. The instrument base 1106, also referred to as an "instrument handle" due to its intended design for manual interaction by the physician, may generally comprise rotatable drive inputs 1108, e.g., receptacles, pulleys or spools, that are designed to be mated with drive outputs 1110 that extend through a drive interface on the instrument driver 1102 at the distal end of a robotic arm 1112. When physically connected, latched, and/or coupled, the mated drive inputs 1108 of the instrument base 1106 may share axes of rotation with the drive outputs 1110 in the instrument driver 1102 to allow the transfer of torque from the drive outputs 1110 to the drive inputs 1108. In some embodiments, the drive outputs 1110 may comprise splines that are designed to mate with receptacles on the drive inputs 1108.

The elongated shaft 1104 is designed to be delivered through either an anatomical opening or lumen, e.g., as in endoscopy, or a minimally invasive incision, e.g., as in laparoscopy. The elongated shaft 1104 may be either flexible (e.g., having properties similar to an endoscope) or rigid (e.g., having properties similar to a laparoscope) or contain a customized combination of both flexible and rigid portions. When designed for laparoscopy, the distal end of a rigid elongated shaft 1104 may be connected to an end effector of a surgical tool or medical instrument extending from a jointed wrist formed from a clevis with at least one degree of freedom, such as, for example, a grasper or scissors, that may be actuated based on force from the tendons as the drive inputs 1108 rotate in response to torque received from the drive outputs 1110 of the instrument driver 1102. When designed for endoscopy, the distal end of the flexible elongated shaft 1104 may include a steerable or controllable bending section that may be articulated and bent based on torque received from the drive outputs 1110 of the instrument driver 1102.

In some embodiments, torque from the instrument driver 1102 is transmitted down the elongated shaft 1104 using tendons along the shaft 1104. These individual tendons, such as pull wires, may be individually anchored to individual drive inputs 1108 within the instrument handle 1106. From the handle 1106, the tendons are directed down one or more pull lumens along the elongated shaft 1104 and anchored at the distal portion of the elongated shaft 1104, or in the wrist at the distal portion of the elongated shaft. During a surgical procedure, such as a laparoscopic, endoscopic, or a hybrid procedure, these tendons may be coupled to a distally mounted end effector, such as a wrist, a grasper, or scissors. Under such an arrangement, torque exerted on the drive inputs 1108 would transfer tension to the tendon, thereby causing the end effector to actuate in some way. In some embodiments, during a surgical procedure, the tendon may cause a joint to rotate about an axis, thereby causing the end effector to move in one direction or another. Alternatively, the tendon may be connected to one or more jaws of a grasper at distal end of the elongated shaft 1104, where tension from the tendon cause the grasper to close.

In endoscopy, the tendons may be coupled to a bending or articulating section positioned along the elongated shaft 1104 (e.g., at the distal end) via adhesive, control ring, or other mechanical fixation. When fixedly attached to the distal end of a bending section, torque exerted on drive inputs 1108 would be transmitted down the tendons, causing the softer, bending section (sometimes referred to as the articulable section or region) to bend or articulate. Along the non-bending sections, it may be advantageous to spiral or helix the individual pull lumens that direct the individual tendons along (or inside) the walls of the endoscope shaft to balance the radial forces that result from tension in the pull wires. The angle of the spiraling and/or spacing there between may be altered or engineered for specific purposes, wherein tighter spiraling exhibits lesser shaft compression under load forces, while lower amounts of spiraling results in greater shaft compression under load forces, but also exhibits limits bending. On the other end of the spectrum, the pull lumens may be directed parallel to the longitudinal axis of the elongated shaft 1104 to allow for controlled articulation in the desired bending or articulable sections.

In endoscopy, the elongated shaft 1104 houses a number of components to assist with the robotic procedure. The shaft may comprise of a working channel for deploying surgical tools (or medical instruments), irrigation, and/or aspiration to the operative region at the distal end of the shaft 1104. The shaft 1104 may also accommodate wires and/or optical fibers to transfer signals to/from an optical assembly at the distal tip, which may include of an optical camera. The shaft 1104 may also accommodate optical fibers to carry light from proximally-located light sources, such as light emitting diodes, to the distal end of the shaft.

At the distal end of the instrument 1100, the distal tip may also comprise the opening of a working channel for delivering tools for diagnostic and/or therapy, irrigation, and aspiration to an operative site. The distal tip may also include a port for a camera, such as a fiberscope or a digital camera, to capture images of an internal anatomical space. Relatedly, the distal tip may also include ports for light sources for illuminating the anatomical space when using the camera.

In the example of FIG. 11, the drive shaft axes, and thus the drive input axes, are orthogonal to the axis of the elongated shaft. This arrangement, however, complicates roll capabilities for the elongated shaft 1104. Rolling the elongated shaft 1104 along its axis while keeping the drive inputs 1108 static results in undesirable tangling of the tendons as they extend off the drive inputs 1108 and enter pull lumens within the elongated shaft 1104. The resulting entanglement of such tendons may disrupt any control algorithms intended to predict movement of the flexible elongated shaft during an endoscopic procedure.

Figure 12:
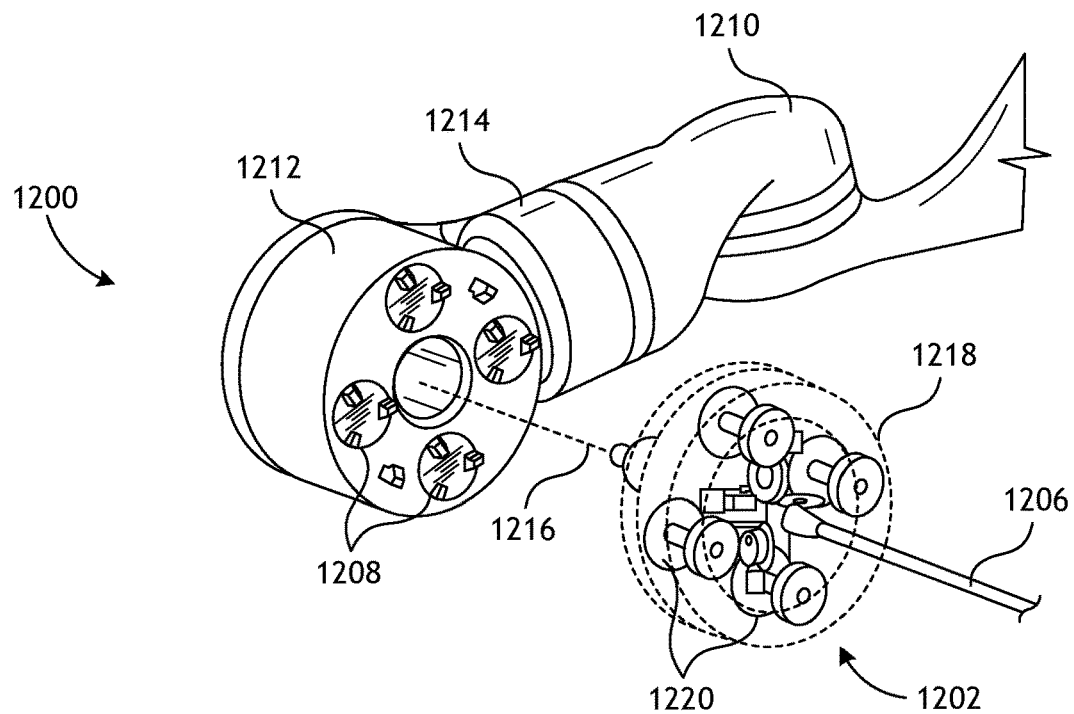
FIG. 12 illustrates an alternative design for an instrument driver and instrument where the axes of the drive units are parallel to the axis of the elongated shaft of the instrument.

FIG. 12 illustrates an alternative design for a circular instrument driver 1200 and corresponding instrument 1202 (alternately referred to as a "surgical tool") where the axes of the drive units are parallel to the axis of the elongated shaft 1206 of the instrument 1202. As shown, the instrument driver 1200 comprises four drive units with corresponding drive outputs 1208 aligned in parallel at the end of a robotic arm 1210. The drive units and their respective drive outputs 1208 are housed in a rotational assembly 1212 of the instrument driver 1200 that is driven by one of the drive units within the assembly 1212. In response to torque provided by the rotational drive unit, the rotational assembly 1212 rotates along a circular bearing that connects the rotational assembly 1212 to a non-rotational portion 1214 of the instrument driver 1200. Power and control signals may be communicated from the non-rotational portion 1214 of the instrument driver 1200 to the rotational assembly 1212 through electrical contacts maintained through rotation by a brushed slip ring connection (not shown). In other embodiments, the rotational assembly 1212 may be responsive to a separate drive unit that is integrated into the non-rotatable portion 1214, and thus not in parallel with the other drive units. The rotational assembly 1212 allows the instrument driver 1200 to rotate the drive units and their respective drive outputs 1208 as a single unit around an instrument driver axis 1216.

Like earlier disclosed embodiments, the instrument 1202 may include an elongated shaft 1206 and an instrument base 1218 (shown in phantom) including a plurality of drive inputs 1220 (such as receptacles, pulleys, and spools) that are configured to mate with the drive outputs 1208 of the instrument driver 1200. Unlike prior disclosed embodiments, the instrument shaft 1206 extends from the center of the instrument base 1218 with an axis substantially parallel to the axes of the drive inputs 1220, rather than orthogonal as in the design of FIG. 11.

When coupled to the rotational assembly 1212 of the instrument driver 1200, the medical instrument 1202, comprising instrument base 1218 and instrument shaft 1206, rotates in combination with the rotational assembly 1212 about the instrument driver axis 1216. Since the instrument shaft 1206 is positioned at the center of the instrument base 1218, the instrument shaft 1206 is coaxial with the instrument driver axis 1216 when attached. Thus, rotation of the rotational assembly 1212 causes the instrument shaft 1206 to rotate about its own longitudinal axis. Moreover, as the instrument base 1218 rotates with the instrument shaft 1206, any tendons connected to the drive inputs 1220 in the instrument base 1218 are not tangled during rotation. Accordingly, the parallelism of the axes of the drive outputs 1208, the drive inputs 1220, and the instrument shaft 1206 allows for the shaft rotation without tangling any control tendons.

Figure 13:
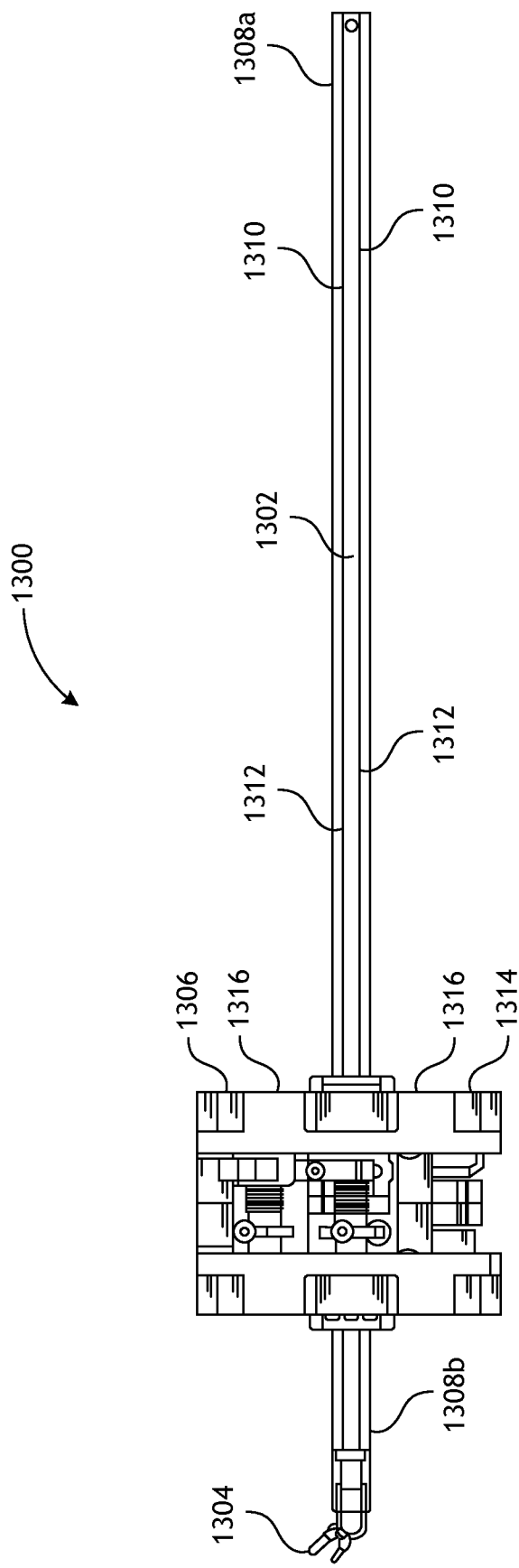
FIG. 13 illustrates an instrument having an instrument-based insertion architecture.

FIG. 13 illustrates a medical instrument 1300 having an instrument based insertion architecture in accordance with some embodiments. The instrument 1300 (alternately referred to as a "surgical tool") can be coupled to any of the instrument drivers discussed herein above and, as illustrated, can include an elongated shaft 1302, an end effector 1304 connected to the shaft 1302, and a handle 1306 coupled to the shaft 1302. The elongated shaft 1302 comprises a tubular member having a proximal portion 1308a and a distal portion 1308b. The elongated shaft 1302 comprises one or more channels or grooves 1310 along its outer surface and configured to receive one or more wires or cables 1312 therethrough. One or more cables 1312 thus run along an outer surface of the elongated shaft 1302. In other embodiments, the cables 1312 can also run through the elongated shaft 1302. Manipulation of the cables 1312 (e.g., via an instrument driver) results in actuation of the end effector 1304.

The instrument handle 1306, which may also be referred to as an instrument base, may generally comprise an attachment interface 1314 having one or more mechanical inputs 1316, e.g., receptacles, pulleys or spools, that are designed to be reciprocally mated with one or more torque couplers on an attachment surface of an instrument driver.

In some embodiments, the instrument 1300 comprises a series of pulleys or cables that enable the elongated shaft 1302 to translate relative to the handle 1306. In other words, the instrument 1300 itself comprises an instrument-based insertion architecture that accommodates insertion of the instrument, thereby minimizing the reliance on a robot arm to provide insertion of the instrument 1300. In other embodiments, a robotic arm can be largely responsible for instrument insertion.

E. Controller.

Any of the robotic systems described herein can include an input device or controller for manipulating an instrument attached to a robotic arm. In some embodiments, the controller can be coupled (e.g., communicatively, electronically, electrically, wirelessly and/or mechanically) with an instrument such that manipulation of the controller causes a corresponding manipulation of the instrument e.g., via master slave control.

Figure 14:
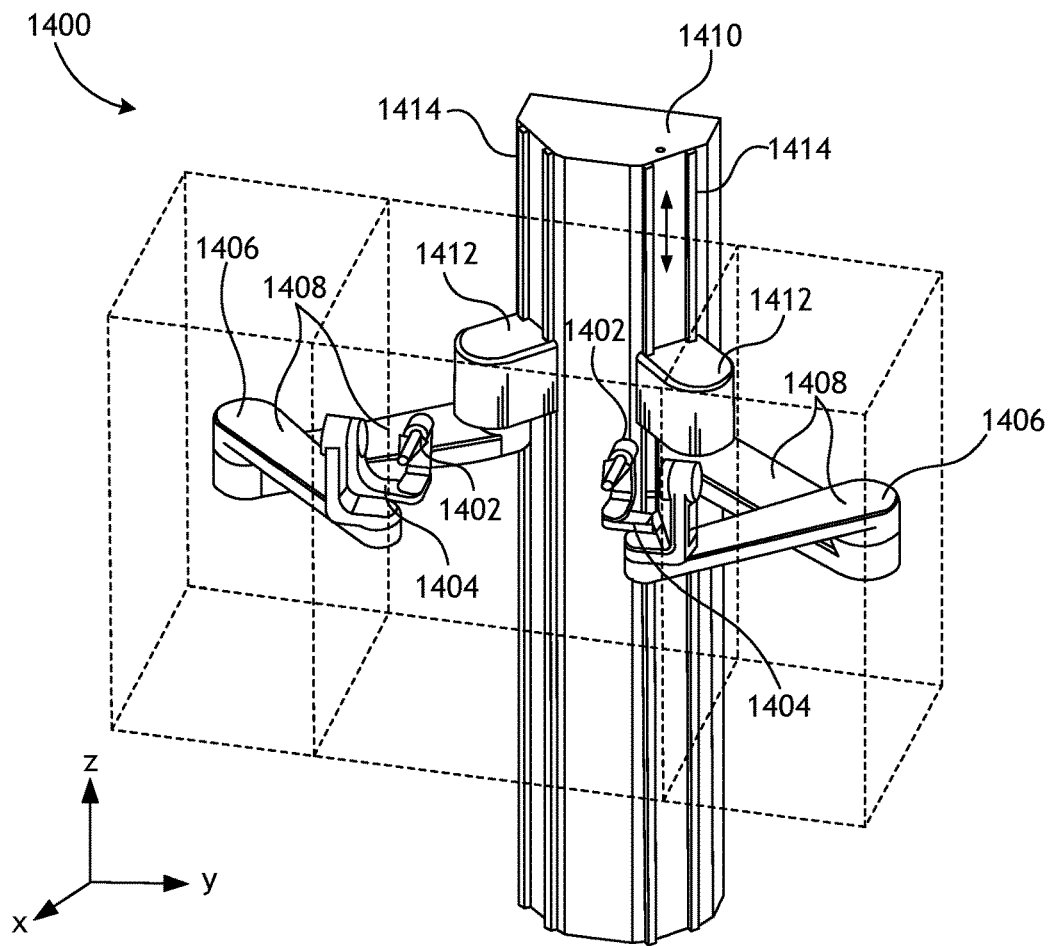
FIG. 14 illustrates an exemplary controller.

FIG. 14 is a perspective view of an embodiment of a controller 1400. In the present embodiment, the controller 1400 comprises a hybrid controller that can have both impedance and admittance control. In other embodiments, the controller 1400 can utilize just impedance or passive control. In other embodiments, the controller 1400 can utilize just admittance control. By being a hybrid controller, the controller 1400 advantageously can have a lower perceived inertia while in use.

In the illustrated embodiment, the controller 1400 is configured to allow manipulation of two medical instruments, and includes two handles 1402. Each of the handles 1402 is connected to a gimbal 1404, and each gimbal 1404 is connected to a positioning platform 1406.

As shown in FIG. 14, each positioning platform 1406 includes a selective compliance assembly robot arm (SCARA) 1408 coupled to a column 1410 by a prismatic joint 1412. The prismatic joints 1412 are configured to translate along the column 1410 (e.g., along rails 1414) to allow each of the handles 1402 to be translated in the z-direction, providing a first degree of freedom. The SCARA arm 1408 is configured to allow motion of the handle 1402 in an x-y plane, providing two additional degrees of freedom.

In some embodiments, one or more load cells are positioned in the controller 1400. For example, in some embodiments, a load cell (not shown) is positioned in the body of each of the gimbals 1404. By providing a load cell, portions of the controller 1400 are capable of operating under admittance control, thereby advantageously reducing the perceived inertia of the controller 1400 while in use. In some embodiments, the positioning platform 1406 is configured for admittance control, while the gimbal 1404 is configured for impedance control. In other embodiments, the gimbal 1404 is configured for admittance control, while the positioning platform 1406 is configured for impedance control. Accordingly, for some embodiments, the translational or positional degrees of freedom of the positioning platform 1406 can rely on admittance control, while the rotational degrees of freedom of the gimbal 1404 rely on impedance control.

F. Navigation and Control.

Traditional endoscopy may involve the use of fluoroscopy (e.g., as may be delivered through a C-arm) and other forms of radiation-based imaging modalities to provide endoluminal guidance to an operator physician. In contrast, the robotic systems contemplated by this disclosure can provide for non-radiation-based navigational and localization means to reduce physician exposure to radiation and reduce the amount of equipment within the operating room. As used herein, the term "localization" may refer to determining and/or monitoring the position of objects in a reference coordinate system. Technologies such as pre-operative mapping, computer vision, real-time EM tracking, and robot command data may be used individually or in combination to achieve a radiation-free operating environment. In other cases, where radiation-based imaging modalities are still used, the pre-operative mapping, computer vision, real-time EM tracking, and robot command data may be used individually or in combination to improve upon the information obtained solely through radiation-based imaging modalities.

Figure 15:
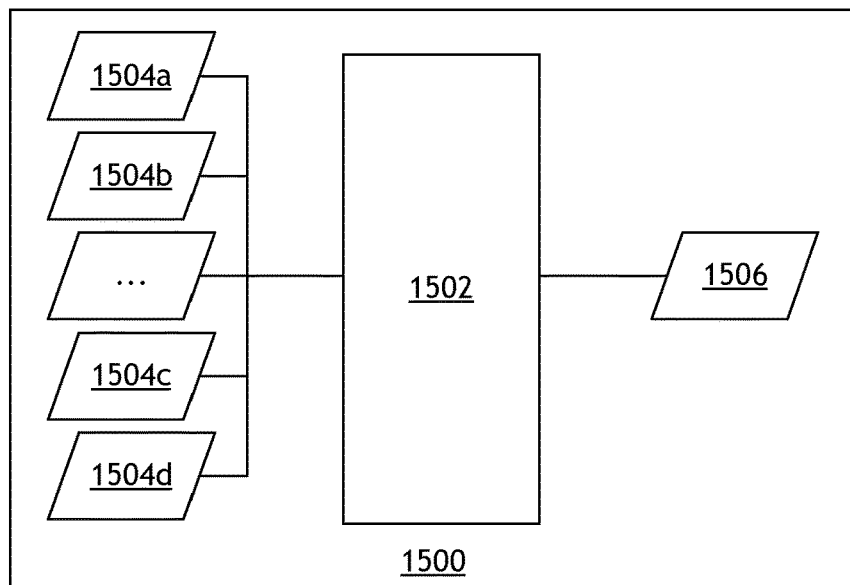
FIG. 15 depicts a block diagram illustrating a localization system that estimates a location of one or more elements of the robotic systems of FIGS. 1-7C, such as the location of the instrument of FIGS. 11-13, in accordance to an example embodiment.

FIG. 15 is a block diagram illustrating a localization system 1500 that estimates a location of one or more elements of the robotic system, such as the location of the instrument, in accordance to an example embodiment. The localization system 1500 may be a set of one or more computer devices configured to execute one or more instructions. The computer devices may be embodied by a processor (or processors) and computer-readable memory in one or more components discussed above. By way of example and not limitation, the computer devices may be in the tower 112 shown in FIG. 1, the cart 102 shown in FIGS. 1-3B, the beds shown in FIGS. 4-9, etc.

As shown in FIG. 15, the localization system 1500 may include a localization module 1502 that processes input data 1504a, 1504b, 1504c, and 1504d to generate location data 1506 for the distal tip of a medical instrument. The location data 1506 may be data or logic that represents a location and/or orientation of the distal end of the instrument relative to a frame of reference. The frame of reference can be a frame of reference relative to the anatomy of the patient or to a known object, such as an EM field generator (see discussion below for the EM field generator).

The various input data 1504a-d are now described in greater detail. Pre-operative mapping may be accomplished through the use of the collection of low dose CT scans. Pre-operative CT scans are reconstructed into three-dimensional images, which are visualized, e.g. as "slices" of a cutaway view of the patient's internal anatomy. When analyzed in the aggregate, image-based models for anatomical cavities, spaces and structures of the patient's anatomy, such as a patient lung network, may be generated. Techniques such as center-line geometry may be determined and approximated from the CT images to develop a three-dimensional volume of the patient's anatomy, referred to as model data 1504a (also referred to as "preoperative model data" when generated using only preoperative CT scans). The use of center-line geometry is discussed in U.S. patent application Ser. No. 14/523,760, the contents of which are herein incorporated in its entirety. Network topological models may also be derived from the CT-images, and are particularly appropriate for bronchoscopy.

In some embodiments, the instrument may be equipped with a camera to provide vision data 1504b. The localization module 1502 may process the vision data 1504b to enable one or more vision-based location tracking. For example, the preoperative model data may be used in conjunction with the vision data 1504b to enable computer vision-based tracking of the medical instrument (e.g., an endoscope or an instrument advance through a working channel of the endoscope). For example, using the preoperative model data 1504a, the robotic system may generate a library of expected endoscopic images from the model based on the expected path of travel of the endoscope, each image linked to a location within the model. Intra-operatively, this library may be referenced by the robotic system in order to compare real-time images captured at the camera (e.g., a camera at a distal end of the endoscope) to those in the image library to assist localization.

Other computer vision-based tracking techniques use feature tracking to determine motion of the camera, and thus the endoscope. Some features of the localization module 1502 may identify circular geometries in the preoperative model data 1504a that correspond to anatomical lumens and track the change of those geometries to determine which anatomical lumen was selected, as well as the relative rotational and/or translational motion of the camera. Use of a topological map may further enhance vision-based algorithms or techniques.

Optical flow, another computer vision-based technique, may analyze the displacement and translation of image pixels in a video sequence in the vision data 1504b to infer camera movement. Examples of optical flow techniques may include motion detection, object segmentation calculations, luminance, motion compensated encoding, stereo disparity measurement, etc. Through the comparison of multiple frames over multiple iterations, movement and location of the camera (and thus the endoscope) may be determined.

The localization module 1502 may use real-time EM tracking to generate a real-time location of the endoscope in a global coordinate system that may be registered to the patient's anatomy, represented by the preoperative model. In EM tracking, an EM sensor (or tracker) comprising of one or more sensor coils embedded in one or more locations and orientations in a medical instrument (e.g., an endoscopic tool) measures the variation in the EM field created by one or more static EM field generators positioned at a known location. The location information detected by the EM sensors is stored as EM data 1504c. The EM field generator (or transmitter), may be placed close to the patient to create a low intensity magnetic field that the embedded sensor may detect. The magnetic field induces small currents in the sensor coils of the EM sensor, which may be analyzed to determine the distance and angle between the EM sensor and the EM field generator. These distances and orientations may be intra-operatively "registered" to the patient anatomy (e.g., the preoperative model) in order to determine the geometric transformation that aligns a single location in the coordinate system with a position in the pre-operative model of the patient's anatomy. Once registered, an embedded EM tracker in one or more positions of the medical instrument (e.g., the distal tip of an endoscope) may provide real-time indications of the progression of the medical instrument through the patient's anatomy.

Robotic command and kinematics data 1504d may also be used by the localization module 1502 to provide localization data 1506 for the robotic system. Device pitch and yaw resulting from articulation commands may be determined during pre-operative calibration. Intra-operatively, these calibration measurements may be used in combination with known insertion depth information to estimate the position of the instrument. Alternatively, these calculations may be analyzed in combination with EM, vision, and/or topological modeling to estimate the position of the medical instrument within the network.

As FIG. 15 shows, a number of other input data can be used by the localization module 1502. For example, although not shown in FIG. 15, an instrument utilizing shape-sensing fiber can provide shape data that the localization module 1502 can use to determine the location and shape of the instrument.

The localization module 1502 may use the input data 1504a-d in combination(s). In some cases, such a combination may use a probabilistic approach where the localization module 1502 assigns a confidence weight to the location determined from each of the input data 1504a-d. Thus, where the EM data 1504c may not be reliable (as may be the case where there is EM interference) the confidence of the location determined by the EM data 1504c can be decrease and the localization module 1502 may rely more heavily on the vision data 1504b and/or the robotic command and kinematics data 1504d.

As discussed above, the robotic systems discussed herein may be designed to incorporate a combination of one or more of the technologies above. The robotic system's computer-based control system, based in the tower, bed and/or cart, may store computer program instructions, for example, within a non-transitory computer-readable storage medium such as a persistent magnetic storage drive, solid state drive, or the like, that, upon execution, cause the system to receive and analyze sensor data and user commands, generate control signals throughout the system, and display the navigational and localization data, such as the position of the instrument within the global coordinate system, anatomical map, etc.

2. Introduction.

Embodiments of the disclosure relate to systems and techniques for assembling a surgical tool by removably coupling a portion of the surgical tool to a stage portion of the surgical tool and replacing the portion of the surgical tool with another portion of the surgical tool that is removably coupleable to the stage portion. The method includes providing a handle having a first end, a second end, and a lead screw and at least one spline extendable between the first and second ends. The method may further include rotating the lead screw in a first direction and thereby translating an elevator layer of a carriage proximally along a longitudinal axis of the handle, wherein the elevator layer is movably mounted to the lead screw at a carriage nut, removably coupling one or more additional layers of the carriage to the elevator layer, wherein an elongate shaft extends distally from the one or more additional layers and an end effector is arranged at a distal end of the elongate shaft, penetrating the elevator layer with the end effector and the elongate shaft upon coupling the one or more additional layers to the elevator layer, and rotating the lead screw in a second direction opposite the first direction and thereby translating the carriage distally along the longitudinal axis.

Embodiments of the present disclosure may also relate to alternate methods of assembling a surgical tool. The alternate method includes removing an end cap from a stage portion of the surgical tool, where the stage portion includes a handle having a first end and a second end, a lead screw and at least one spline extendable between the first and second ends, and an elevator layer of a carriage movably mounted to the lead screw and the at least one spline. The method may also include advancing the carriage to the second end and detaching a first instrument portion from the stage portion, where the first instrument portion includes one or more first additional layers removably coupled to the elevator layer, and a first elongate shaft extending distally from the one or more first additional layers and having a first end effector arranged at a distal end of the first shaft. The method may also include replacing the first instrument portion with a second instrument portion coupled to the stage portion, where the second instrument portion includes one or more second additional layers removably coupleable to the elevator layer, and a second elongate shaft extending distally from the one or more second additional layers and having a second end effector arranged at a distal end of the second shaft.

3. Description.

Figure 16:
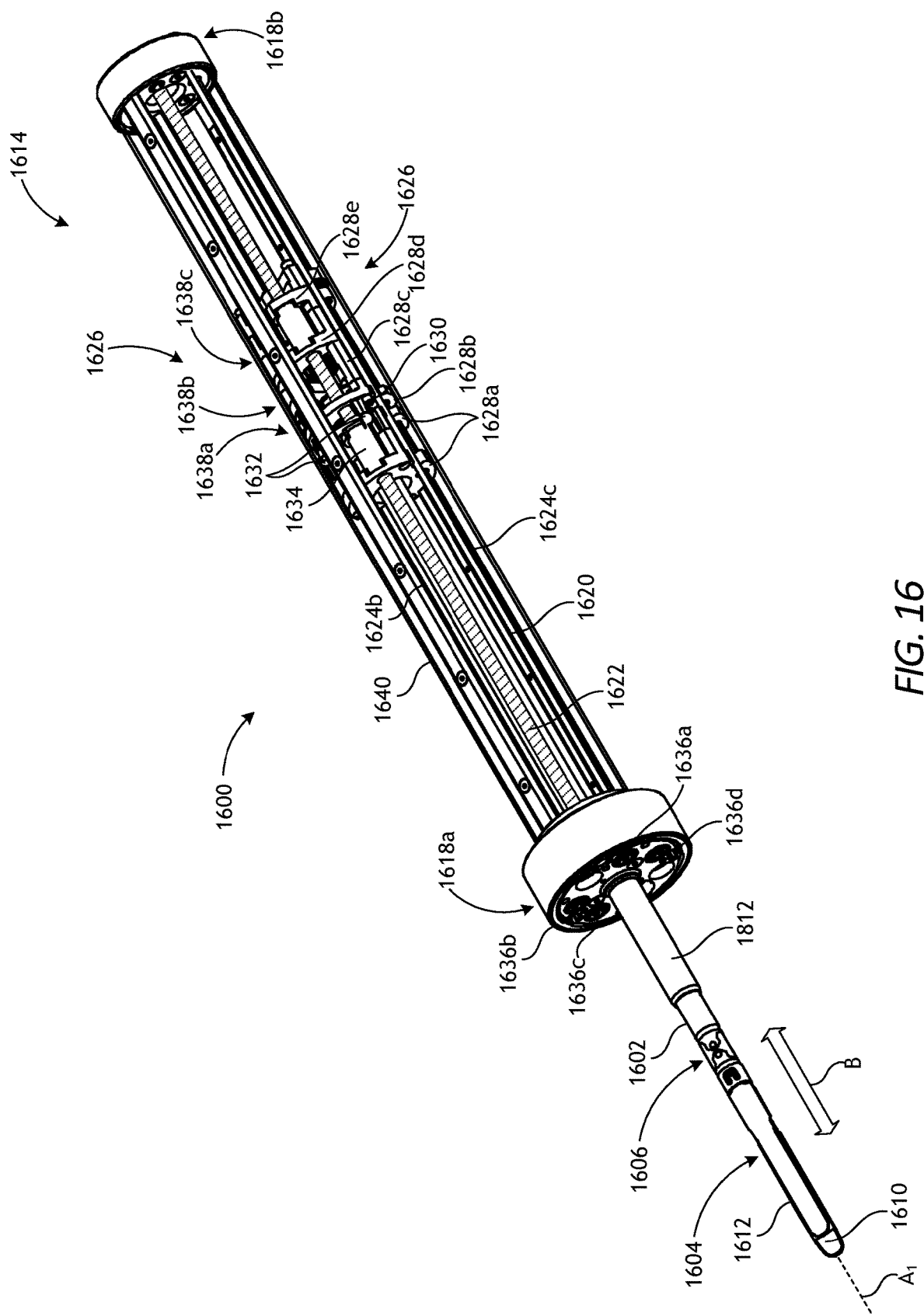
FIG. 16 is an isometric side view of an example surgical tool that may incorporate some or all of the principles of the present disclosure.

FIG. 16 is an isometric side view of an example surgical tool 1600 that may incorporate some or all of the principles of the present disclosure. The surgical tool 1600 may be similar in some respects to any of the medical instruments described above with reference to FIGS. 11-13 and, therefore, may be used in conjunction with a robotic surgical system, such as the robotically-enabled systems 100, 400, and 900 of FIGS. 1-13. As illustrated, the surgical tool 1600 includes an elongated shaft 1602, an end effector 1604 arranged at the distal end of the shaft 1602, and an articulable wrist 1606 (alternately referred to as a "wrist joint") that couples the end effector 1604 to the distal end of the shaft 1602.

The terms "proximal" and "distal" are defined herein relative to a robotic surgical system having an interface configured to mechanically and electrically couple the surgical tool 1600 to a robotic manipulator. The term "proximal" refers to the position of an element closer to the robotic manipulator and the term "distal" refers to the position of an element closer to the end effector 1604 and thus closer to the patient during operation. Moreover, the use of directional terms such as above, below, upper, lower, upward, downward, left, right, and the like are used in relation to the illustrative embodiments as they are depicted in the figures, the upward or upper direction being toward the top of the corresponding figure and the downward or lower direction being toward the bottom of the corresponding figure.

The surgical tool 1600 can have any of a variety of configurations capable of performing one or more surgical functions. In the illustrated embodiment, the end effector 1604 comprises a surgical stapler, alternately referred to as an "endocutter," configured to cut and staple (fasten) tissue. As illustrated, the end effector 1604 includes opposing jaws 1610, 1612 configured to move (articulate) between open and closed positions. Alternatively, the end effector 1604 may comprise other types of instruments having the opposing jaws 1610, 1612 such as, but not limited to, tissue graspers, surgical scissors, advanced energy vessel sealers, clip appliers, needle drivers, a babcock including a pair of opposed grasping jaws, bipolar jaws (e.g., bipolar Maryland grasper, forceps, a fenestrated grasper, etc.), etc. In other embodiments, the end effector 1604 may instead comprise any end effector or instrument capable of being operated in conjunction with the presently disclosed robotic surgical systems and methods. Such end effectors or instruments include, but are not limited to, a suction irrigator, an endoscope (e.g., a camera), or any combination thereof.

One or both of the jaws 1610, 1612 may be configured to pivot to actuate the end effector 1604 between open and closed positions. In the illustrated example, the second jaw 1612 is rotatable (pivotable) relative to the first jaw 1610 to move between an open, unclamped position and a closed, clamped position. In other embodiments, however, the first jaw 1610 may move (rotate) relative to the second jaw 1612, without departing from the scope of the disclosure. In yet other embodiments, both jaws 1610, 1612 may move to actuate the end effector 1604 between open and closed positions.

In the illustrated example, the first jaw 1610 may be characterized or otherwise referred to as a "cartridge" or "channel" jaw, and the second jaw 1612 may be characterized or otherwise referred to as an "anvil" jaw. The first jaw 1610 may include a frame that houses or supports a staple cartridge, and the second jaw 1612 is pivotally supported relative to the first jaw 1610 and defines a surface that operates as an anvil to deform staples ejected from the staple cartridge during operation.

The wrist 1606 enables the end effector 1604 to articulate (pivot) relative to the shaft 1602 and thereby position the end effector 1604 at various desired orientations and locations relative to a surgical site. In the illustrated embodiment, the wrist 1606 is designed to allow the end effector 1604 to pivot (swivel) left and right relative to a longitudinal axis $A_1$ of the shaft 1602. In other embodiments, however, the wrist 1606 may be designed to provide multiple degrees of freedom, including one or more translational variables (i.e., surge, heave, and sway) and/or one or more rotational variables (i.e., Euler angles or roll, pitch, and yaw). The translational and rotational variables describe the position and orientation of a component of a surgical system (e.g., the end effector 1604) with respect to a given reference Cartesian frame. "Surge" refers to forward and backward translational movement, "heave" refers to translational movement up and down, and "sway" refers to translational movement left and right. With regard to the rotational terms, "roll" refers to tilting side to side, "pitch" refers to tilting forward and backward, and "yaw" refers to turning left and right.

In the illustrated embodiment, the pivoting motion at the wrist 1606 is limited to movement in a single plane, e.g., only yaw movement relative to the longitudinal axis $A_1$. The end effector 1604 is depicted in FIG. 16 in the unarticulated position where a longitudinal axis of the end effector 1604 is substantially aligned with the longitudinal axis $A_1$ of the shaft 1602, such that the end effector 1604 is at a substantially zero angle relative to the shaft 1602. In the articulated position, the longitudinal axis of the end effector 1604 would be angularly offset from the longitudinal axis $A_1$ such that the end effector 1604 would be oriented at a non-zero angle relative to the shaft 1602.

Still referring to FIG. 16, the surgical tool 1600 may include a drive housing or "handle" 1614 that operates as an actuation system designed to facilitate articulation of the wrist 1606 and actuation (operation) of the end effector 1604 (e.g., clamping, firing, rotation, articulation, energy delivery, etc.). As described in more detail below, the handle 1614 includes coupling features that releasably couple the surgical tool 1600 to an instrument driver of a robotic surgical system.

The handle 1614 includes a plurality of drive members (obscured in FIG. 16) that extend to the wrist 1606 and the end effector 1604. Selective actuation of some drive members causes the end effector 1604 to articulate (pivot) relative to the shaft 1602 at the wrist 1606. Selective actuation of other drive members cause the end effector 1604 to actuate (operate). Actuating the end effector 1604 may include closing and/or opening the second jaw 1612 relative to the first jaw 1610 (or vice versa), thereby enabling the end effector 1604 to grasp (clamp) onto tissue. Once tissue is grasped or clamped between the opposing jaws 1610, 1612, actuating the end effector 1604 may further include "firing" the end effector 1604, which may refer to causing a cutting element or knife (not visible) to advance distally within a slot (obscured from view) defined in the first jaw 1610. As it moves distally, the cutting element transects any tissue grasped between the opposing jaws 1610, 1612. Moreover, as the cutting element advances distally, a plurality of staples contained within the staple cartridge (e.g., housed within the first jaw 1610) are urged (cammed) into deforming contact with corresponding anvil surfaces (e.g., pockets) provided on the second jaw 1612. The deployed staples may form multiple rows of staples that seal opposing sides of the transected tissue.

As illustrated, the handle 1614 has a first or "distal" end 1618*a* and a second or "proximal" end 1618*b* opposite the first end 1618*a*. In some embodiments, one or more struts 1620 (two shown) extend longitudinally between the first and second ends 1618*a,b* to help fix the distance between the first and second ends 1618*a,b*, provide structural stability to the handle 1614, and secure the first end 1618*a* to the second end 1618*b*. In other embodiments, however, the struts 1620 may be omitted, without departing from the scope of the disclosure.

A lead screw 1622 and one or more splines 1624 also extend longitudinally between the first and second ends 1618*a,b*. In the illustrated embodiment, the handle 1614 includes a first spline 1624*a*, a second spline 1624*b*, and a third spline 1624*c*. While three splines 1624*a-c* are depicted, more or less than three may be included in the handle 1614, without departing from the scope of the disclosure. Unlike the struts 1620, the lead screw 1622 and the splines 1624*a-c* are rotatably mounted to the first and second ends 1618*a,b*. As described in more detail below, selective rotation of the lead screw 1622 and the splines 1624*a-c* causes actuation of various components within the handle 1614, which thereby causes various functions of the surgical tool 1600 to transpire, for example, such as translating the end effector 1604 along the longitudinal axis $A_1$, causing the end effector 1604 to articulate (pivot) at the wrist 1606, and causing the end effector 1604 to actuate (operate).

The handle 1614 further includes a carriage or kart 1626 movably mounted along the lead screw 1622 and the splines 1624*a-c* and housing various activating mechanisms configured to cause operation of specific functions of the end effector 1604. The carriage 1626 may comprise two or more layers, shown in FIG. 16 as a first layer 1628*a*, a second layer 1628*b*, a third layer 1628*c*, a fourth layer 1628*d*, and a fifth layer 1628*e*. While five layers 1628*a-e* are depicted, more or less than five may be included in the carriage 1626, without departing from the scope of the disclosure.

In addition, one or more of the layers 1628*a-e* of the carriage 1626 may be detachable relative to the remaining layers 1628*a-e*. In this manner, one or more of the layers 1628*a-e* of the carriage 1626 may be secured together as a block of layers that may be releasably secured to the remaining layer(s) to define the carriage 1628. For example, some of the layers 1628*a-e* may be integrally secured together in series, to form a block of layers, and such block of layers may be selectively secured to the remaining one or more layers 1628*a-e* that are not integrally secured to the block of layers. In the illustrated embodiment, the layers 1628*b-e* are secured to each other in series using one or more mechanical fasteners 1630 (one visible) extending between the second layer 1628*b* and the fifth layer 1628*e* and through coaxially aligned holes in each layer 1628*b-e* to form a block of layers configured to be releasably secured to the first layer 1628*a*, as described below. In the illustrated example, one or more snaps 1632 (two visible) are utilized to align (or clock) and releasably attach the block of layers 1628*b-e* to the first layer 1628*a*, as further described below, but various other types of one or more releasable connector(s) may be utilized.

While four layers 1628*b-e* are depicted as being secured together via the mechanical fastener(s) 1630 to define the block of secured-together layers 1628*b-e* releasably attached to the first layer 1628*a* via the snaps 1632, the block of secured-together layers may include more or less than four layers, without departing from the scope of the disclosure. Moreover, one or more additional layers may be mechanically fastened in series to the first layer 1628*a* (e.g., the second layer 1628*b*) to define a second block of secured-together layers that is releasably attached to the first block of secured-together layers (e.g., the three layers 1628*c-e*), without departing from the scope of the disclosure. As further described below, configuring the carriage 1626 with one or more layers that are releasably secured relative to the remaining layers will provide a degree of modularity to the surgical tool 1600 to thereby allow one or more components of the surgical tool 1600 to be interchangeable, reusable, and/or replaceable.

The shaft 1602 is coupled to and extends distally from the carriage 1626 through the first end 1618*a* of the handle 1614. In the illustrated embodiment, for example, the shaft 1602 penetrates the first end 1618*a* at a central aperture defined through the first end 1618*a*. The carriage 1626 is movable between the first and second ends 1618*a,b* along the longitudinal axis $A_1$ and is thereby able to advance or retract the end effector 1604 relative to the handle 1614, as indicated by the arrows B. More specifically, in some embodiments, the carriage 1626 includes a carriage nut 1634 mounted to the lead screw 1622 and secured with respect to the first layer 1628*a*. In this manner, the first layer 1628*a* of the carriage 1626 may define an elevator upon which the other layers 1628*b-e* releasably attached thereon may be translated, as described below. The outer surface of the lead screw 1622 defines helical threading and the carriage nut 1634 defines corresponding internal helical threading (not shown) matable with the outer helical threading of the lead screw 1622. As a result, rotation of the lead screw 1622 causes the carriage nut 1634 to advance or retract the carriage 1626 along the longitudinal axis $A_1$ and correspondingly advance or retract the end effector 1604 relative to the handle 1614.

As indicated above, the lead screw 1622 and the splines 1624*a-c* are rotatably mounted to the first and second ends 1618*a,b*. More specifically, the first end 1618*a* of the handle 1614 may include one or more rotatable drive inputs, shown as a first drive input 1636*a*, a second drive input 1636*b*, a third drive input 1636*c*, and a fourth drive input 1636*d*. As discussed in more detail below, each drive input 1636*a-d* may be matable with a corresponding drive output of an instrument driver such that movement (rotation) of a given drive output correspondingly moves (rotates) the associated drive input 1636a-d.

The first drive input 1636a may be operatively coupled to the lead screw 1622 such that rotation of the first drive input 1636a correspondingly rotates the lead screw 1622, which causes the carriage nut 1634 and the first layer 1628a constraining the carriage nut 1634 to advance or retract along the longitudinal axis $A_1$, depending on the rotational direction of the lead screw 1622. Moreover, as described herein the first layer 1628a of the carriage 1626 may be configured as an elevator (of the carriage 1626) that translates the remaining layers 1628b-e of the carriage 1626 releasably connected to the first layer 1628a. Thus, when the remaining layers 1628b-e are installed on the first layer 1628a, to thereby define the carriage 1626 as depicted in FIG. 16, rotation of the first drive input 1636a correspondingly rotates the lead screw 1622, which causes the entirety of the carriage 1626 now fully coupled to the carriage nut 1634, to advance or retract along the longitudinal axis $A_1$, depending on the rotational direction of the lead screw 1622.

The second drive input 1636b may be operatively coupled to the first spline 1624a such that rotation of the second drive input 1636b correspondingly rotates the first spline 1624a. In some embodiments, the first spline 1624a may be operatively coupled to a first activating mechanism 1638a of the carriage 1626, and the first activating mechanism 1638a may be operable to open and close the jaws 1610, 1612. Accordingly, rotating the second drive input 1636b will correspondingly actuate the first activating mechanism 1638a and open or close the jaws 1610, 1612, depending on the rotational direction of the first spline 1624a. In addition, the second layer 1628b is configured to accommodate the first activating mechanism 1638a such that the jaws 1610, 1612 are operable as described herein and, in the illustrated example, the first activating mechanism 1638a is at least partially constrained by the second layer 1628b and the third layer 1628c.

The third drive input 1636c may be operatively coupled to the second spline 1624b such that rotation of the third drive input 1636c correspondingly rotates the second spline 1624b. In some embodiments, the second spline 1624b may be operatively coupled to a second activating mechanism 1638b of the carriage 1626, and the second activating mechanism 1638b may be operable to articulate the end effector 1604 at the wrist 1606. Accordingly, rotating the third drive input 1636c will correspondingly actuate the second activating mechanism 1638b and cause the wrist 1606 to articulate in at least one degree of freedom, depending on the rotational direction of the second spline 1624b. In addition, the third layer 1628c is configured to accommodate the second activating mechanism 1638b for articulation of the wrist 1606 as described herein and, in the illustrated example, the second activating mechanism 1638b is at least partially constrained by the third layer 1628c and the fourth layer 1628d.

The fourth drive input 1636d may be operatively coupled to the third spline 1624c such that rotation of the fourth drive input 1636d correspondingly rotates the third spline 1624c. In some embodiments, the third spline 1624c may be operatively coupled to a third activating mechanism 1638c of the carriage 1626, and the third activating mechanism 1638c may be operable to fire the cutting element (knife) at the end effector 1604. Accordingly, rotating the fourth drive input 1636d will correspondingly actuate the third activating mechanism 1638c and cause the knife to advance or retract, depending on the rotational direction of the third spline 1624c. In addition, the fifth layer 1628e is configured to accommodate the third activating mechanism 1638c for firing the cutting element of the end effector 1604 as described herein and, in the illustrated example, the third activating mechanism 1638c is at least partially constrained by the fifth layer 1628e and a thrust bearing layer 1628f of the carriage 1626.

In the illustrated embodiment, the activating mechanisms 1638a-c comprise intermeshed gearing assemblies including one or more drive gears driven by rotation of the corresponding spline 1624a-c and configured to drive one or more corresponding driven gears that cause operation of specific functions of the end effector 1604.

FIG. 16 illustrates an embodiment of the handle 1614 having a shroud 1640 that defines a periphery of the handle 1614 for handling and manipulation by the operator or user. In the illustrated embodiment, the shroud 1640 is depicted as a transparent material (or at least a partially transparent material), such that the internal components of the handle 1614 are visible through the shroud 1640. However, in other examples, the shroud 1640 need not be transparent. Where included, the shroud 1640 may be sized to receive the lead screw 1622, the splines 1624a-c, and the carriage 1626, as well as other internal components of the handle 1614.

Figure 17:
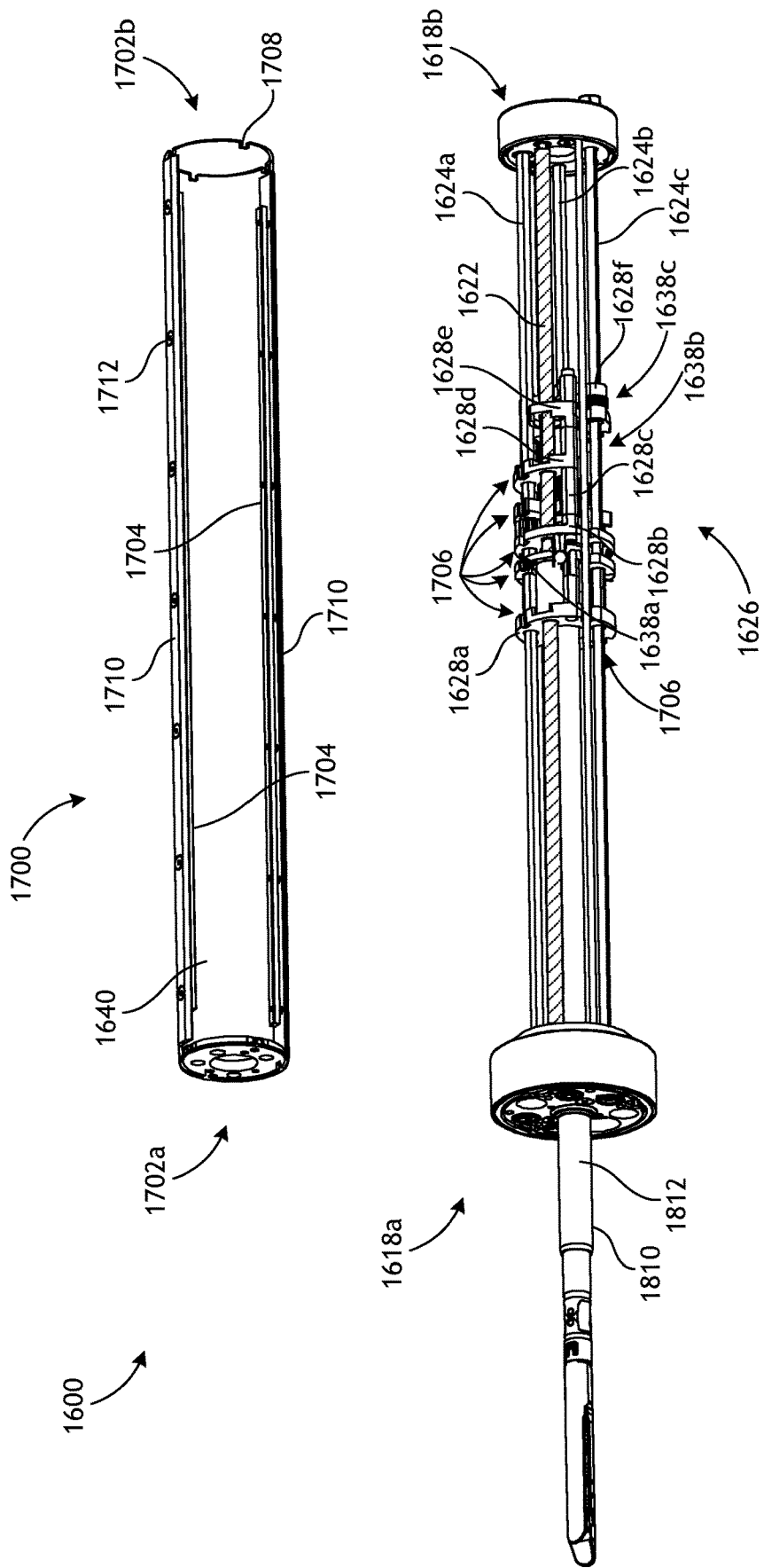
FIG. 17 is an isometric view of the surgical tool of FIG. 16 when unassembled from its shroud assembly, according to one or more embodiments.

In some embodiments, the shroud 1640 may be incorporated in a shroud assembly of the handle 1614. FIG. 17 is an isometric view of the surgical tool 1600 of FIG. 16 illustrating the handle 1614 when partially disassembled, according to one or more embodiments. In particular, FIG. 17 depicts an exemplary shroud assembly 1700 of the handle 1614 incorporating the shroud 1640 when disassembled from the remaining portion of the handle 1614, according to one or more embodiments. In the illustrated embodiment, the shroud assembly 1700 defines a tubular or cylindrical structure having (i) a first end 1702a matable with the first end 1618a of the handle 1614 and (ii) a second end 1702b opposite the first end 1702a and matable with the second end 1618b of the handle 1614. The carriage 1626, the lead screw 1622, and the splines 1624a-c may all be accommodated within the interior of the shroud 1640, and the carriage 1626 may engage and ride on one or more rails 1704 (sometimes referred to as guide rails) coupled to the shroud 1640. The rails 1704 extend longitudinally and parallel to the lead screw 1622, and the rails 1704 are sized to be received within corresponding notches 1706 defined on the outer periphery of the carriage 1626 and, more particularly, on one or more of the layers 1628a-e. As the carriage 1626 translates along the longitudinal axis $A_1$, the rails 1704 help maintain the angular position of the carriage 1626 and assume any torsional loading that would otherwise adversely affect the carriage 1626. In addition, the shroud 1640 may include one or more alignment notches 1708 for aligning the second end 1618b on the shroud assembly 1700. The rails 1704 may be fastened within an interior of the shroud 1640 and, in the illustrated examples, are coupled within the interior of the shroud 1640 via exterior rails 1710 positioned exterior the shroud 1640 and connected to the (guide) rails 1704 via a plurality of fasteners 1712 that extend through the shroud 1640.

Figure 18A:
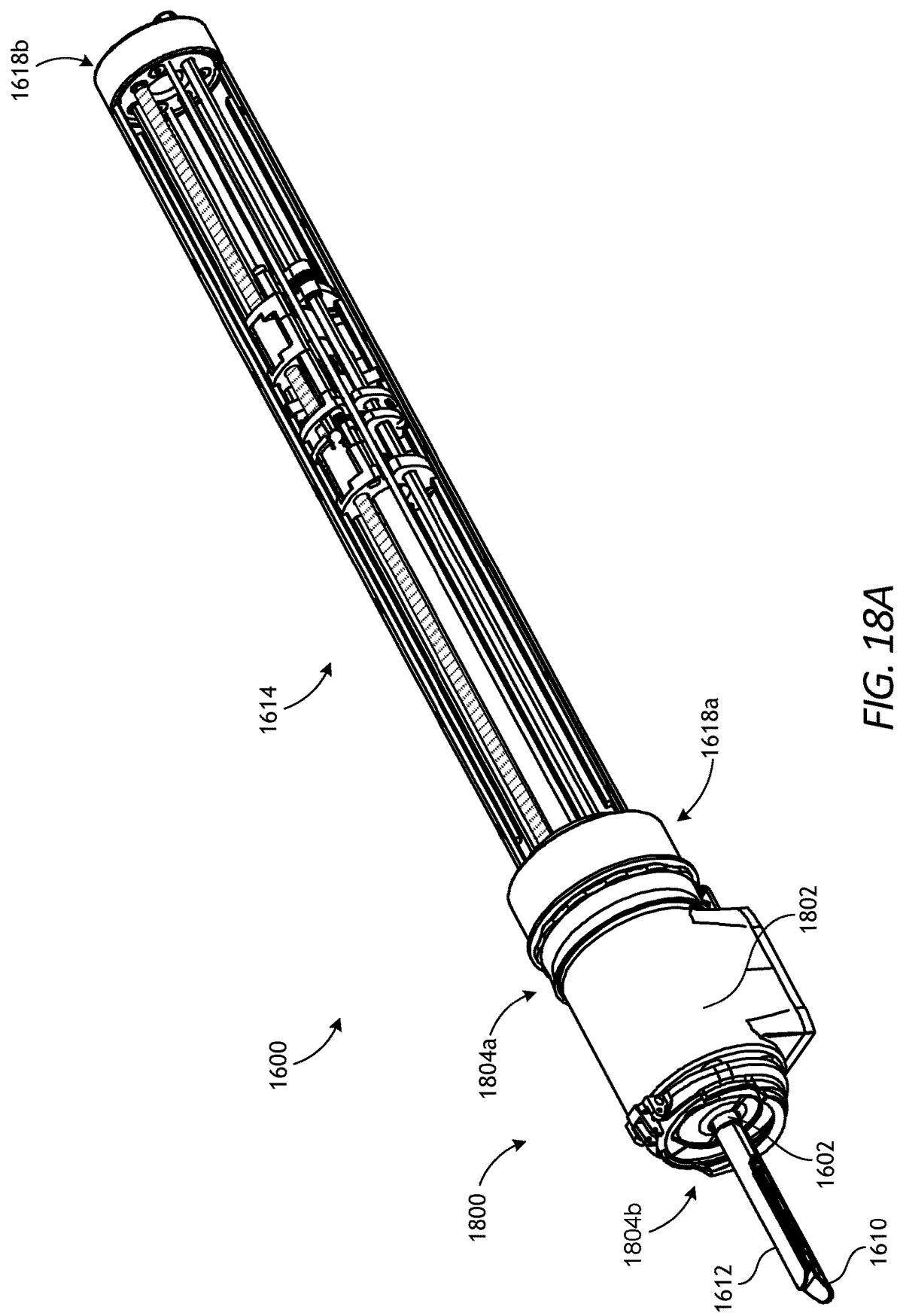
FIG. 18A is an isometric view of the tool of FIGS. 16-17 releasably coupled to an example instrument driver, according to one or more embodiments.

FIG. 18A is an isometric view of the surgical tool 1600 of FIGS. 16 and 17 releasably coupled to an example instrument driver 1800, according to one or more embodiments. The instrument driver 1800 may be similar in some respects to the instrument drivers 1102, 1200 of FIGS. 11 and 12, respectively, and therefore may be best understood with reference thereto. Similar to the instrument drivers 1102, 1200, for example, the instrument driver 1800 may be mounted to or otherwise positioned at the end of a robotic arm (not shown) and designed to provide the motive forces required to operate the surgical tool 1600. Unlike the instrument drivers 1102, 1200, however, the shaft 1602 of the surgical tool 1600 extends through and penetrates the instrument driver 1800.

The instrument driver 1800 has a body 1802 having a first or "proximal" end 1804a and a second or "distal" end 1804b opposite the first end 1804a. In the illustrated embodiment, the first end 1804a of the instrument driver 1800 is matable with the first end 1618a of the handle 1614, and the shaft 1602 of the surgical tool 1600 extends into the first end 1804a, through the body 1802, and distally from the second end 1804b of the body 1802.

Figure 18B:
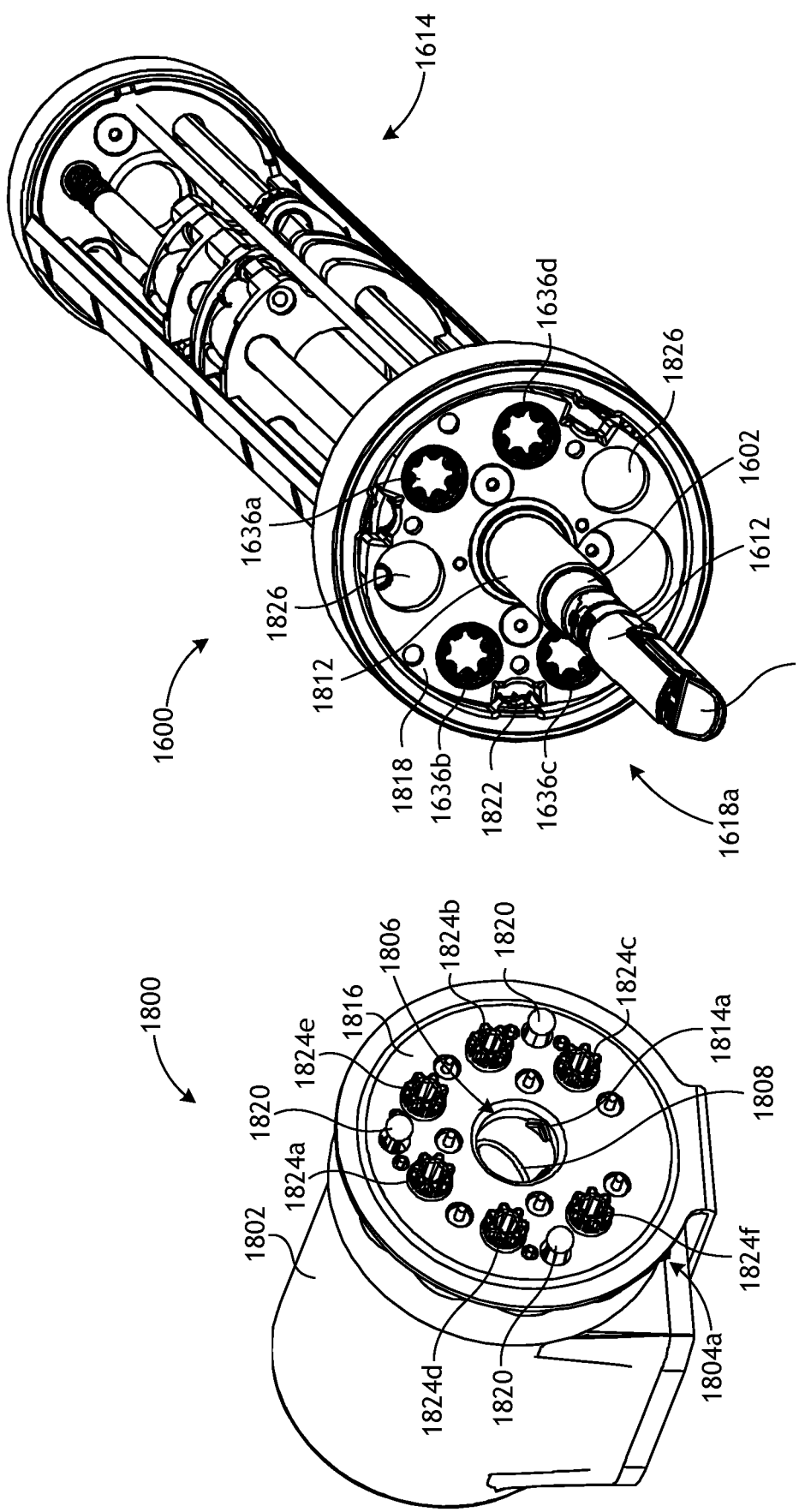
FIG. 18B provides separated isometric end views of the instrument driver of FIG. 18A and the surgical tool of FIGS. 16-17.

FIG. 18B provides separated isometric end views of the first end 1804a of the instrument driver 1800 and the first end 1618a of the handle 1614 of the surgical tool 1600 of FIGS. 16 and 17. With the jaws 1610, 1612 closed, the shaft 1602 and the end effector 1604 are designed to penetrate the instrument driver 1800 by extending through a central aperture 1806 defined longitudinally through the body 1802 between the first and second ends 1804a,b. To angularly align the surgical tool 1600 with the instrument driver 1800 in a proper angular orientation, one or more alignment guides 1808 may be provided or otherwise defined within the central aperture 1806 and configured to engage one or more corresponding alignment features 1810 provided by the surgical tool 1600 (obscured from view, see FIG. 17). In the illustrated embodiment, the alignment feature 1810 comprises a protrusion or projection defined on or otherwise provided by an alignment nozzle 1812 extending distally from the first end 1618a of the handle 1614. In one or more embodiments, the alignment guide 1808 may comprise a curved or arcuate shoulder configured to receive the alignment feature 1810 as the shaft 1602 enters the central aperture 1806 and guide the surgical tool 1600 to a proper angular alignment with the instrument driver 1800 as the shaft 1602 is advanced distally through the central aperture 1806.

In addition, one or more additional alignment features 1814 may be arranged within the central aperture 1806 and configured to mate with one or more corresponding recesses (not illustrated) provided on the alignment nozzle 1812 for ensuring the surgical tool 1600 is installed at a proper rotational alignment with respect to the instrument driver 1800.

As illustrated, a drive interface 1816 is provided at the first end 1804a of the instrument driver 1800, and a driven interface 1818 is provided at the first end 1618a of the handle 1614. The driver and driven interfaces 1816, 1818 may be configured to mechanically, magnetically, and/or electrically couple the handle 1614 to the instrument driver 1800. To accomplish this, the driver and driven interfaces 1816, 1818 may provide one or more matable locating features configured to secure the handle 1614 to the instrument driver 1800. In the illustrated embodiment, for example, the drive interface 1816 provides one or more interlocking features 1820 (three shown) configured to locate and mate with one or more substantially complimentary shaped pockets 1822 (three shown) provided on the driven interface 1818. The interlocking features 1820, exemplified as bulbous protrusions, may be configured to align and mate with the pockets 1822 via an interference or snap fit engagement, for example.

The instrument driver 1800 also includes one or more drive outputs that extend through the drive interface 1816 to mate with the drive inputs 1636a-d provided on the driven face 1818 at the first end 1618a of the handle 1614. More specifically, in the illustrated embodiment, the drive interface 1816 of the instrument driver 1800 includes a first drive output 1824a matable with the first drive input 1636a, a second drive output 1824b matable with the second drive input 1636b, a third drive output 1824c matable with the third drive input 1636c, and a fourth drive output 1824d matable with the fourth drive input 1636d. In some embodiments, as illustrated, the drive outputs 1824a-d may comprise splines designed to mate with corresponding splined receptacles on the drive inputs 1636a-d. Once properly mated, the drive inputs 1636a-d will share axes of rotation with the corresponding drive outputs 1824a-d to allow the transfer of rotational torque from the drive outputs 1824a-d to the corresponding drive inputs 1636a-d. In some embodiments, each drive output 1824a-d may be spring loaded and otherwise biased to spring outwards away from the drive interface 1816. Each drive output 1824a-d may be capable of partially or fully retracting into the drive interface 1816.

In some embodiments, the instrument driver 1800 may include additional drive outputs, depicted in FIG. 18B as a fifth drive output 1824e and a sixth drive output 1824f. The fifth and sixth drive outputs 1824e,f may be configured and positioned to mate with additional drive inputs (not shown) of the handle 1614 to help undertake one or more additional functions of the surgical tool. In the illustrated embodiment, the handle 1614 does not include additional drive inputs, and the driven interface 1818 defines corresponding pockets 1826 configured to receive the fifth and sixth drive outputs 1824e,f.

Removable Carriage Layers on Translating System

The surgical tool 1600 may be modular such that certain features of the surgical tool 1600 may be removed and replaced. In this manner, a portion of the surgical tool 1600 may be reusable for multiple surgical procedures, and thereby reduce capital expenditure. For example, the shaft 1602, the articulable wrist 1606, and the end effector 1604 may be releasably coupled within the handle 1614 to be operable during a medical procedure and then removed from the handle 1614 following the procedure and replaced. In these embodiments, the layers of the carriage 1626 associated with various functions of the shaft 1602, the articulable wrist 1606, and the end effector 1604, together with their associated activating mechanisms, may be assembled as one or more separate components that may be removably secured within the handle 1614.

In some embodiments, the layers 1628b-e are secured to the shaft 1602 and the activating mechanisms 1638a-c are operatively housed within their associated layer 1628b-e so as to actuate the surgical tool 1600 as described herein. In the illustrated embodiment, the layers 1628b-e are fastened together with the mechanical fastener(s) 1630 to constrain the associated activating mechanisms 1638a-c in positions where they intermesh to provide functionality at the end effector 1604 and the wrist 1606. Here, the shaft 1602, the end effector 1604, the articulable wrist 1606, the layers 1628b-e, and the activating mechanisms 1638a-c are all secured together to define a disposable instrument portion of the surgical tool 1600.

In these embodiments, the layers associated with performing other functionality of the surgical tool 1600 may be permanently secured within (or to) the handle 1614, thereby defining a reusable portion of the surgical tool 1600 that can be employed in more than one surgical procedure, and into which the disposable instrument portion may be releasably installed. In the illustrated embodiment, the first layer 1628a and its associated drive mechanisms define this reusable portion and, because these components are configured to translate the shaft 1602 along the longitudinal axis $A_1$, they also define a stage portion of the surgical tool 1600 into which the disposable instrument portion may be releasably installed. Here, the first layer 1628a of the carriage 1626, the lead screw 1622, and the carriage nut 1634 are operatively secured within (or to) the handle 1614, such that the first layer 1628a defines a type of "elevator" that is translationally driven and onto which the disposable instrument portion of the surgical tool 1600 may be releasably secured. Also, one or more of the splines 1624a-c may be operably secured within the handle 1614 to form part of the reusable stage portion. In some embodiments, the splines 1624a-c extend between the first and second ends 1618a,b, whereas in other embodiments, the splines 1624 may be configured as expandable or telescoping members extending between the first end 1618a and the first layer 1628a. In such embodiments, forces exhibited by the splines 1624a-c during rotation may be transferred through the first layer 1628a to the associated activating mechanisms 1638a-c in the disposable instrument portion to operate the surgical tool 1600.

FIG. 19 illustrates the surgical tool 1600 configured with a stage portion 1902 and an instrument portion 1904 that may releasably attach to the stage portion 1902, according to one or more embodiments. In this embodiment, the stage portion 1902 may be reused and the instrument portion 1904 may be removable and disposed of after a predetermined number of uses and then replaced with a new (or refurbished) instrument portion 1904. In the illustrated embodiment, the instrument portion 1904 includes various component parts of a surgical stapler (e.g., an "endocutter"), but in other embodiments the stage portion 1902 may be configured to receive instrument portions relating to other types of surgical tools.

As illustrated, the stage portion 1902 may include a removable cap 1906 that may be removed from the shroud 1640 so that the instrument portion 1904 may be installed on or otherwise coupled to the stage portion 1902. In some embodiments, the removable cap 1906 is removably attachable to the second end 1618b of the handle 1614 and removable to allow the instrument portion 1904 to be mated with a proximal side of the stage. Here, the instrument portion 1904 includes a handle assembly 1908 (alternatively referred to as a "handle drive assembly") comprising the layers 1628b-e, the thrust bearing layer 1628f, and the associated activating mechanisms 1638a-c constrained thereby, and the shaft 1602 operably extends through a correspondingly sized central aperture in at least a portion of the handle assembly 1908. In this embodiment, the handle assembly 1908 may be dropped onto a proximal side of the first layer 1628a (i.e., the elevator layer) after removal of the removable cap 1906.

Figure 20A:
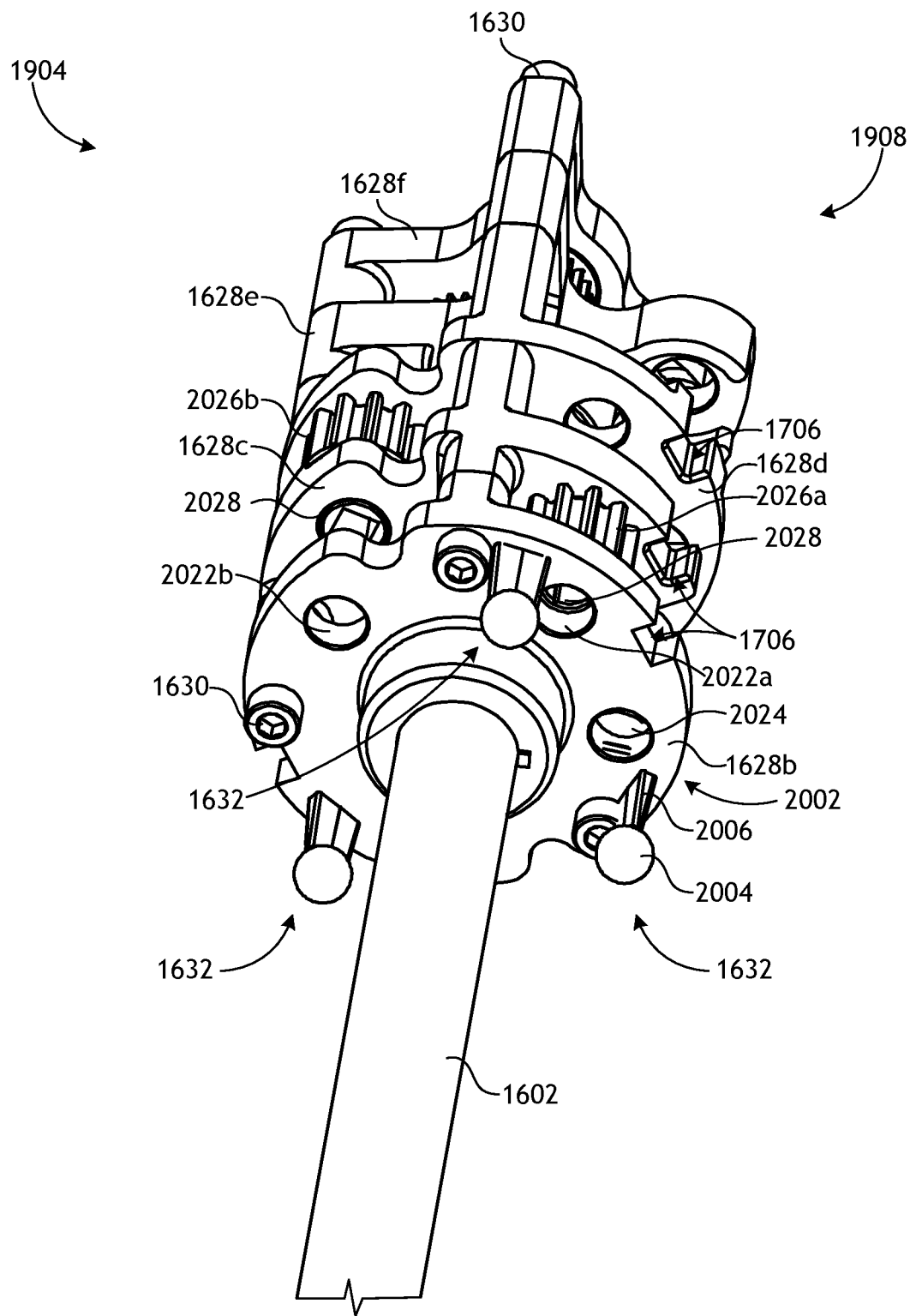
FIG. 20A provides an isometric end view of a portion of the instrument portion of FIG. 19.
Figure 20B:
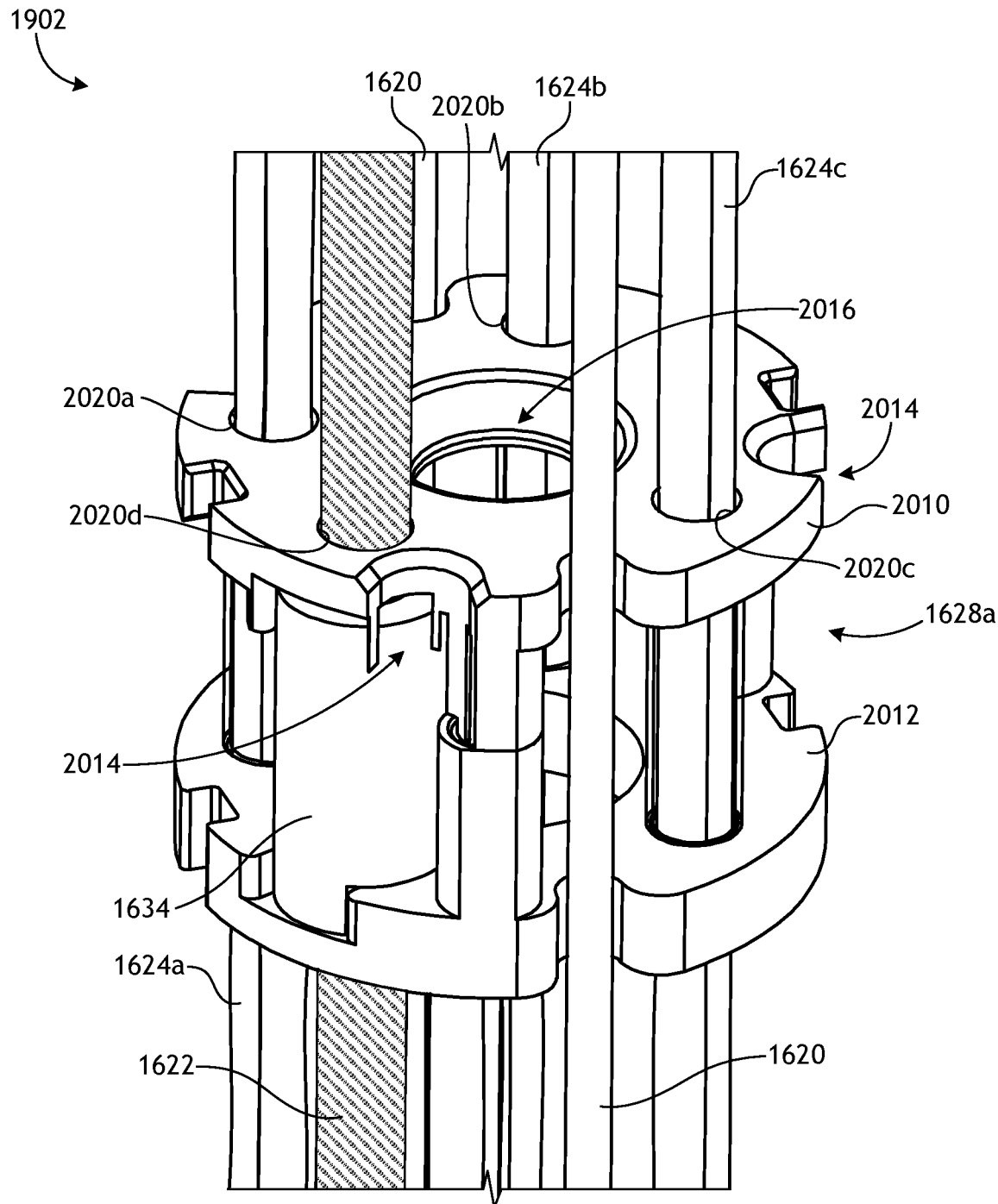
FIG. 20B provides an isometric end view of a portion of the stage portion of FIG. 19.

FIGS. 20A-20B show detailed views of the handle assembly 1908 of the instrument portion 1904 and the first layer 1628a (i.e., the elevator) of the stage portion 1902, according to one or more embodiments. Referring first to FIG. 20A, illustrated is a bottom isometric view of the instrument handle assembly 1908 of the instrument portion 1904. Here, the handle assembly 1908 includes an engagement end 2002 arranged to abut (or be in proximity to) the first layer 1628a (FIG. 20B) when the carriage 1626 is assembled for use. As shown, the snaps 1632 extend distally from the engagement end 2002, in a direction generally corresponding with the direction of the shaft 1602. The snaps 1632 may include a bulbous portion 2004 extending from a leg portion 2006, and may be biased radially inward towards the shaft 1602, which may prove advantageous in allowing each bulbous portion 2004 to be retained within corresponding openings of the first layer 1628a. As briefly mentioned above, the snaps 1632 and their corresponding openings in the first layer 1628a may be arranged to clock or angularly align the handle assembly 1908 relative to the stage portion 1902 (FIG. 20B), to thereby simplify proper installation.

FIG. 20B is an enlarged isometric view of the proximal end of the first layer 1628a, according to one or more embodiments. In the illustrated embodiment, the first layer 1628a is configured as an elevator having a floor 2010 (i.e., the elevator floor) fastened to a base 2012, and the carriage nut 1634 may be constrained between the floor 2010 and the base 2012. In some embodiments, the floor 2010 and the base 2012 may comprise an integral, monolithic part. In such embodiments, the carriage nut 1634 may be formed between the floor 2010 and the base 2012. Alternatively, the carriage nut 1634 may be positioned or defined within one or both of the coaxially aligned screw apertures 2020d defined in the floor 2010 and the base 2012 and through which the lead screw 1622 extends.

As illustrated, the floor 2010 includes one or more openings 2014 configured to align with corresponding bulbous portions 2004 (FIG. 20A) of each of the snaps 1632 (FIG. 20A). The openings 2014 correspond in size with the snaps 1632 such that they may receive and retain the bulbous portions 2004. The engagement end 2002 (FIG. 20A) may snap into the floor 2010 of the first layer 1628a (i.e., the elevator layer). In particular, the bulbous portions 2004 freely enter the corresponding openings 2014 in the floor 2010 when the floor 2010 slides proximally to a position where the openings 2014 are not constrained by the shroud 1640, but the bulbous portions 2004 are pressed into and retained in the corresponding openings 2014 in the floor 2010 by the shroud 1640 as the floor 2010 slides distally into shroud 1640. The shroud 1640 may help hold the snaps 1632 in an inward position where they are engaged by and retained within the corresponding openings 2014 in the floor 2010 of the first layer 1628a. Thus, the handle assembly 1908 cannot separate from the floor 2010 until the floor 2010 travels to a proximal position relative to the shroud 1640 sufficient to allow the snaps 1632 to deflect radially outward to a position where the bulbous portions 2004 are not retained within the corresponding openings 2014 of the floor 2010. For example, the snaps 1632 of the handle assembly 1908 may be flared radially outward so as to slide into wider regions of the corresponding openings 2014 in the floor 2010 when the first layer 1628a has been translated distally to a position where the corresponding openings 2014 in the floor 2010 are not constrained by the shroud 1640, and then the shroud 1640 may force the snaps 1632 into narrower regions of the corresponding openings 2014 as the handle assembly 1908 travels distally into the shroud 1640 to thereby lock the handle assembly 1908 to the first layer 1628a.

The splines 1624a-c may extend at least partially through the carriage 1626. In the illustrated embodiment, the splines 1624a-c extend through spline apertures 2020a-c defined in the first layer 1628a and the lead screw 1622 extends through a screw aperture 2020d also defined in the first layer 1628a (see FIG. 20B). In addition, the handle assembly 1908 includes spline passages 2022a-c (spline passage 2022c is occluded from view) and screw passage 2024 that extend through layers 1628b-e, and optionally through the thrust bearing layer 1628f, and align with the spline apertures 2020a-c and the screw apertures 2020d of the first layer 1628a such that the splines 1624a-c and the lead screw 1622 may extend through the handle assembly 1908 in addition to the first layer 1628a. Also, the drive mechanisms of the associated activating mechanisms 1638a-c may be keyed to the shape of the splines 1624a-c (FIG. 20A) so as to transmit rotation from the splines 1624a-c. Here, gears 2026a-c (FIG. 20A) of the associated activating mechanisms 1638a-c each have bores 2028 keyed to the cross section of the associated spline 1624a-c so as to transmit rotation from the spline 1624a-c to the associated gear 2026a-c.

In the illustrated example, the first layer 1628a (i.e., the elevator) may include a central opening 2016 arranged to receive the shaft 1602 and the end effector 1604 of the surgical tool 1600 as further described below.

Figure 21:
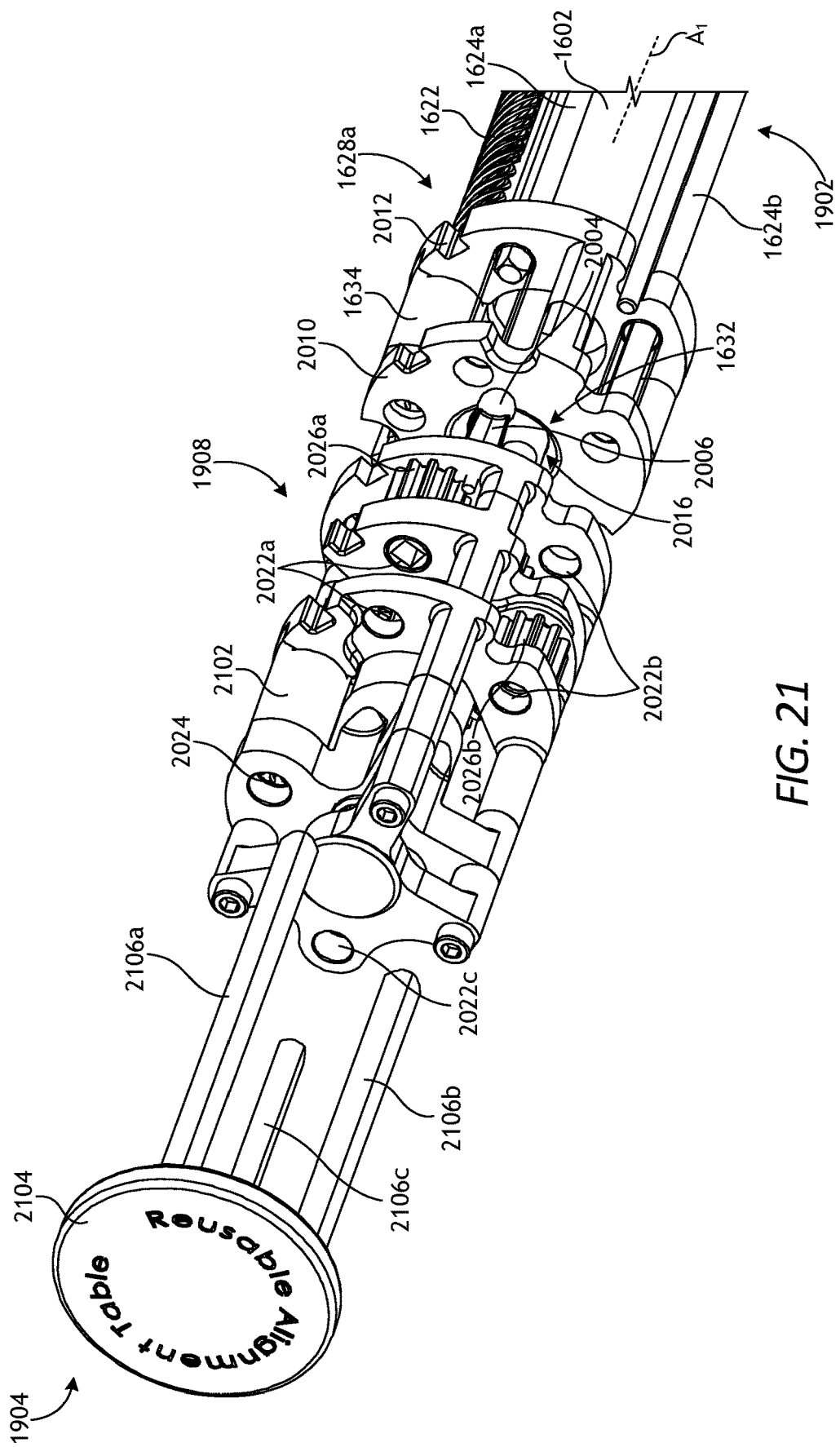
FIG. 21 illustrates a handle of the instrument portion depicted in FIG. 20A when unassembled from an elevator of the stage portion depicted in FIG. 20B and when unassembled from a table alignment tool, according to one or more embodiments.

FIG. 21 illustrates how the handle assembly 1908 of the instrument portion 1904 may be releasably attached to the stage portion 1902, according to one or more embodiments. In the illustrated embodiment, the handle assembly 1908 is depicted in the process of being positioned on the first layer 1628a (i.e., the elevator floor) of the stage portion 1902, with the shaft 1602 extending from the handle assembly 1908 and being inserted through the central opening 2016 of the first layer 1628a (i.e., the elevator). In some embodiments, the handle assembly 1908 may be configured to assist engaging the stage portion 1902. For example, the lead screw 1622 may be threaded through a second carriage nut 2102 aligned with the screw passage 2024 and constrained within the handle assembly 1908. Where included, the second carriage nut 2102 and or the screw passage 2024 may be utilized to help align (or clock) the handle assembly 1908 with respect to the first layer 1628a of the stage portion 1902, such that the splines 1624a-c align with the corresponding activating mechanisms 1638a-c (FIG. 17), and the second carriage nut 2102 may further add stability when the handle assembly 1908 is installed on the stage portion 1902. In addition, during manufacture the (first) carriage nut 1634 and the second carriage nut 2102 can be aligned and engaged with the lead screw 1622 to help remove any drive slop that may otherwise exist in the surgical tool 1600 when assembled.

In some embodiments, an alignment table 2104 may be utilized to help align the instrument portion 1904 with the stage portion 1902. FIG. 21 illustrates the alignment table 2104 (hereinafter, "the table 2104") when removed from the handle assembly 1908 of the instrument portion 1904. In the illustrated embodiment, the table 2104 includes four legs 2106a-d that align with the spline passages 2022a-c and the screw passage 2024. Thus, the legs 2106a-d may extend through their respective spline passages 2022a-c and screw passage 2024, which may help retain the associated activating mechanisms 1638a-c, and also help maintain alignment of the respective spline passages 2022a-c and screw passage 2024 for receiving the splines 1624a-c and the lead screw 1622. After connecting the handle assembly 1908 of the instrument portion 1904 to the stage portion 1902, the table 2104 may be removed, and the removable cap 1906 may then be secured on the shroud assembly 1700. In some embodiments, the table 2104 includes just three of the legs 2106a-c which are associated with the splines 1624a-c. In these embodiments, the legs 2106a-c are equal in length, such that each leg 2106a-c engages its associated spline 1624a-c within the first layer 1628a (i.e., in the elevator floor) to maintain alignment therewith when the first layer 1628a retracts to position and align splines 1624a-c with the associated activating mechanisms 1636a-c (FIG. 17).

Figure 22:
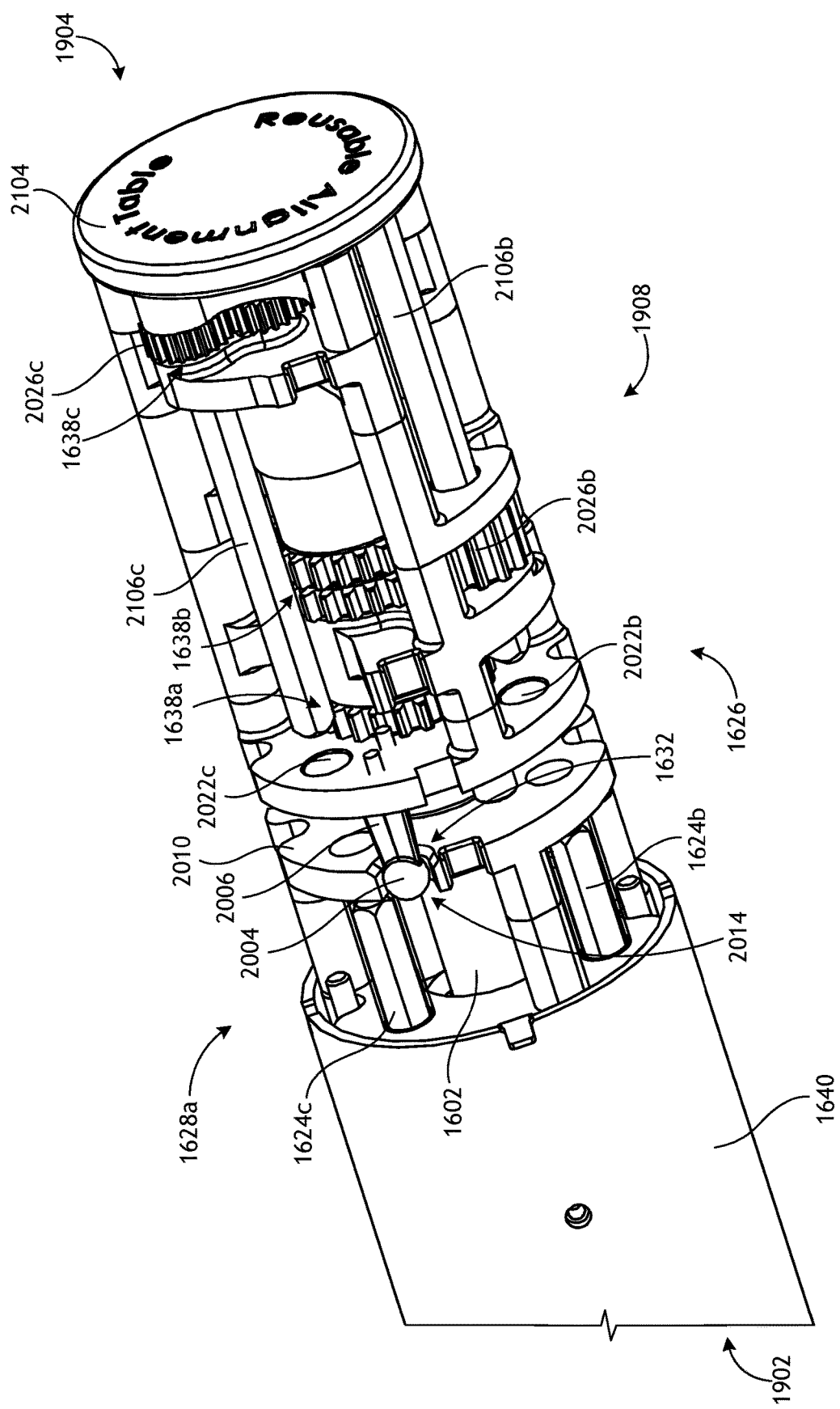
FIG. 22 illustrates table alignment tool of FIG. 21 being utilized to align the instrument portion and the stage portion of the surgical tool such that the handle of the instrument portion may be releasably secured to the elevator of the stage portion, according to one or more embodiments.

FIG. 22 illustrates the instrument portion 1904 being assembled on the stage portion 1902, according to one or more embodiments. As illustrated, the table 2104 is assembled on the table handle assembly 1908 of the instrument portion 1904 and the first layer 1628a has been moved proximally to a location where the floor 2010 extends outward of the shroud 1640 to expose the openings 2014 for receipt of the snaps 1632. By moving the first layer 1628a proximally as shown, the openings 2014 are not constrained in part by the shroud 1640 and the bulbous portions 2004 of the snaps 1632 may deflect and enter the openings 2014, thereby connecting the first layer 1628a of the carriage 1626 to the other layers 1628b-e of the carriage 1626, such that the carriage 1626 is now assembled as an integral unit. When the carriage 1626 moves distally into the shroud 1640 to a position where the floor 2010 is located within the shroud 1640, the openings 2014 will be constrained by the shroud 1640, such that the shroud 1640 retains the bulbous portions 2004 of the snaps 1632 within the openings 2014 by inhibiting the snaps 1632 from deflecting radially outward and separating from the openings 2014, as described above.

FIG. 22 also illustrates how the table 2104 may be utilized to align the handle assembly 1908 of the instrument portion 1904 with the stage portion 1902, according to one or more embodiments. As illustrated, the legs 2106a-d of the table 2104 may be positioned to extend within the spline passages 2022a-c and the screw passage 2024, and may be used to rotate the handle assembly 1908 into proper rotational alignment for receiving the splines 1624a-c and the lead screw 1622 of the stage portion 1902 of the surgical tool 1600. As the splines 1624a-c and the lead screw 1622 enter their associated spline passages 2022a-c and screw passage 2024, they may engage a distal end of the corresponding leg 2106a-d (of the table 2104) to move (or push) the table 2104 from the handle assembly 1908 as the handle assembly 1908 is pushed proximally onto the stage portion 1902. As a result, the table 2104 is gradually ejected and removed from the handle assembly 1908.

Removable Carriage Layers on Translating System

FIGS. 23A-23H illustrate example operation and modularity of the surgical tool 1600 of FIG. 16, according to one or more embodiments. In particular, FIGS. 23A-23H depict an exemplary progression for installing (or interchanging) the instrument portion 1904 on the stage portion 1902 of the surgical tool 1600.

Figure 23A:
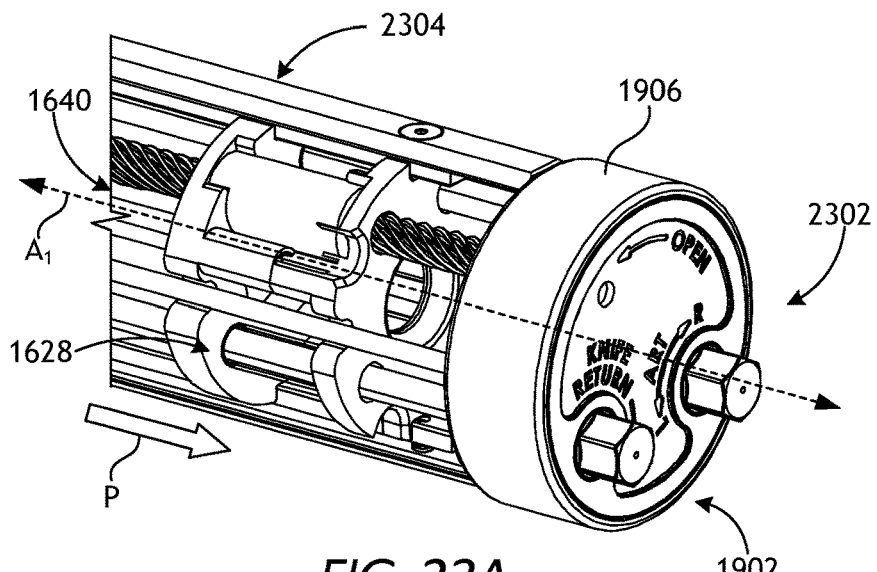
FIGS. 23A-23I illustrate example methods of operating and assembling a surgical tool, according to one or more embodiments.

Referring first to FIG. 23A, depicted is a proximal end 2302 of the stage portion 1902 of the surgical tool 1600 prior to installation of the instrument portion 1904 of the surgical tool 1600. The removable cap 1906 is depicted as having been installed on the proximal end 2302 of the stage portion 1902. As mentioned herein, the first layer 1628a provides the elevator 2304 that is translationally driven and movable within the shroud 1640 along the longitudinal axis $A_1$, and, when the handle assembly 1908 is installed on the elevator 2304, the elevator 2304 carries the handle assembly 1908 as it translates axially. Here, the elevator 2304 is illustrated moving in a proximal direction towards the proximal end 2302, as indicated by arrow P.

Figure 23B:
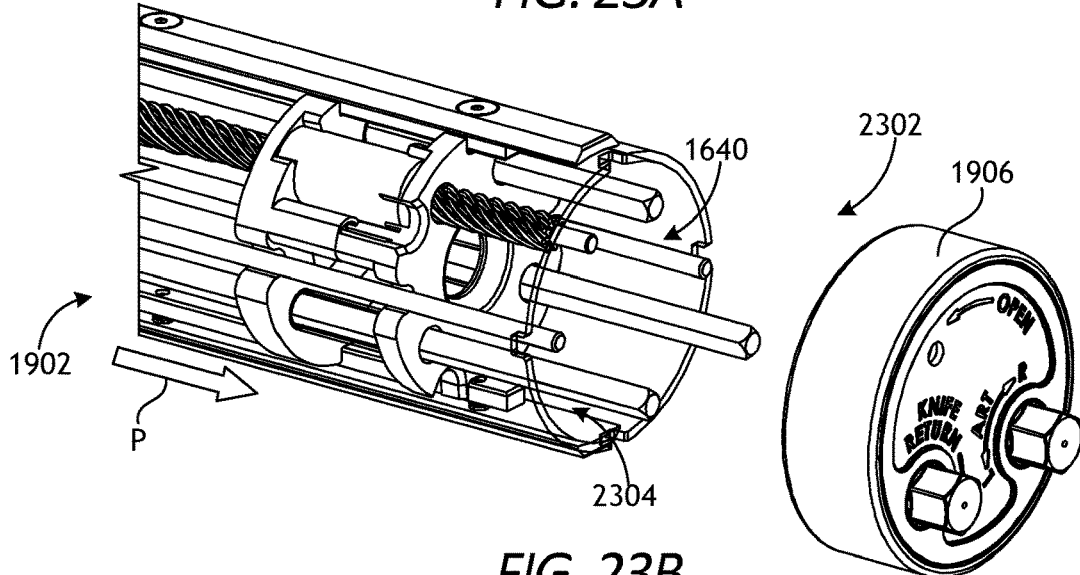

FIG. 23B depicts the proximal end 2302 after the cap 1906 has been removed. By removing the cap 1906 from the shroud 1640, a user may gain access to an interior of the stage portion 1902 in which the elevator 2304 resides and translates. After gaining access to the interior of the stage portion 1902, the user may install the instrument portion 1904 of the surgical tool 1600 on the elevator 2304, as described below. In at least some embodiments, the user may continue moving the elevator 2304 in a proximal direction, as indicated by the arrow P, to position where at least a portion of the elevator 2304 protrudes or extends out of the shroud 1640.

Figure 23C:
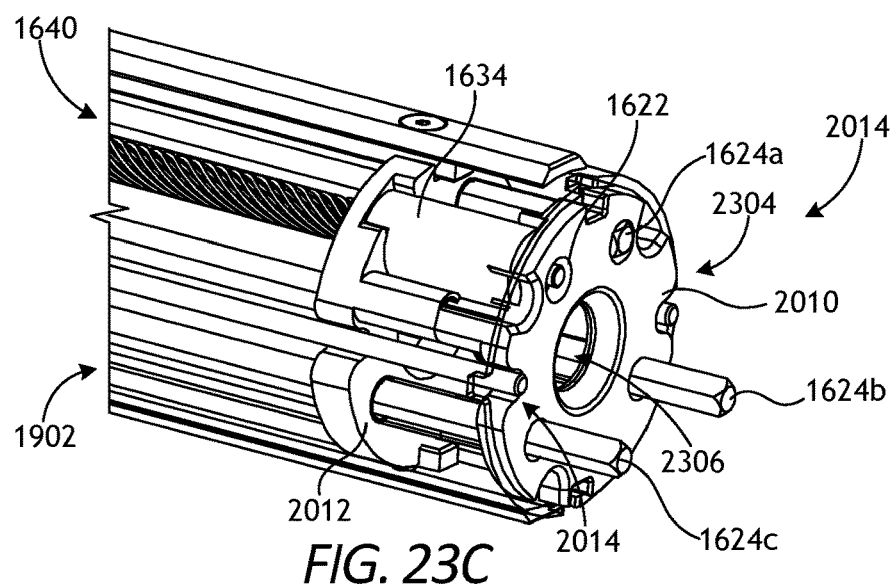

FIG. 23C illustrates the elevator 2304 having been proximally moved into a position where it partially protrudes from the shroud 1640. In this illustration, the elevator 2304, which includes the floor 2010 and the base 2012, has been moved proximally to where the floor 2010 is positioned outside of the shroud 1640 while the base 2012 remains within the shroud 1640. By moving the elevator 2304 in this manner, the openings 2014 in the floor 2010 are unconstrained by the shroud 1640 and open at a periphery of the floor 2010 such that the snaps 1632 (FIGS. 20A and 23E-23F) may be inserted therein, as generally described above. However, the elevator 2304 may be moved further proximally to where it further protrudes from the shroud 1640 or even fully protrudes from the shroud 1640.

The splines 1624*a-c* may each extend the same distance. However, in some embodiments, at least some of the splines 1624*a-c* extend at least partially through the elevator 2304 for engagement with the activating mechanisms 1638*a-c* (FIG. 22) of the handle assembly 1908 (FIG. 21) when the handle assembly 1908 is mounted to the floor 2010 of the elevator 2304. Here, the second and third splines 1624*b-c* protrude proximally from the floor 2010 when the elevator 2304 is positioned in this proximal position relative to the stage 1902 (FIGS. 23C-23D), whereas the first spline 1624*a* extends substantially flush with a face of the floor 2010 but will protrude proximally from the face of the floor 2010 when the elevator 2304 is moved distally (e.g., FIG. 23G). In other embodiments, however, each of the splines 1624*a-c* extends substantially flush with a face of the floor 2010 without protruding proximally from the face of the floor 2010 when the elevator 2304 is moved distally (e.g., FIG. 23G).

Figure 23D:
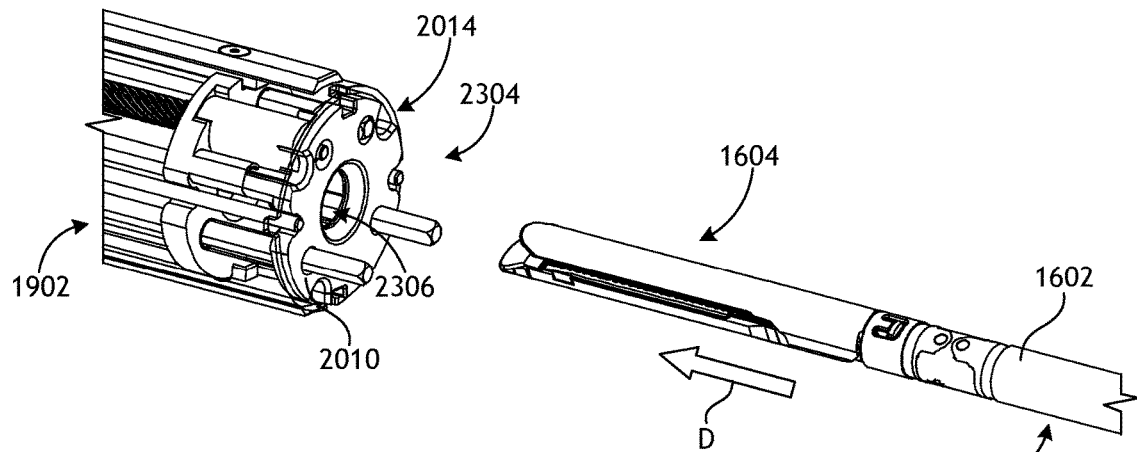

FIG. 23D illustrates the end effector 1604 of the instrument portion 1904 being moved distally towards the elevator 2304, as indicated by an arrow D. The instrument portion 1904 of the surgical tool 1600 (FIG. 20A) may be installed on the stage portion 1902 after moving the elevator 2304 into a position accessible to the handle assembly 1908 (FIG. 22). In the illustrated embodiment, the elevator 2304 includes an opening 2306 sized to receive the end effector 1604 and the shaft 1602. The user may continue moving the instrument portion 1904 distally D towards the elevator 2304 and insert the end effector 1604 and shaft 1602 of the instrument portion 1904 through the opening 2306 in the elevator 2304.

Figure 23E:
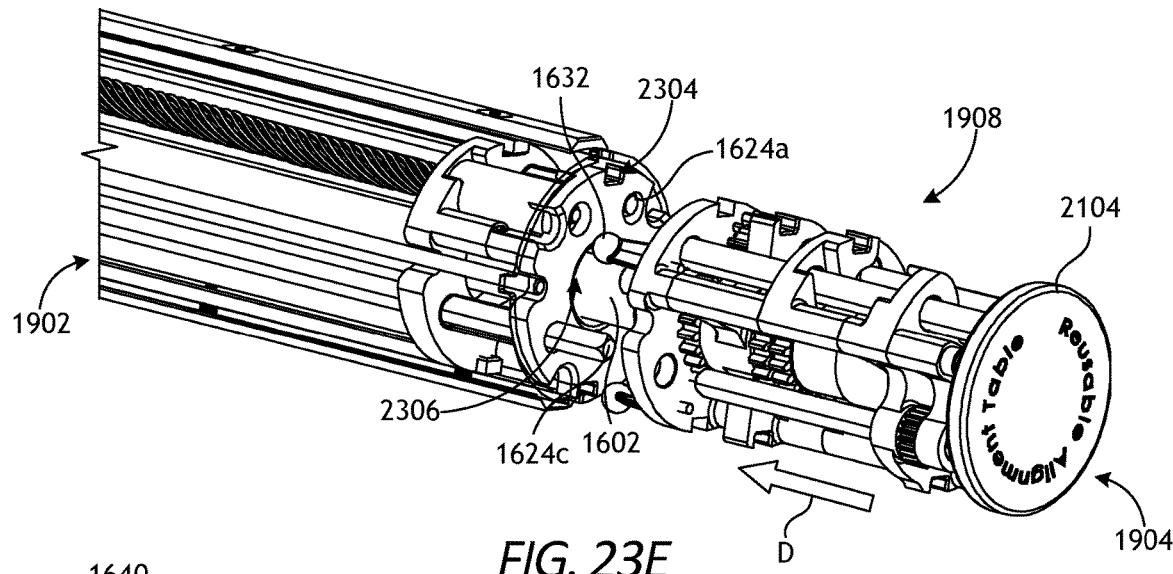

FIG. 23E illustrates the instrument portion 1904 being advanced onto the stage portion 1902, according to one or more embodiments. In particular, FIG. 23E illustrates the handle assembly 1908 after having inserted the end effector 1604 (FIG. 23D) and the shaft 1602 through the opening 2306 in the elevator 2304 and after having moved the handle assembly 1908 into a position proximate to the elevator 2304. In this embodiment, the table 2104 is assembled on the handle assembly 1908 to help align the activating mechanisms 1638*a-c* (FIG. 22) of the instrument portion 1904 with the splines 1624*a-c* of the stage portion 1902. The user may hold the table 2104 to advance and position the instrument portion 1904 relative to the stage portion 1902. Regardless of whether the table 2104 is utilized, the end effector 1604 and the shaft 1602 are advanced through the elevator 2304, and advanced distally through the stage portion 1902, through the first end 1618*a*, and through the alignment nozzle 1812 (FIG. 18B), as described above.

When the handle assembly 1908 is aligned with the elevator 2304, the snaps 1632 will be in alignment with their corresponding openings 2014 peripherally arranged about the floor 2010 (FIGS. 21-22), such that the instrument portion 1904 may be attached to the stage portion 1902 (FIG. 19). As mentioned above, the table 2104 may be utilized to align the stage portion 1902 and the instrument portion 1904 of the surgical tool 1600 (FIGS. 21-22). The table 2104 may be utilized to rotate the handle assembly 1908 about the longitudinal axis $A_1$ (FIG. 21) into a position where it is operatively aligned with the stage portion 1902. For example, the user may rotate the handle assembly 1908 into alignment with the elevator 2304 by rotating the table 2104 such that the first leg 2106*a* (FIG. 21) of the table 2104, which is arranged in the first spline passage 2022*a* (FIG. 21) defined in the handle assembly 1908, aligns with the first spline 1624*a* (FIG. 21); such that the second leg 2106*b* (FIG. 21) of the table 2104, which is arranged in the second spline passage 2022*b* (FIG. 21) defined in the handle assembly 1908, aligns with the second spline 1624*b* (FIG. 21); such that the third leg 2106*c* (FIG. 21) of the table 2104, which is arranged in the third spline passage 2022*c* (FIG. 21) defined in the handle assembly 1908, aligns with the third spline 1624*c* (FIG. 21); and such that the fourth leg 2106*d* (FIG. 21) of the table 2104, which is arranged in the screw passage 2024 (FIG. 21) defined in the handle assembly 1908, aligns with the lead screw 1622 (FIG. 21).

Figure 23F:
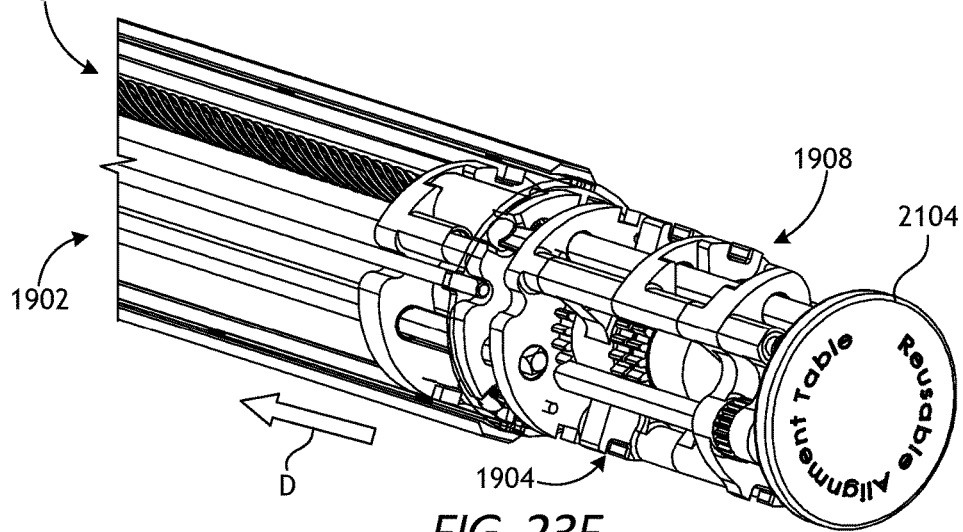

The handle assembly 1908 may be further advanced onto the stage portion 1902 and releasably secured on the stage portion 1902 as depicted in FIG. 23F. In particular, FIG. 23F illustrates the handle assembly 1908 being further advanced onto the stage portion 1902 such that the snaps 1632 engage or are otherwise received within corresponding openings 2014 (FIG. 20B) in the floor 2010 (FIGS. 20A-20B). In this embodiment, the floor 2010 of the elevator 2304 is positioned outside of the shroud 1640 (FIG. 22), such that the shroud 1640 does not constrain the openings 2014. In this manner, the snaps 1632 may enter the corresponding openings 2014 in the floor 2010. For example, the openings 2014 may include a chamfered lip configured to urge the bulbous portion 2004 of the snap 1632 outward as the snap 1632 is advanced into the opening 2014, thereby causing the leg portion 2006 carrying the bulbous portion 2004 to deflect (or flex) radially outward (FIG. 20A), and continual advancement of the snap 1632 towards its opening 2014 will radially expand the bulbous portion 2004 and the leg portion 2006 until the bulbous portion 2004 is in a position where the leg portion 2006 may bias (or snap) the bulbous portion 2004 within the opening 2014. Engagement of the snaps 1632 within their corresponding openings 2014 results in the handle assembly 1908 being releasably secured on the stage portion 1902. At this time, the user may manually remove the table 2104 (if utilized).

Figure 23G:
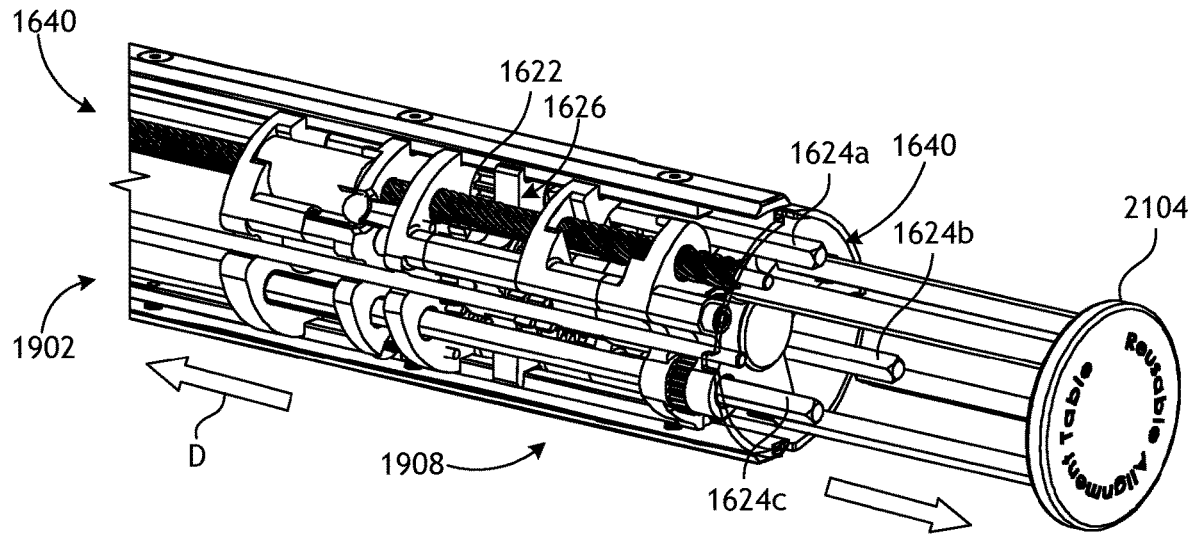

By coupling the handle assembly 1908 on the elevator 2304, the elevator 2304 will carry the handle assembly 1908 as it translates along the longitudinal axis $A_1$, such that the elevator 2304 and the handle assembly 1908 may translate together. As shown in FIG. 23G, the elevator 2304 and the handle assembly 1908 carried thereby may be distally translated, as indicated by the arrow D, upon actuation of the lead screw 1622. By retracting the elevator 2304 back within the shroud 1640, the inner wall of the shroud 1640 locks or traps the bulbous portions 2004 of the snaps 1632 (FIG. 23E) within their corresponding openings 2014 (FIG. 23C), such that the snaps 1632 may only be removed from their openings 2014 when the elevator 2304 is at least partially advanced out of the shroud 1640 (FIG. 23C).

Figure 23H:
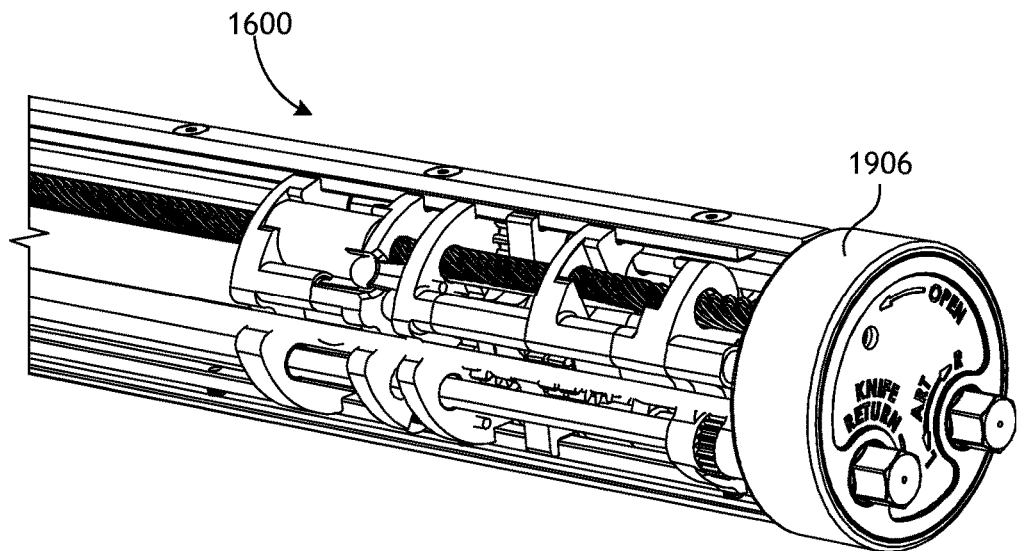

The elevator 2304 and the handle assembly 1908, when secured together in this manner, together define the carriage 1626. As the carriage 1626 advances in the distal direction (arrow D), the splines 1624*a-c* and/or the lead screw 1622 may extend into and through the spline passages 2022*a-c* and/or the screw passage 2024 (FIGS. 21-22), and continual distal advancement of the carriage 1626 may result in the table 2104 being ejected from the handle assembly 1908 as exemplified in FIG. 23G. For example, the splines 1624*a-c* and the lead screw 1622 enter the spline passages 2022*a-c* and the screw passage 2024, respectively, as the elevator 2304 pulls the handle assembly 1908 distally, the proximal ends of the splines 1624*a-c* and the lead screw 1622 (shown in FIGS. 23C-23D) will contact the ends of the legs 2106*a-d* (FIG. 21) of the table 2104 and thereby push the table 2104 out of the handle assembly 1908. Thus, the table 2104 may be automatically removed as the elevator 2304 pulls the handle assembly 1908 distally. Finally, the cap 1906 may be placed back on the proximal end 2302 of the stage portion 1902. FIG. 23H depicts the cap 1906 re-installed on the proximal end 2302 of the stage portion 1902.

Figure 23I:
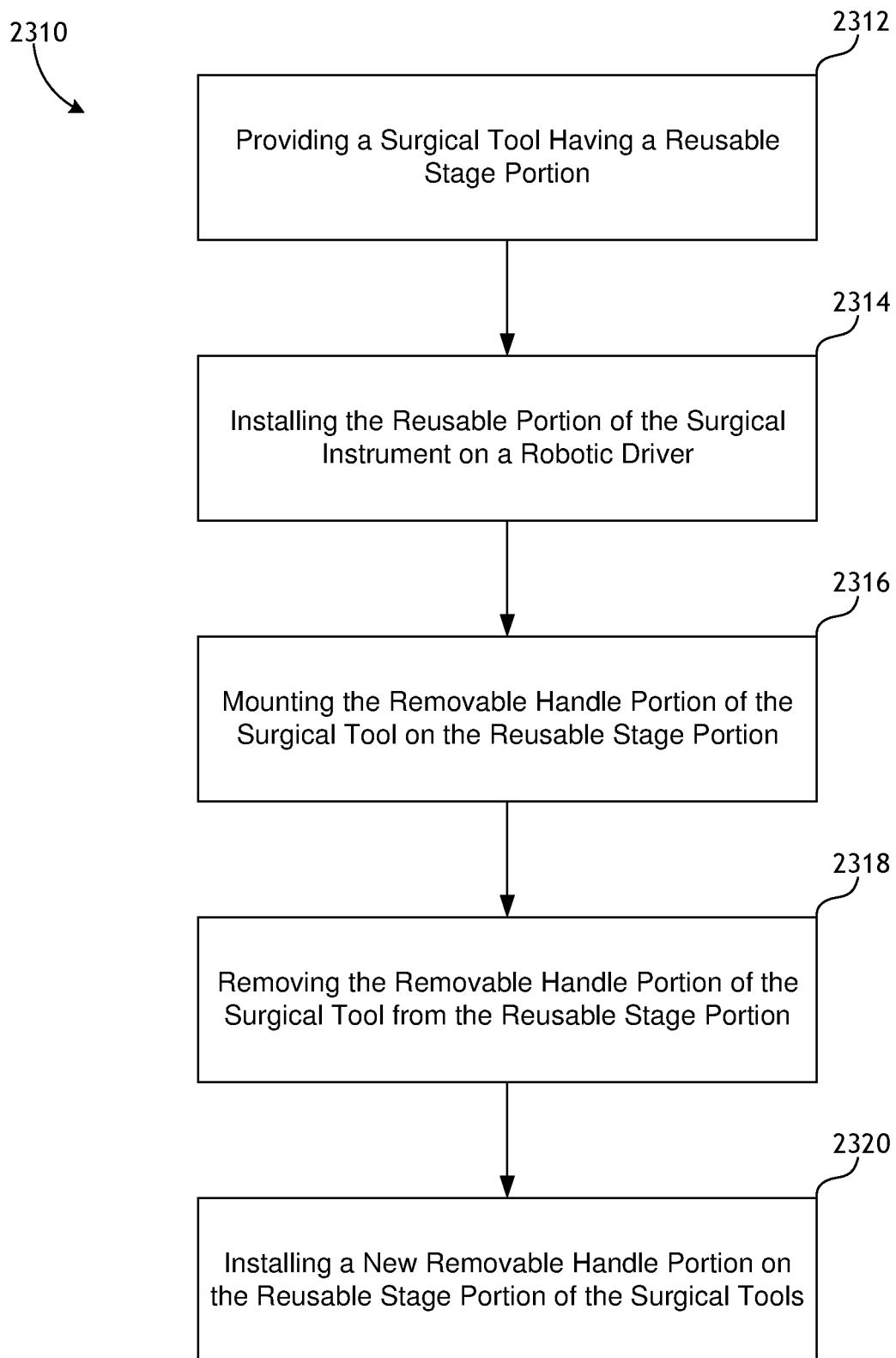

FIG. 23I is a schematic flowchart of an exemplary method 2310 for assembling and operating the surgical tool 1600 of FIG. 16), according to one or more embodiments. In the illustrated embodiment, the method 2310 includes providing a surgical tool having a reusable stage portion, as at 2312, and then installing the reusable portion of the surgical tool on a robotic instrument driver (e.g., the instrument driver 1102, 1200, 1800 of FIG. 11, FIG. 12, and FIGS. 18A-18B, respectively), as at 2314. As described herein, the reusable stage portion of the surgical tool may have an elevator floor on which a removable handle portion of surgical tool may be mounted, and the elevator floor may be actuated to carry the removable handle portion of the surgical tool in one or more directions. The removable handle portion may include an end effector that translates with the elevator floor. The removable handle portion of the surgical tool may be mounted on the reusable stage portion prior to installing the reusable stage portion on the robotic tool drive or may be mounted on the reusable stage portion after installing the reusable stage portion on the robotic tool drive.

In some embodiments, a method is provided for mounting the removable handle portion of the surgical tool on the reusable stage portion, which includes providing the reusable stage portion with the elevator floor in a proximal position suitable for receiving the removable handle portion, and may sometimes also include positioning the elevator floor in the proximal position suitable for receiving the removable handle portion and removing a top cap of the surgical tool to expose the elevator floor. Thus, the method 2310 may include the step of mounting the removable handle portion of the surgical tool on the reusable stage portion, as at 2316, and such step may further include either the sub-step of providing the reusable stage portion with the elevator floor already in a suitable proximal position for receiving the removable handle portion or the sub-steps of positioning the elevator floor in the proximal position suitable for receiving the removable handle portion and removing a top cap of the surgical tool to expose the elevator floor.

When in the proximal position, the removable handle portion may be operatively mounted on the elevator floor such that drive input imparted in the reusable stage portion by the robotic tool drive is transferred to activating mechanisms in the removable portion configured to activate and/or move the end effector 1604. Drive input forces may be imparted on the activating mechanisms of the removable portion via drive splines of the reusable stage portion and various configurations of the drive splines incorporated in the reusable spline portion, for example, telescoping drive splines that extend or retract with movement of the elevator floor and/or fixed length drive splines.

In embodiments where the surgical tool includes a shroud assembly, operatively mounting the removable handle portion on the elevator floor may include dropping the removable handle portion through the shroud assembly and onto the elevator floor. After operatively mounting the removable handle portion on the elevator floor, the removable cap may be placed on a proximal end. Accordingly, after the mounting step 2316, the method 2310 may include the step of using the surgical tool. During a procedure, the removable handle portion may be removed from the reusable stage portion and optionally disposed of, and then a new removable handle portion (e.g., having a different end effector or function) may be operatively mounted on the elevator floor, for example, by dropping the new removable handle portion onto the elevator floor through the shroud assembly. In this manner, the reusable stage portion is usable in more than just one operation and/or on more than one patient, thereby justifying the use and expense of components and materials in manufacture that have superior durability, weight, and stiffness, etc. characteristics. Thus, the method 2310 may further include the steps of removing the removable handle portion of the surgical tool from the reusable stage portion, as at 2318, and installing (mounting) a new removable handle portion of the surgical tool on the reusable stage portion, as at 2320.

Removable Endcap

In the embodiments described above, the splines 1624*a-c* (FIG. 16) and the lead screw 1622 (FIG. 16) extend between the first and second ends 1618*a,b* (FIG. 16). In these embodiments the splines 1624*a-c* and the lead screw 1622 extend from the first end 1618*a*, where they are operatively connected to the drive inputs 1636*a-d* of the surgical tool 1600 that are matable with and driven by a corresponding drive output 1824*a-f* of the instrument driver 1800, such that movement (rotation) of a given drive output 1824*a-f* correspondingly moves (rotates) the associated drive input 1636*a-d*, which thereby moves (rotates) the splines 1624*a-c* and the lead screw 1622 associated therewith. Also in these embodiments, the splines 1624*a-c* and the lead screw 1622 extend and are operatively coupled to the cap 1906.

Figure 24A:
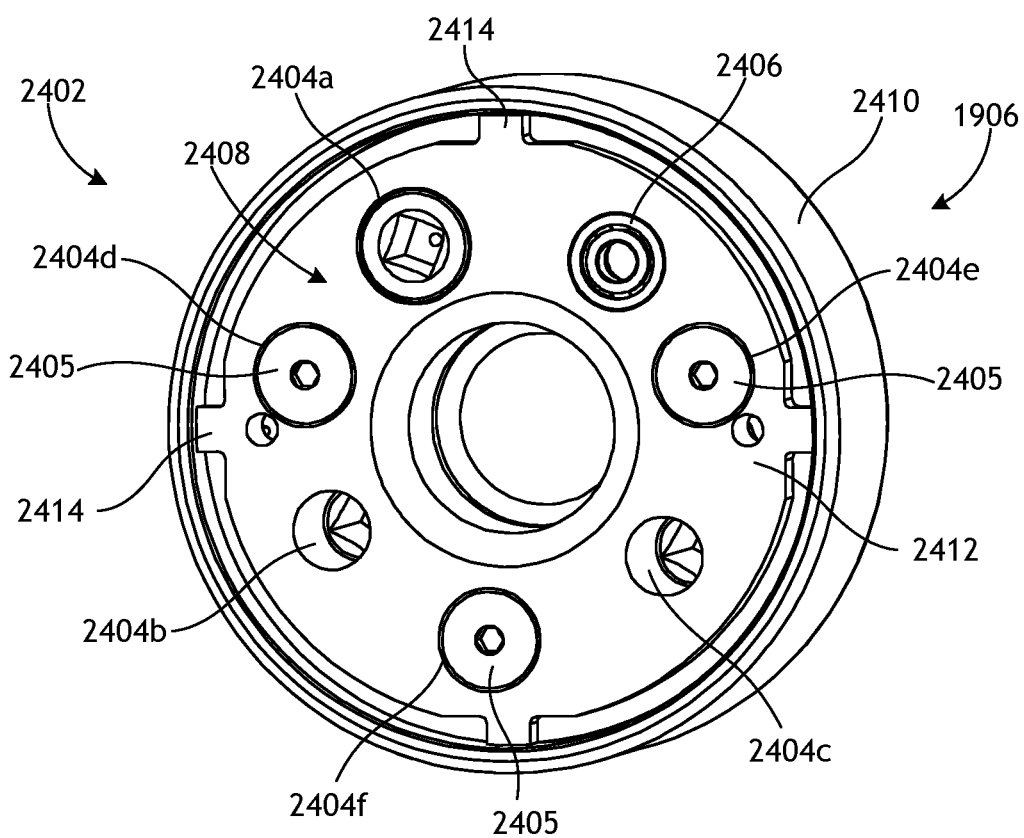
FIGS. 24A-24B illustrate respective bottom end, top end, and partially-exploded views of the removable cap of FIG. 19, according to one or more embodiments.
Figure 24B:
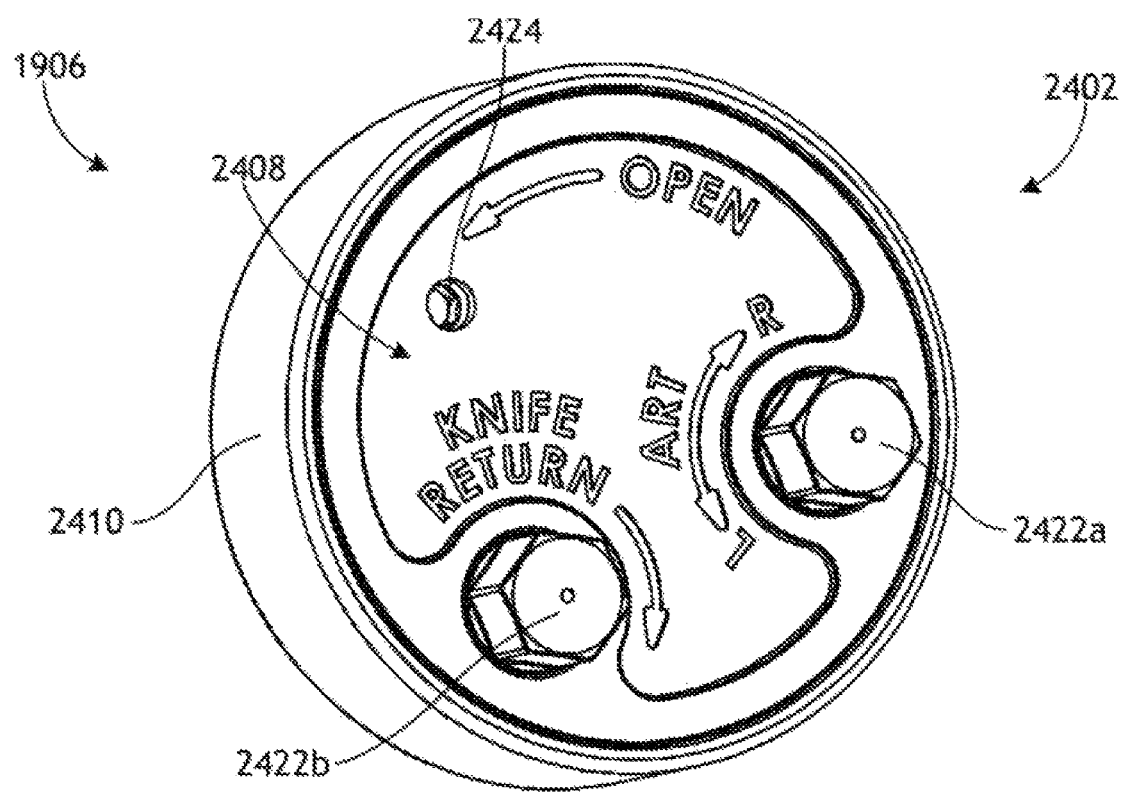

FIGS. 24A and 24B illustrate front and rear perspectives, respectively, of the cap 1906 of FIG. 19. In particular, FIG. 24A illustrates an interior engagement side 2402 of the cap 1906, according to one or more embodiments. The interior engagement side 2402 is configured to receive the ends of the splines 1624*a-c* and the lead screw 1622 when the cap 1906 is installed, and also configured to permit uncoupling from the splines 1624*a-c* and the lead screw 1622 for removal of the cap 1906. Thus, the interior engagement side 2402 may include couplings (receptacles) for each of the splines and/or drive screws. In the illustrated embodiment, the interior engagement side 2402 includes three spline couplings 2404*a-c* arranged to correspond with the three splines 1624*a-c*. However, the interior engagement side 2402 may include more or less than the three spline couplings 2404*a-c*, for example, in embodiments having more or less than the three splines 1624*a-c*. Thus, additional locations 2404*d-f* may be configured to receive additional splines or drive elements. Here, hex head set screws 2405 are arranged at the additional locations 2404*d-f* as the illustrated embodiment utilizes the three spline couplings 2404*a-c*. In addition, the interior engagement side 2402 includes a stage coupling 2406 arranged to correspond with the lead screw 1622.

The spline couplings 2404*a-c* and stage coupling 2406 are rotatable within the removable lid 1906, such that they rotate with their corresponding spline 1624*a-c* and lead screw 1622 when engaged therewith by installing the removable cap 1906. Also, any or all of the spline couplings 2404*a-c* and/or stage coupling 2406 may be keyed to the end geometry of their corresponding splines 1624a-c and/or lead screw 1622. In some embodiments, the splines 1624a-c each include a square shaped end (not illustrated) and each spline coupling 2404a-c includes a recess correspondingly shaped to receive the particular end geometry of the corresponding spline 1624a-c, so as to ensure that the spline couplings 2404a-c rotate with their associated splines 1624a-c while minimizing relative slippage therebetween. It should be appreciated, however, that the splines 1624a-c and the associated spline couplings 2404a-c may be keyed with other geometries (e.g., triangular, polygonal, ovoid, etc.) and that each associated spline and coupling pair may be keyed with a geometry different from one or more of the other associated spline and coupling pair, without departing from the present disclosure. Also in the illustrated embodiment, the stage coupling 2406 is illustrated as a low friction thrust bearing keyed to an end geometry of the lead screw 1622. In other embodiments, however, the lead screw 1622 may be differently connected to the stage coupling 2406, for example, in at least some embodiments, the lead screw 1622 may be threaded into the stage coupling 2406.

In the illustrated embodiment, the removable cap 1906 further includes a frame assembly 2408 and a ring 2410 arranged about the frame assembly 2408. The frame assembly 2408 is configured to retain the spline couplings 2404a-c and the stage coupling 2406. In some examples, additional spline couplings (e.g., similar to the spline couplings 2404a-c) may be arranged at the additional locations 2404d-f with an organization that comports with a standard alignment of splines such that the removable cap 1906 is utilizable with the maximum number of splines even where the handle assembly 1908 riding thereon may not be configured to receive input from one or more of the maximum number of splines.

The interior engagement side 2402 of the removable cap 1906 may be configured to mate with the shroud assembly 1700 (FIG. 17). In the illustrated example, the frame assembly 2408 includes a boss 2412 protruding outward to define a plurality of alignment tabs 2414. When installing the removable cap 1906, the alignment tabs 2414 may be used to ensure proper alignment by locating the alignment tabs 2414 within the corresponding alignment notches 1708 defined in the shroud 1640.

Telescoping Splines

FIGS. 25A and 25B are partial cross-sectional side views of one or more example embodiments of the splines 1624a-c of FIGS. 16 and 17, according to embodiments of the present disclosure. In at least some embodiments, one or more of the splines 1624a-c (and/or the lead screw 1622) are configured to extend less than the entire distance between the first and second ends 1618a,b. For example, rather than being constrained between the first end 1618a and the removable cap 1906 as described above, one or more of the splines 1624a-c may be constrained between the first end 1618a and the carriage 1626. In these embodiments, one or more of the splines 1624a-c may be configured to telescope such that it/they expand or contract as the elevator 2304 of the carriage 1626 translates.

FIGS. 25A and 25B illustrate the splines 1624a-c as telescoping structures. In the illustrated embodiment, the splines 1624a-c are configured to nest within a handle interface 2502 of the surgical tool 1600 (FIG. 16). As illustrated, the handle interface 2502 is a structure of the surgical tool 1600 within which the one or more rotatable drive inputs (e.g., drive inputs 1636a-d) are operatively arranged for receiving input (e.g., rotational input) from the rotatable drive outputs (e.g., drive outputs 1824a-d) of the instrument driver 1800 (FIG. 18B). Also, the splines 1624a-c are operatively connected to the drive inputs 1636a-d within the handle interface 2502. Here, the handle interface 2502 includes a floor 2504, and the splines 1624a-c extend from their respective rotatable drive inputs 1636a-d, upward through the floor 2504, and to the elevator 2304.

In the illustrated embodiment, the splines 1624a-c each comprise a series of telescoping portions 2506 configured to nest within the handle interface 2502. FIG. 25A illustrates the carriage 1626 having been translated into a distal most position to thereby cause the telescoping portions 2506 of the splines 1624a-c to substantially retract and nest within the handle interface 2502. In this manner, the splines 1624a-c may be in a retracted or nested condition where portions of the splines 1624a-c are nested beneath the floor 2504 when the elevator 2304 has translated into a distal most position.

FIG. 25B illustrates the elevator 2304 having been at least partially translated in a proximal direction to thereby cause the series of telescoping portions 2506 to telescope (or elongate, expand, extend, un-nest, etc.) into an at least partially extended state. In this manner, one or more of the series of telescoping portions 2506 may expand (extend) through the floor 2504 and into a stage chamber 2508 within which the carriage 1626 translates as the elevator 2304 pulls (or carries, expands, telescopes, un-nests, etc.) the splines 1624a-c into their extended state.

The series of telescoping portions 2506 may each include individual telescoping spline portions 2510a-d. The telescoping spline portions 2510a-d are operatively connected in series to transmit torque imparted on the rotatable drive inputs (e.g., the drive inputs 1636b-d) by the instrument driver 1800 to a coupling 2512. Thus, the telescoping spline portions 2510a-d (of each spline 1624a-c) may be rotationally fixed relative to each other about an associated spline axis $S_1$, $S_2$, $S_3$. In addition, the telescoping spline portions 2510a-d of each spline 1624a-c are serially connected such that they may telescope within each other.

Here, the first telescoping spline portion 2510a exhibits the largest diameter, and the second telescoping spline portion 2510b exhibits the second largest diameter and is slidingly retained within the first telescoping spline portion 2510a. The third telescoping spline portion 2510c exhibits the third largest diameter and is slidingly retained within the second telescoping spline portion 2510b, and the fourth telescoping spline portion 2510d exhibits the fourth largest diameter and is slidingly retained within the third telescoping spline portion 2510c. In this manner, the fourth telescoping spline portion 2510d may slide into (or nest within) the third telescoping spline portion 2510c, the third telescoping spline portion 2510c may slide into (or nest within) the second telescoping spline portion 2510b, the second telescoping spline portion 2510b may slide into (or nest within) the first telescoping spline portion 2510a, and the telescoping spline portions 2510a-d may nest together as the elevator 2304 moves distally towards the floor 2504. Here, the telescoping spline portions 2510a-d nest in the handle interface 2502 such that the splines 1624a-c are concealable within the handle interface 2502, but in other embodiments, they may be differently configured, for example, to nest within the elevator 2304.

In some embodiments, the coupling 2512 may include a receptacle 2514 configured to transmit torque to a corresponding activating mechanism 1638a-c configured to drive and cause operation of specific functions of the end effector 1604. In some embodiments, removable splines 2516a-c may be provided in the handle assembly 1908 for receiving drive input from the couplings 2512 and transmitting that imparted torque to the associated activating mechanisms 1638a-c, such that torque imparted by the instrument driver 1800 (FIGS. 18A-18B) is operatively transferred to the handle assembly 1908 to permit various movements and actions of the end effector 1604. Here, the removable splines 2516a-c may each include a torsion shaft 2520 having an input end 2522 positioned to communicate or mate with the coupling 2512 via the receptacle 2514, which may rotationally lock the torsion shaft 2520 of each removable spline 2516a-c with the associated coupling 2512 and series of telescoping portions 2506. For example, the receptacle 2514 may be keyed to the particular spline geometry of the input end 2522 associated with it. Also, each torsion shaft 2520 may include an output 2524 in operable engagement with the associated activating mechanisms 1638a-c. In some examples, the output 2524 is an output or drive gear that is rotationally fixed on the torsion shaft 2520 such that they rotate in unison.

FIG. 25B depicts the carriage 1626 partially disassembled (i.e., with the handle assembly 1908 partially removed from the elevator 2304), so as to more fully illustrate orientation and interaction of components within the handle assembly 1908. For example, FIG. 25B illustrates the telescoping nature of the series of telescoping portions 2506, the orientation of the removable splines 2516a-c and the associated activating mechanisms 1638a-c, engagement of the removable splines 2516a-c of the handle assembly 1908 with the couplings 2512 of the elevator 2304, etc. In this example, the first layer 1628a is the elevator 2304 on which the structural layers 1628b-d are releasably attachable and is associated with controlling axial translation of the carriage of the surgical tool 1600. The second layer 1628b is the bottom layer of the handle assembly 1908 and is associated with controlling a first functionality of the end effector 1604, the third layer 1628c is the middle layer of the handle assembly 1908 and is associated with controlling a second functionality of the end effector 1604, and the fourth layer 1628d is the upper layer of the handle assembly 1908 and is associated with controlling a third functionality of the end effector 1604.

In the illustrated example, the shroud 1640 is illustrated as a rigid tube member that does not expand or contract. Thus, in some examples the stage chamber 2508 defined by the shroud 1640 may be of fixed volume. However, in other examples, the shroud 1640 may be configured to expand or contract with movement of the elevator 2304 and telescoping splines 1624a-c. For example, the shroud 1640 may comprise a series of telescoping shroud portions arranged to telescope between nested and un-nested positions with movement of the elevator 2304.

FIGS. 26A and 26B illustrate the splines 1624a-c configured to telescope, according to one or more alternate embodiments of the present disclosure. In the illustrated embodiment, the splines 1624a-c are provided as a series of telescoping spline members 2602 arranged to telescope from a nested or retracted position (FIG. 26A) into one or more extended positions (FIG. 26B). Thus, in this example, the splines 1624a-c are concealable within the elevator 2304.

Here, the series of telescoping spline members 2602 are configured to telescope into the elevator 2304. For example, each of the series of telescoping portions 2602 may include individual telescoping spline portions 2604a-d. The telescoping spline portions 2604a-d are operatively connected in series to transmit torque imparted on the rotatable drive inputs (e.g., the drive inputs 1636b-d) by the instrument driver 1800 to a coupling 2606. Thus, the telescoping spline portions 2604a-d (of each spline 1624a-c) may be rotationally fixed relative to each other about an associated spline axis $S_1$, $S_2$, and $S_3$. In addition, the telescoping spline portions 2604a-d (of each spline 1624a-c) are serially connected such that they may telescope within each other.

Here, the first telescoping spline portion 2604a exhibits the largest diameter and is at least partially arranged in or otherwise coupled to the elevator 2304, and the second telescoping spline portion 2604b exhibits the second largest diameter and is slidingly retained within the first telescoping spline portion 2604a. The third telescoping spline portion 2604c exhibits the third largest diameter and is slidingly retained within the second telescoping spline portion 2604b, and the fourth telescoping spline portion 2604d exhibits the fourth largest diameter and is slidingly retained within the third telescoping spline portion 2604c. In this manner, the fourth telescoping spline portion 2604d may slide into (or nest within) the third telescoping spline portion 2604c, the third telescoping spline portion 2604c may slide into (or nest within) the second telescoping spline portion 2604b, the second telescoping spline portion 2604b may slide into (or nest within) the first telescoping spline portion 2604a, and the telescoping spline portions 2604a-d may nest together as the elevator 2304 moves distally towards the floor 2504. Thus, the telescoping spline portions 2604a-d are shown configured to nest in the first frame layer 1628a (i.e., the elevator layer 2304), but in other embodiments they may be configured to nest differently.

In some embodiments, the lead screw 1622 is a rigid member having a non-telescoping configuration. In other embodiments, however, the lead screw 1622 may be configured to telescope with the elevator 2304. For example, the lead screw 1622 may be a telescoping linear actuator having a centermost telescoping member terminating on the first layer 1628a (i.e., the elevator floor).

Figure 27:
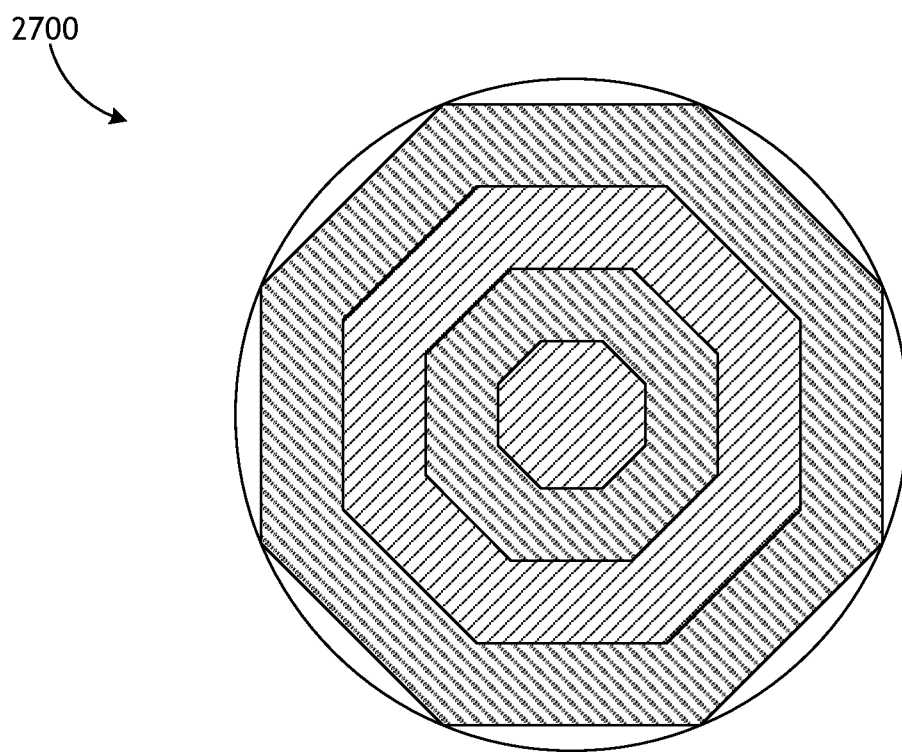
FIG. 27 illustrates a telescoping spline configuration, according to one or more embodiments.

FIG. 27 is a top, cross-sectional view of a telescoping spline configuration 2700 according to one or more additional embodiments. The splines 1624a-c (FIGS. 26A-26B) may have varying telescoping configurations, such as the telescoping spline configuration 2700 exemplified in FIG. 27. In the illustrated embodiment, the telescoping spline configuration 2800 includes a series of concentric spline portions having corresponding keyed geometries, so as to rotate together and transmit a torsional force through the telescoping spline configuration 2800.

FIGS. 28A-28B illustrate an expandable and collapsible shroud 2802 in respective collapsed and expanded positions, according to one or more embodiments. As mentioned above, the shroud 1640 may be configured to expand or contract with the elevator 2304. In the illustrated embodiment, the expandable and collapsible shroud 2802 includes an expandable portion 2804 arranged to expand or contract with the elevator 2304. The expandable portion 2804 may have various configurations, such as a bellows or accordion-like configuration, a telescoping configuration, etc.

Drive Puck for Translating System with Mapped Instrument Drive Outputs

Figure 29:
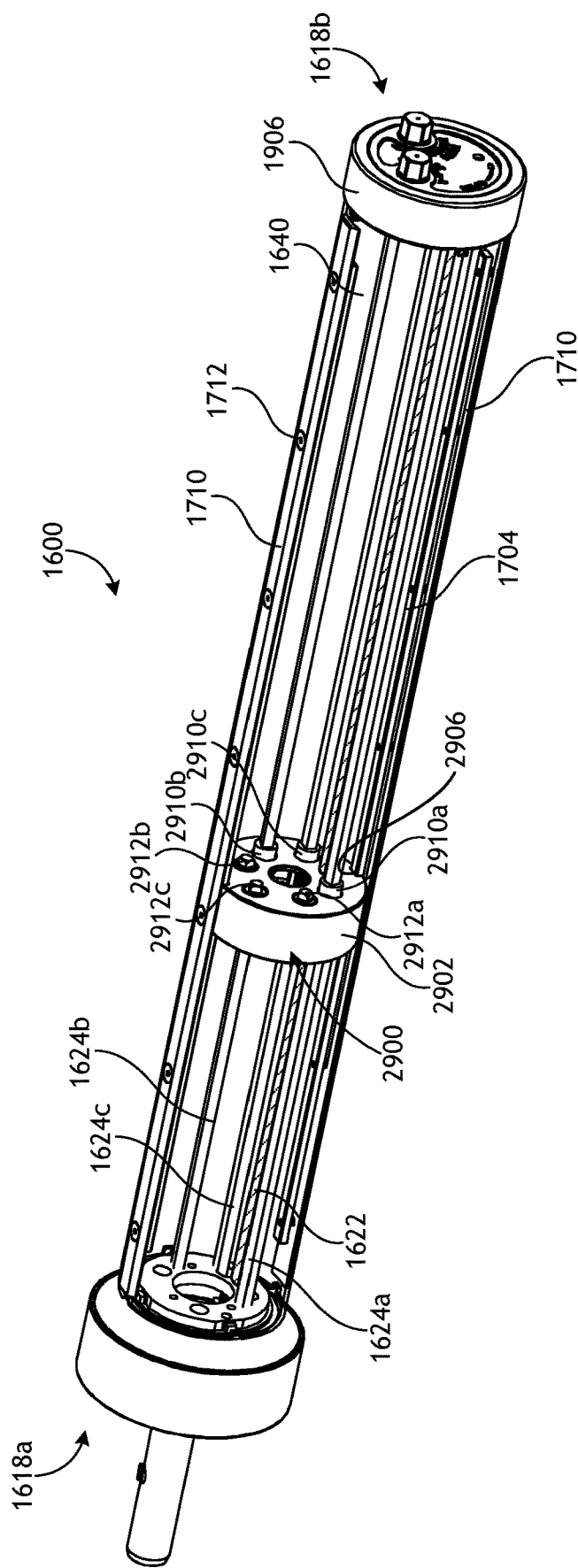
FIG. 29 is an isometric side view of an example stage for a surgical tool utilizing a translatable drive puck configured to map spline input to different output locations, according to one or more embodiments.

FIG. 29 illustrates an elevator of the surgical tool 1600 that operates as a translatable drive puck (or nut) 2900, according to one or more embodiments of the present disclosure. In these embodiments, the drive puck 2900 not only functions as a stage for the surgical tool 1600, but also maps or transfers (e.g., via gearing) input forces received from the splines 1624a-c to predetermined drive locations within the envelope of the shroud 1640 that do not correspond (or are unassociated) with locations of the associated splines 1624. As will be appreciated, this can allow utilization of differently shaped shrouds or shroud assemblies.

As illustrated, the drive puck 2900 is configured to translate on the splines 1624*a-c* within the shroud 1640 and transfer drive input forces received therefrom to off-set or remote drive output locations. The drive puck 2900 rides or slides on the splines 1624*a-c* within the shroud 1640 and is thus a translatable drive puck that may function as the stage (elevator) of the surgical tool 1600. In the illustrated example, the drive puck 2900 translates along the splines 1624*a-c* via actuation of the lead screw 1622. Thus, the drive puck 2900 may include a drive screw portion (obscured from view) that intermeshes with the lead screw 1622. In some embodiments, for example, the carriage nut 1634 (FIG. 16) may be constrained within a body 2902 of the drive puck 2900. However, in other examples, a threaded bore 2904 (occluded, see FIGS. 30A-30B and FIG. 31) may be formed in the body 2902 and configured to receive the lead screw 1622 and cause translation of the drive puck 2900 upon rotation of the lead screw 1622.

While the drive puck 2900 is configured to translate axially within the shroud 1640, rotation of the drive puck 2900 within the shroud 1640 is inhibited. In the illustrated example, the drive puck 2900 defines or otherwise provides one or more guide notches 2906 sized to receive the rails 1704 such that the rails 1704 may ride within the notches 2906 as the drive puck 2900 translates within the shroud 1640. Consequently, the rails 1704 guide the drive puck 2900 as it translates axially within the shroud 1640 and also constrain the drive puck 2900 from rotating by countering any rotational forces acting on the drive puck 2900. In this manner, any rotational force acting on the drive puck 2900 will be assumed by the rails 1704, such that the rotational force is not imparted to the splines 1624*a-c* extending through the drive puck 2900.

As illustrated, the splines 1624*a-c* extend through the drive puck 2900 and the drive puck 2900 is able to slide on or otherwise axially traverse the splines 1624*a-c*. Here, the drive puck 2900 is illustrated and described as being operable with three of the splines 1624*a-c*, however, the drive puck 2900 may be differently configured so that it is operable using input from any number and/or arrangement of splines. The drive puck 2900 may translate on the splines 1624*a-c* both when the splines 1624*a-c* are stationary and when one or more of the splines 1624*a-c* are activated (i.e., rotated via the instrument driver 1800). To accomplish this, as illustrated, the drive puck 2900 may include spline couplings 2910*a-c* that correspond with the splines 1624*a-c* and are rotatable with the associated spline 1624*a-c*. Here, the first spline 1624*a* extends through the first spline coupling 2910*a*, the second spline 1624*b* extends through the second spline coupling 2910*b*, and the third spline 1624*c* extends through the third spline coupling 2910*c*. The spline couplings 2910*a-c* may each include an interior geometry configured to engage and mate with the geometry of the associated spline 1624*a-c*. In some embodiments, the spline couplings 2910*a-c* may each include a geometry keyed to the cross-section of the associated spline 1624*a-c*. In the illustrated embodiments, the spline couplings 2910*a-c* each define (exhibit) a square-shaped geometry matable with the associated spline 1624*a-c* such that rotation of the spline 1624*a-c* correspondingly rotates the associated spline coupling 2910*a-c*.

According to embodiments of the present disclosure, the drive puck 2900 may be configured such that the spline couplings 2910*a-c* transfer drive input forces to locations on the drive puck 2900 that are distant or positioned away (laterally offset) from the spline couplings 2910*a-c*. In particular, the spline couplings 2910*a-c* receive drive input forces from the associated splines 1624*a-c*, and internal gearing within the drive puck 2900 maps or transmits those drive input forces to corresponding drive outputs (e.g., drive pegs) at locations that do not correspond (align) with the spline couplings 2910*a-c* and the associated splines 1624*a-c*. Thus, the drive puck 2900 may receive drive input from the splines 1624*a-c* extending through an input region of the drive puck 2900 and transfer that drive input to any output region of the drive puck 2900 that is positioned away from the input region and configured to receive a removable handle drive assembly of the surgical tool 1600 as described herein.

Figure 30:
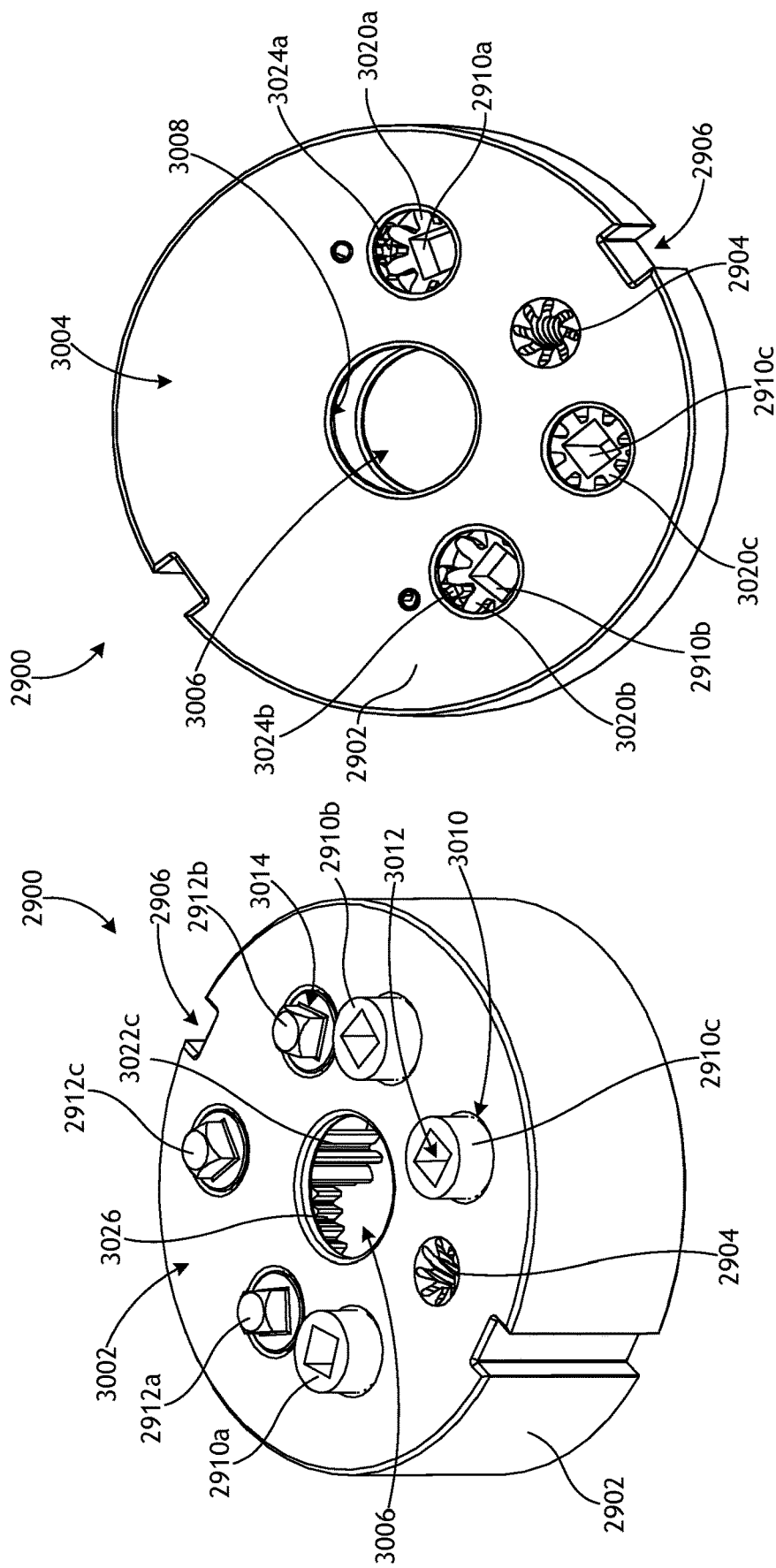
FIGS. 30A and 30B illustrate a proximal face and a distal face, respectively, of the translatable drive puck of FIG. 29 when unassembled.

In the illustrated example, the drive puck 2900 is cylindrically circular in shape and thus includes a generally circular proximal face (see FIG. 30A) and a generally circular distal face (see FIG. 30B). Here, the spline couplings 2910*a-c* are arranged on a first arcuate portion (e.g., a first half-arc-length) of the circular shaped distal and proximal faces of the drive puck 2900. In addition, the drive puck 2900 includes one or more instrument drive outputs 2912*a-c* operatively connected with an associated one of the spline couplings 2910*a-c*. Here, the instrument drive outputs 2912*a-c* comprise drive pegs and are arranged on a second arcuate portion (e.g., a second half-arc-length) of the drive puck 2900. In one example, the instrument drive outputs 2912*a-c* are provided as drive pegs with stub shafts extending (or protruding) outward from the proximal face of the drive puck 2900.

In the illustrated example, the first spline coupling 2910*a* is operatively connected to the first instrument drive output 2912*a* such that rotation of the first spline coupling 2910*a* (via the first spline 1624*a*) rotates the first instrument drive output 2912*a*. The second spline coupling 2910*b* is operatively connected to the second instrument drive output 2912*b* such that rotation of the second spline coupling 2910*b* (via the second spline 1624*b*) rotates the second instrument drive output 2912*b*. The third spline coupling 2910*c* is operatively connected to the third instrument drive output 2912*c* such that rotation of the third spline coupling 2910*c* (via the third spline 1624*c*) rotates the third instrument drive output 2912*c*. As more fully described below, internal gearing may be provided within the drive puck 2900 to operatively intermesh each of the spline couplings 2910*a-c* with the instrument drive output 2912*a-c* associated therewith. In this manner, the drive puck 2900 receives drive input forces through the spline couplings 2910*a-c* interacting with the splines 1624*a-c* in the first hemisphere, and internal gearing within the drive puck 2900 transfers (or maps) each drive input force to one of the instrument drive outputs 2912*a-c* located in the second hemisphere. Thus, the instrument drive outputs 2912*a-c* may be arranged at locations about the drive puck 2900 that are independent of the orientation of the splines 1624*a-c* and/or at locations about the drive puck 2900 that do not correspond with the particular location(s) at which their associated splines 1624*a-c* engage the drive puck 2900.

FIGS. 30A and 30B are isometric top and bottom views, respectively, of the drive puck 2900 of FIG. 29, according to one or more embodiments. More specifically, FIG. 30A depicts a first or "proximal" face 3002, and FIG. 30B depicts a second or "distal" face 3004 opposite the proximal face 3002. As illustrated, the drive puck 2900 defines a central aperture or bore 3006 extending through the body 2902 between the proximal and distal faces 3002, 3004. The bore 3006 may be sized to receive the shaft 1602 of the surgical tool 1600 (FIG. 16) when a handle drive assembly is installed thereon. In the illustrated embodiment, the body 2902 is hollow and defines an interior volume 3008 that is in communication with the bore 3006.

In some embodiments, as illustrated, the spline couplings 2910*a-c* may include stub portions 3010 that extend or protrude from at least the proximal face 3002 of the body 2902. In other examples, one or more of the stub portions 3010 may instead be arranged to extend from the distal face 3004 and/or to extend from both the proximal and distal faces 3002, 3004. The stub portions 3010 each define a receptacle 3012 through which the corresponding splines 1624*a-c* can extend to slidingly engage. Also in the illustrated example, each of the instrument drive outputs 2912*a-c* includes a stub shaft 3014 extending or protruding past the proximal face 3002 and configured to mate with a mating shaft receptacle.

Figure 31:
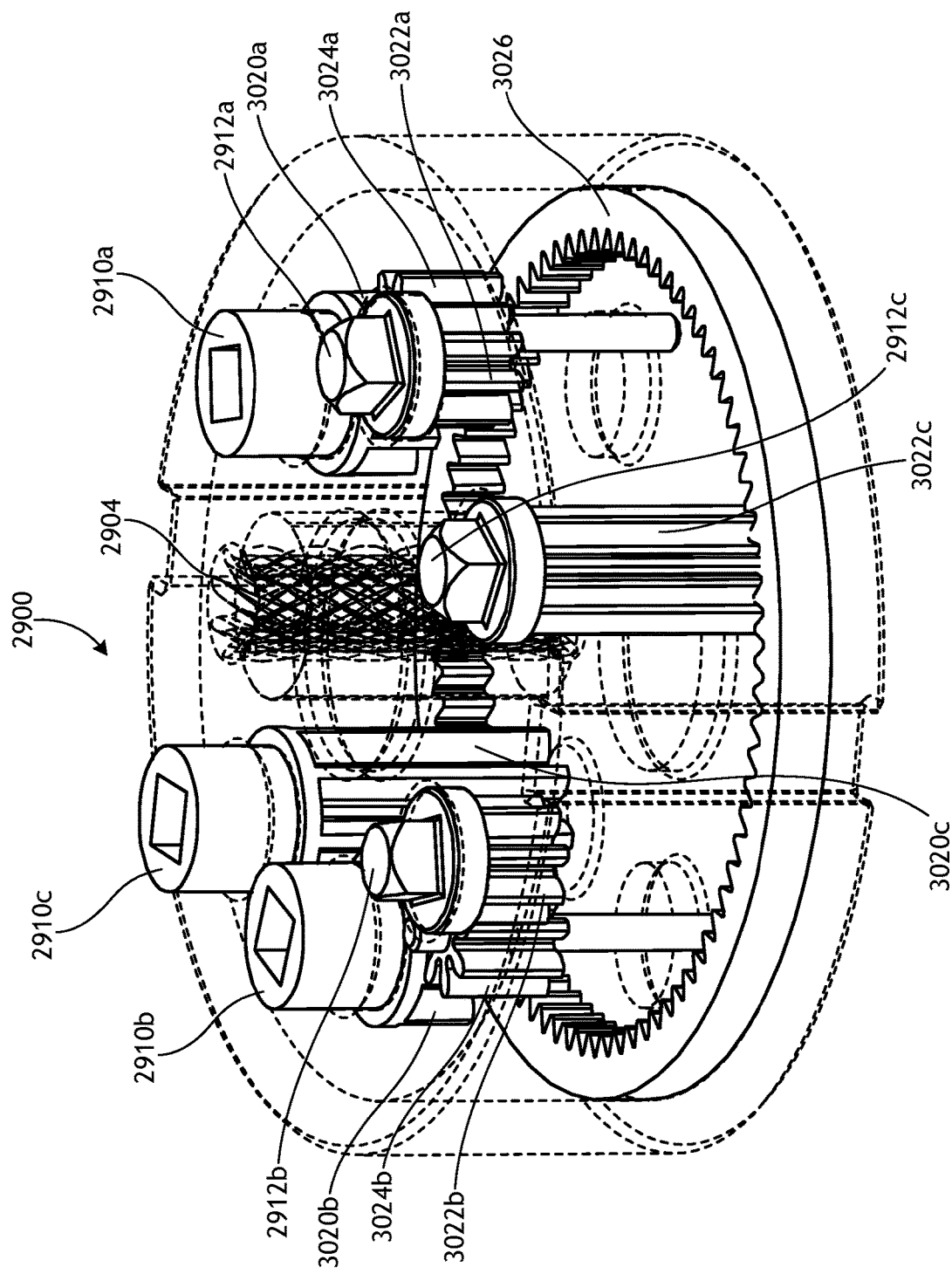
FIG. 31 illustrates internal drive components and gearing arrangeable within the translatable drive puck of FIG. 29, according to one or more embodiments.

FIG. 31 is an isometric top view of the drive puck 2900, according to one or more embodiments. The body 2902 is shown in phantom in FIG. 31 so as to better illustrate how the spline couplings 2910*a-c* may be in operative engagement with the instrument drive outputs 2912*a-c*, according to some embodiments. As briefly mentioned above, various gearing and/or mechanisms may be arranged within the body 2902 to operatively intermesh and/or couple each of the spline couplings 2910*a-c* with the associated instrument drive output 2912*a-c*. As illustrated, each of the spline couplings 2910*a-c* includes a drive gear 3020*a-c* arranged within the interior volume 3008 of the body 2902. Here, each of the drive gears 3020*a-c* is integrally formed with its associated spline coupling 2910*a-c*, but the drive gears 3020*a-c* may be differently connected to their respective spline coupling 2910*a-c*. In addition, each of the instrument drive outputs 2912*a-c* includes a driven gear 3022*a-c*. Here, each of the driven gears 3022*a-c* is integrally formed with its associated instrument drive output 2912*a-c*, but the driven gears 3022*a-c* may be differently connected to its respective instrument drive output 2912*a-c*.

In some embodiments, the drive puck 2900 may further include first and second idler gears 3024*a* and 3024*b* to operatively couple the first and second spline couplings 2910*a,b* with the first and second instrument drive outputs 2912*a,b*, respectively. In the illustrated embodiment, the first and second idler gears 3024*a,b* are arranged within the body 2902. As illustrated, the first idler gear 3024*a* interposes and intermeshes with both the first drive gear 3020*a* and the first driven gear 3022*a* of the first instrument drive output 2912*a*. In this manner, rotation of the first spline 1624*a* causes the first spline coupling 2910*a* and the first drive gear 3020*a* to rotate, which causes the first idler gear 3024*a* to rotate and drive the first driven gear 3022*a* and the first instrument drive output 2912*a*. Similarly, the second idler gear 3024*b* interposes and intermeshes with both the drive gear 3020*b* of the second spline coupling 2910*b* and the driven gear 3022*b* of the instrument drive output 2912*b*. In this manner, rotation of the second spline 1624*b* causes the second spline coupling 2910*b* and the second drive gear 3020*b* to rotate, which causes the second idler gear 3024*b* to rotate and drive the second driven gear 3022*b* and the instrument drive output 2912*b*.

In the illustrated embodiment, the drive puck 2900 also includes a ring gear 3026 arranged to operatively couple the third spline coupling 2910*c* with the third instrument drive output 2912*c*. In other embodiments, however, the third spline coupling 2910*c* and the third instrument drive output 2912*c* may be operatively coupled via a different means, for example, via an idler gear as described above. Where utilized, the ring gear 3026 is arranged to mesh with both the third drive gear 3020*c* of the third spline coupling 2910*c* and the third driven gear 3022*c* of the third instrument drive output 2912*c*. Here, the ring gear 3026 is mounted within the interior volume 3008 of the body 2902 such that the ring gear 3026 is able to rotate relative to the body 2902. As illustrated, the ring gear 3026 extends continuously along an inner circumferential wall of the body 1902 such that it intermeshes with both the drive gear 3020*c* and the driven gear 3022*c*. In this manner, rotation of the third spline 1624*c* and the third spline coupling 2910*c* rotates the third drive gear 3020*c*, which in turn causes the ring gear 3026 to rotate and drive the driven gear 3022*c* meshed therewith to thereby cause rotation of the third instrument drive output 2912*c*.

Thus, the drive puck 2900 may be configured to travel along the splines 1624*a-c* and receive the splines 1624*a-c* at respective spline openings located at a distal (e.g., bottom) side of the body 2902, and transfer the torsional forces (torque) from the splines 1624*a-c* to the corresponding instrument drive outputs 2912*a-c* arranged on an opposite proximal (e.g., top) side of the body 2902 at locations spaced away (or offset) from the associated splines 1624*a-c*.

Figure 32:
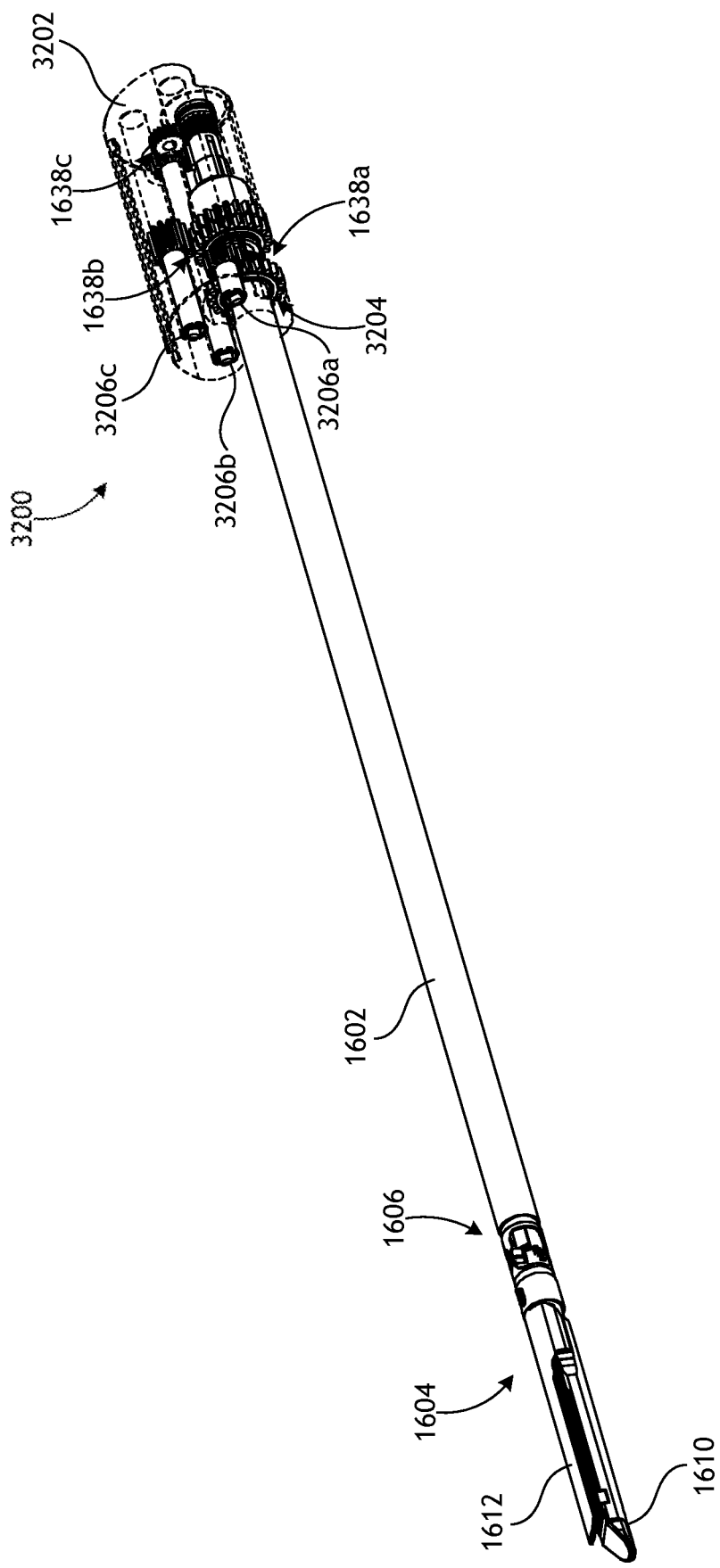
FIG. 32 illustrates a removable handle segment of the surgical tool adapted to be releasably secured on the translatable drive puck, according to one or more embodiments.

FIG. 32 illustrates a portion of the surgical tool 1600 (FIG. 16), according to one or more embodiments. In the illustrated embodiment, the surgical tool 1600 may be segmented into different portions or segments. For example, the surgical tool 1600 may include a stage segment (FIG. 29), which incorporates the drive puck 2900 and its functionality, and may further include a handle segment 3200 mountable to the drive puck 2900 and operatively connected to both the shaft 1602 and the end effector 1604 for actuating the same. The handle segment 3200, the shaft 1602, and the end effector 1604 may all be integrated together as a unit that may be removed from the stage segment, such that a new unit may be installed on the same stage segment. Accordingly, the handle segment 3200, the shaft 1602, and the end effector 1604 may all be integrated together to as a removable segment of the surgical tool 1600, which may be installed and uninstalled from the stage segment (FIG. 29) and replaced with a new removable segment.

In the illustrated embodiment, the handle segment 3200 includes a handle drive housing 3202 having a mounting surface 3204 configured to be mounted on or otherwise mate with the proximal face 3002 (FIG. 30A) of the drive puck 2900 (FIG. 29). In particular, the mounting surface 3204 is configured to mate with and engage the instrument drive outputs 2912*a-c* (FIG. 30A). Thus, the handle drive housing 3202 and the mounting surface 3204 may include geometries corresponding with at least a portion of the drive puck 2900. The housing 3202 is depicted in FIG. 32 in phantom so as to illustrate the various activating mechanisms contained within the housing 3202.

Figure 33:
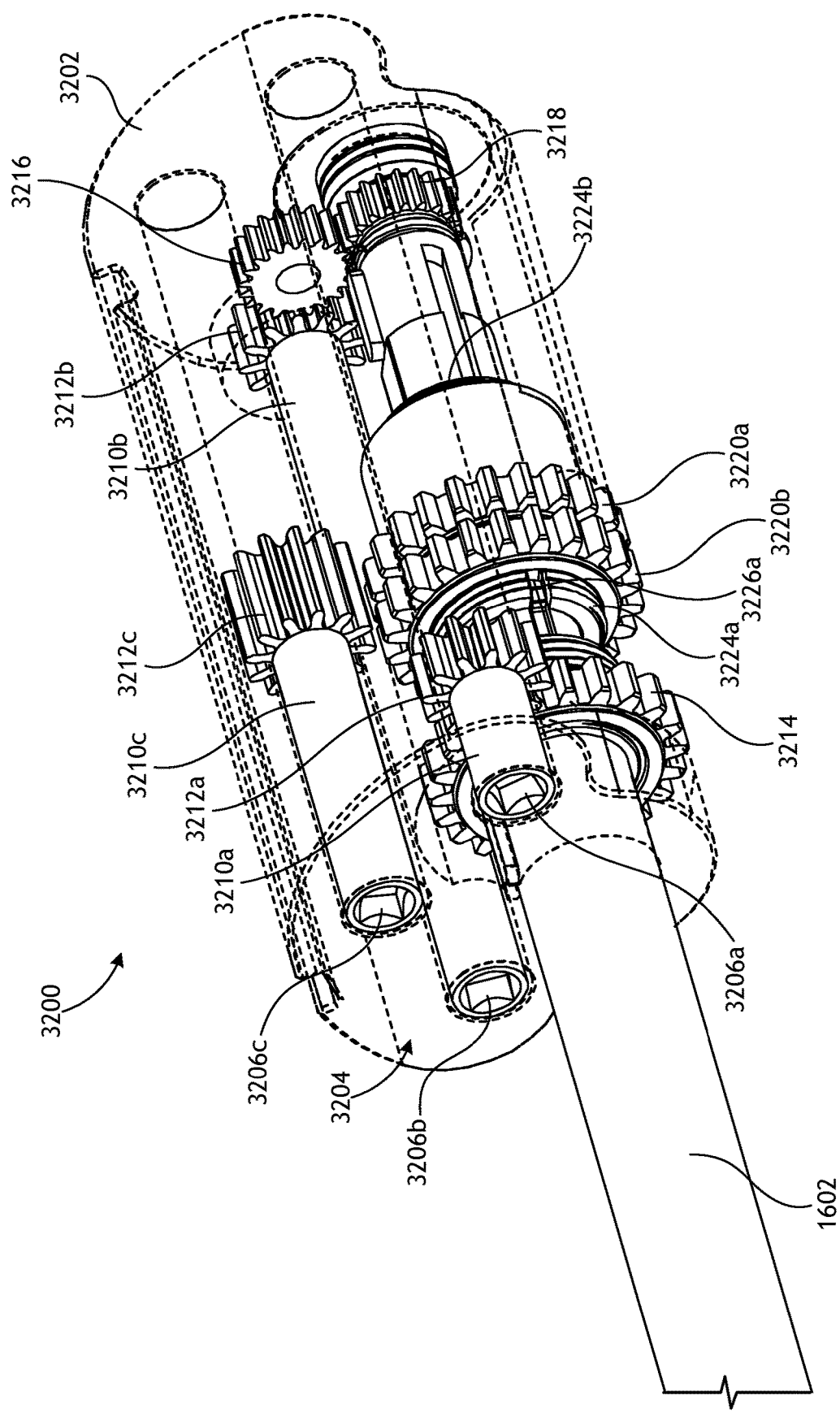
FIG. 33 is a close up of the removable handle segment of FIG. 32 illustrating exemplary internal drive mechanisms, according to one or more embodiments.

FIG. 33 is an enlarged isometric view of the handle segment 3200 with the housing 3202 shown in phantom to further illustrate exemplary operation, according to one or more embodiments. A plurality of drive inputs 3206*a-c* are provided or otherwise defined in the mounting surface 3204. In the illustrated example, three drive inputs 3206*a-c* are provided to communicate with and engage the instrument drive outputs 2912*a-c* (FIG. 30A) of the drive puck 2900 (FIG. 29), and thereby actuate the end effector 1604. However, more or less than three drive inputs 3206*a-c* may be provided if the drive puck 2900 includes more or less than three instrument drive outputs 2912*a-c*. As illustrated, each drive input 3206*a-c* defines or otherwise provides a receptacle having a geometry that corresponds to the geometry of the associated instrument drive output 2912a-c so as to be able to transfer torsional forces (torque) therebetween.

The first drive input 3206a may be operatively coupled to or form part of the first activating mechanism 1638a, which operates to open and close the jaws 1610, 1612. Accordingly, rotating the first drive input 3206a will correspondingly actuate the first activating mechanism 1638a and thereby open or close the jaws 1610, 1612, depending on the rotational direction of the first instrument drive output 2912a. Similarly, the second drive input 3206b may be operatively coupled to the second activating mechanism 1638b, which operates to articulate the end effector 1604 at the wrist 1606. Accordingly, rotating the second drive input 3206b will correspondingly actuate the second activating mechanism 1638b and cause the wrist 1606 to articulate in at least one degree of freedom, depending on the rotational direction of the second instrument drive output 2912b. In addition, the third drive input 3206c may be operatively coupled to the third activating mechanism 1638c, which operates to fire the cutting element at the end effector 1604. Accordingly, rotating the third drive input 3206c will correspondingly actuate the third activating mechanism 1638c and cause the knife to advance or retract, depending on the rotational direction of the third instrument drive output 2912c.

In the illustrated embodiment, the drive inputs 3206a-c each include a respective shaft 3210a-c that extends proximally into the housing 3202 and is connected to a respective drive gear 3212a-c. Also, each drive gear 3212a-c is arranged to engage the activating mechanism 1628a-c associated with it. Alternatively, as indicated above, the drive gears 3212a-c may each form an integral part of the corresponding activating mechanism 1628a-c.

Here, the first drive gear 3212a is intermeshed with a driven gear 3214 of the first activating mechanism 1638a. The driven gear 3214 may be internally threaded and arranged about an externally threaded portion of the shaft 1602, such that rotation of the internally threaded driven gear 3214 via rotation of the first drive inputs 3206 threadably engages the externally threaded portion of the shaft 1602 and thereby drives the shaft 1602 axially to open and/or close the jaws 1610, 1612 (FIG. 32). The second drive gear 3212b may be arranged to engage a pinion or idler gear 3216, which is operatively intermeshed between the second drive gear 3212b and a driven gear 3218 of the third activating mechanism 1638c to thereby effectuate firing of the cutting means of end effector 1604. The third drive gear 3212c may be arranged to intermesh with a pair of internally threaded driven gears 3220a,b of the second activating mechanism 1638b. The pair of internally threaded driven gears 3220a,b have opposite thread patterns and are arranged about corresponding threaded carriers 3224a and 3224b, which translate in opposing axial directions upon rotation of the internally threaded driven gears 3220a,b. This causes a pair of linearly translatable internal drive rods 3226a (one shown) to antagonistically move distally or proximally. The internal drive rods 3226a are operatively coupled to the wrist 1606, and the antagonistic push and pull of the drive rods operate to control articulation of the wrist 1606.

Figure 34:
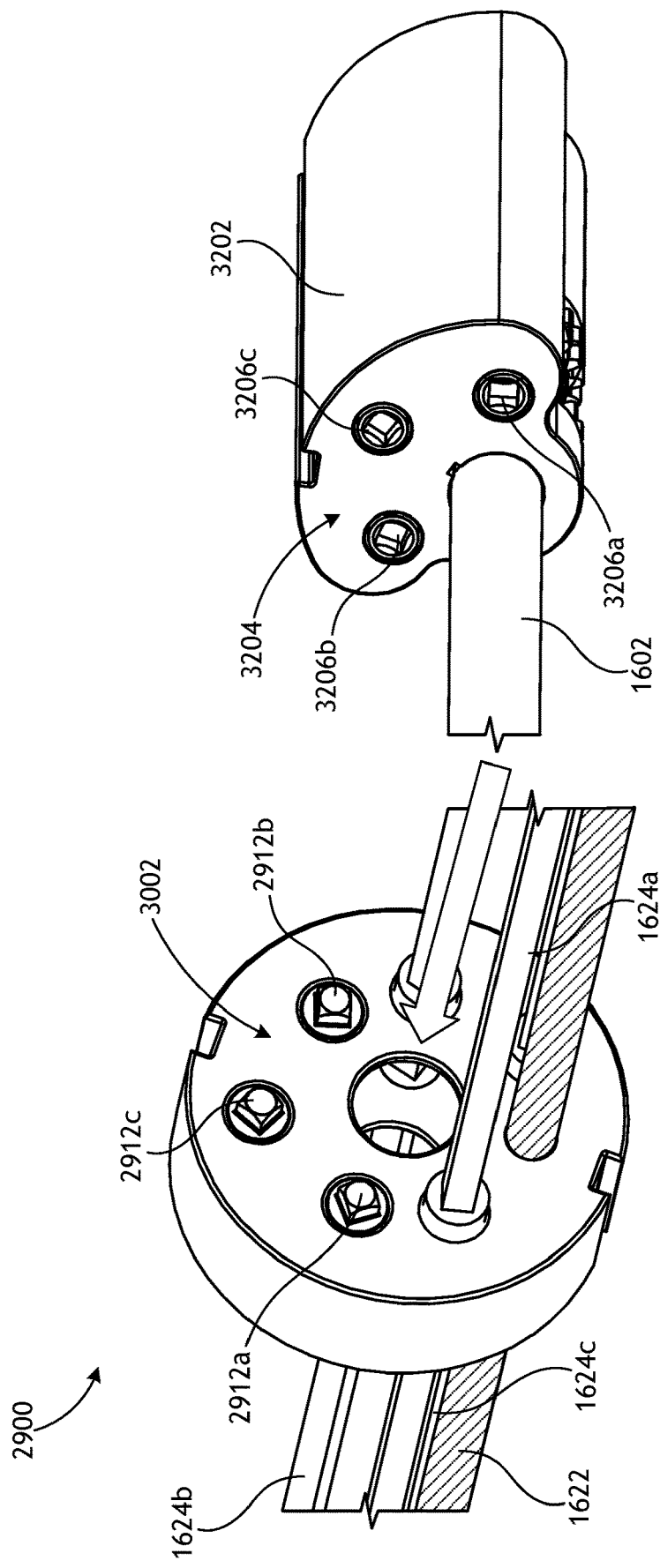
FIG. 34 illustrates how the removable portion may be aligned with the drive puck during installation.

FIG. 34 illustrates an exemplary alignment between the handle segment 3200 and the drive puck 2900 when installing the removable segment of the surgical tool 1600, according to one or more embodiments. In the illustrated embodiment, the first instrument drive output 2912a is alignable and matable with the first drive input 3206a, the second instrument drive output 2912b is alignable and matable with the second drive input 3206b, and the third instrument drive output 2912c is alignable and matable with the third drive input 3206c. Moreover, the shaft 1602 is extendable through the bore 3006.

As discussed above, the drive inputs 3206a-c are driven by the instrument drive outputs 2912a-c, which are driven indirectly from locations corresponding with the splines 1624a-c with internal gearing. In other examples, the drive puck 2900 may include just two instrument drive outputs 2912 driven indirectly from their associated splines with internal gearing. Moreover, in some of these examples, the drive puck 2900 may also be configured to permit direct drive of the handle segment 3200. For example, the handle segment 3200 may have two or more inputs corresponding with and driven by the indirectly driven elevator outputs of the drive puck 2900, and the handle segment 3200 may also include one or more inputs each directly activated by an additional spline (unaffiliated with an indirectly driven elevator output), such that two or more inputs of the handle segment 3200 are indirectly driven by the drive puck 2900 and one or more other inputs of the handle segment 3200 are directly driven by splines.

Accordingly, the drive puck 2900 transfers (or maps) the drive position of the handle segment portion 3200 to locations offset from (or unassociated or unaligned with) the splines 1624a-c. While the drive puck 2900 has been described with reference to gearing that mechanically connects the splines 1624a-c with the associated instrument drive outputs 2912a-c, different means may be utilized to transfer input of the splines 1624a-c to the instrument drive outputs 2912a-c. For example, the splines 1624a-c may be mechanically connected to the instrument drive outputs 2912a-c with belts or other mechanisms. Locating the instrument drive outputs 2912a-c at drive positions unassociated with the splines 1624a-c to which they are mechanically connected provides greater flexibility when designing the geometry of the handle segment portion 3200 and/or the shroud 1640.

Figure 35:
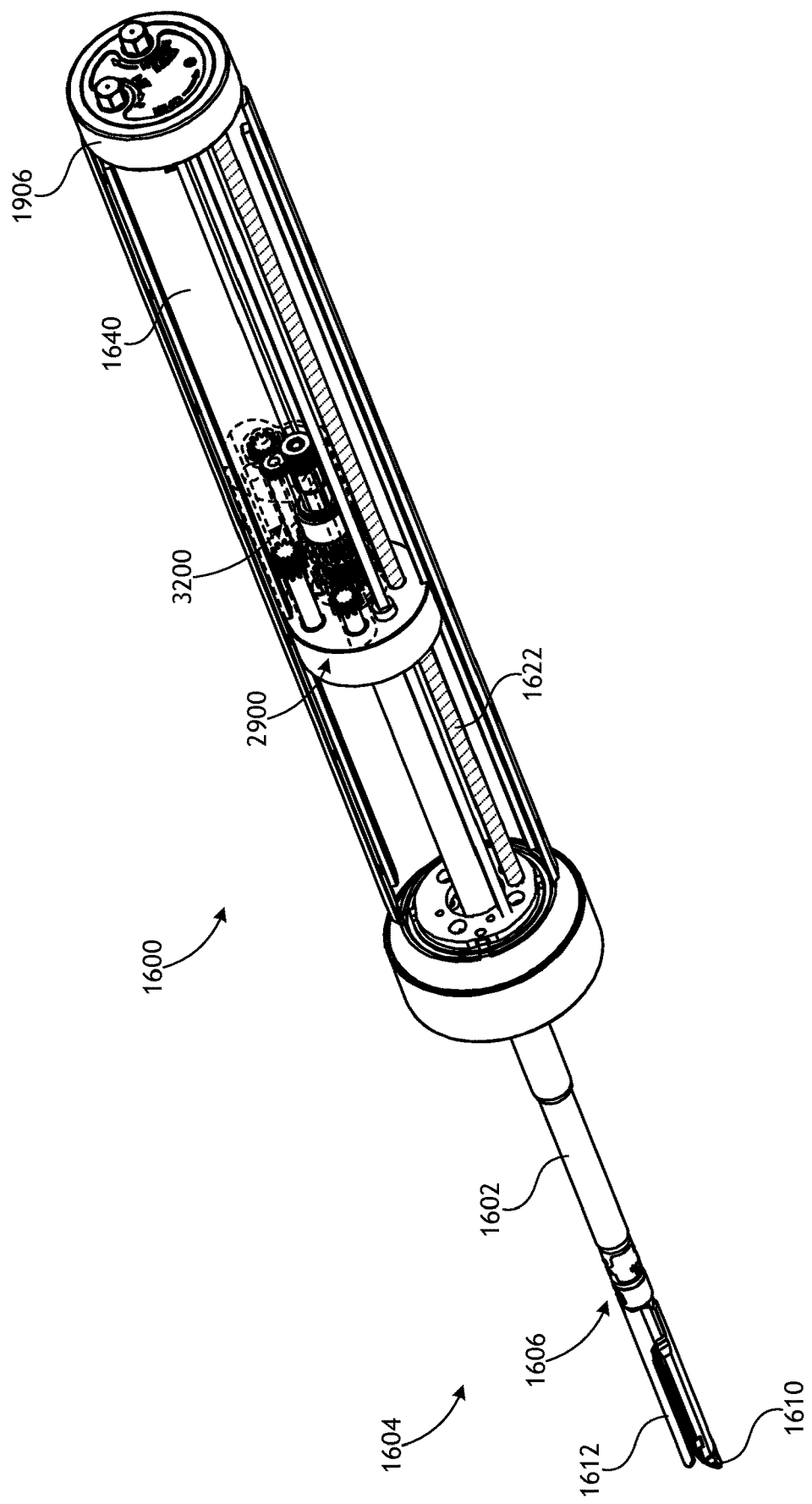
FIG. 35 illustrates the surgical tool wherein the removable handle segment of FIG. 32 has been installed within the stage of FIG. 29.

FIG. 35 illustrates the surgical tool 1600 with the handle segment 3200 installed on the drive puck 2900 of the stage segment. Here, the shaft 1602 is extended through the bore 3006 in the drive puck 2900 and the mounting surface 3204 of the handle drive housing 3202 (FIG. 34) is positioned on the proximal face 3002 (FIG. 34) of the drive puck 2900. In particular, the handle segment 3200 is positioned on the drive puck 2900 such that the drive inputs 3206a-c are in alignment with the instrument drive outputs 2912a-c of the drive puck 2900.

Surgical Tool with Removable Instrument Core

FIG. 36 illustrates another example embodiment of the surgical tool 1600, according to various embodiments. As mentioned above, the surgical tool 1600 may be assembled by removing the removable cap 1906 and then mounting the handle segment 3200 (FIG. 32) on the drive puck 2900 (FIG. 29), which functions as the stage portion 1902 (FIG. 19) of the surgical tool 1600, as exemplified in FIGS. 34-35. In other embodiments, the surgical tool 1600 may be configured such that at least a portion of the instrument portion 1904 (FIG. 19) is an interchangeable sub-assembly (or core) that may be installed on the stage portion 1902. For example, the handle assembly 1908, the elongated shaft 1902, and the end-effector 1604 of the removable instrument portion 1904 may be integrated together as an interchangeable core of the surgical tool 1600 that may be dropped straight onto (or angled onto) the stage portion 1902 without having to remove the removable cap 1906.

In FIG. 36, the surgical tool 1600 includes or otherwise incorporates a handle sub-assembly or handle core 3602 configured to be dropped or angled (or arced) into (i.e., installed in) a stage sub-assembly 3604. In this illustration, the shroud 1640 (FIG. 17) has been removed so as to more easily illustrate the stage sub-assembly 3604. The handle core 3602 (hereinafter, the core 3602) is an assembly that generally comprises the instrumentation componentry and therapeutic and/or diagnostic features of the surgical tool 1600. Thus, as illustrated, the core 3602 may include the shaft 1602, the end effector 1604, and the operational engagement features configured to affect movement and functionality of the end effector 1604 when engaged by the stage sub-assembly 3604.

In the illustrated embodiment, the stage sub-assembly 3604 includes a carriage or kart 3606 configured to translate between the first and second ends 1618a,b. Thus, the carriage 3606 may include a carriage nut or kart nut (obscured from view) that is operatively engaged with the lead screw 1622 such that rotation of the lead screw 1622 translates the carriage 3606 along the lead screw 1622. The splines 1624a-c may be arranged within a lower half (e.g., 180°) of the stage sub-assembly 3604 and extend through the carriage 3606. Thus, the carriage 3606 may include spline channels extending therethrough for receiving the splines 1624a-c such that the splines 1624a-c may rotate within the spline channels as the carriage 3606 translates along the lead screw 1622. As more fully described below, spline couplings may be arranged within each of the spline channels, where the spline couplings each receive a corresponding spline 1624a-c such that they rotate in unison with their respective spline 1624a-c, and the spline couplings are axially constrained within their respective spline channels such that the spline couplings may slide along the splines 1624a-c as the carriage 3606 axially translates.

In addition, the stage sub-assembly 3604 includes a pair of guide rails 3608a,b extending between the first and second ends 1618a,b. The guide rails 3608a,b extend substantially parallel with the splines 1624a-c of the stage sub-assembly 3604, and help facilitate installation of the core 3602 on the carriage 3606. Moreover, the guide rails 3608a,b guide the core 3602 as it is carried by the carriage 3606 when translating proximally or distally between the first and second ends 1618a,b. In this example, the guide rails 3608a,b are unconstrained by the carriage 3606. More specifically, the carriage 3606 is generally U-shaped and defines a trough 3610 (or space or void) sized and shaped to receive the core 3602 in a nested relationship and also constrain the core 3602 installed therein such that the carriage 3606 carries the core 3602 as the carriage 3606 translates between the first and second ends 1618a,b.

Also in the illustrated embodiment, the core 3602 includes a pair of arms or wings 3612a,b laterally extending from a drive housing or body 3614 of the core 3602, where the arms 3612a,b are configured to be releasably attached to the guide rails 3608a,b. In some embodiments, the arms 3612a,b rest on the guide rails 3608a,b. In some embodiments, the arms 3612a,b may be configured to slidingly snap onto the guide rails 3608a,b when the body 3614 of the core 3602 is positioned in the trough 3610 in the carriage 3606, such that the arms 3612a,b retain the body 3614 on the rails 3608a,b while translating between the first and second ends 1618a,b. In some embodiments, the arms 3612a,b may include locking toggle levers configured to slidingly attach the arms 3612a,b on the guide rails 3608a,b when the body 3614 of the core 3602 is positioned in the trough 3610 in the carriage 3606. In some embodiments, the arms 3612a,b include semicircular closure members that rotate and close around the rails 3608a,b upon activation of a locking switch. In one non-illustrated embodiment, one or more of the drive splines operate as the guide rail on which the core 3602 is positioned, for example, the arms 3612a,b may be attachable on the first and second spline 1624a,b that engage a respective drive function, such as the drive gears 3212a-c (FIG. 33).

FIG. 37 is a schematic diagram depicting example installation of the core 3602 to the stage sub-assembly 3604 of FIG. 36. As illustrated, the core 3602 may be dropped on or angled into the stage sub-assembly 3604. As the core 3602 descends, the arms 3612a,b may be aligned to receive the guide rails 3608a,b, and thus resting the core 3602 on the guide rails 3608a,b. In addition, the body 3614 includes operative engagement features for actuating the shaft 1602 (FIG. 36) and the end effector 1604 (FIG. 36). In the illustrated examples, the core 3602 is configured to interface with the spline couplings within the carriage 3606 so as to control operation of the end effector 1604. For example, the carriage 3606 may slide on the splines 1624a-c with gears within the carriage driven by and translating on the splines 1624a-c that interface with the operative engagement features in the body 3614, such as the drive gears 3212a-c (FIG. 33).

Figure 38:
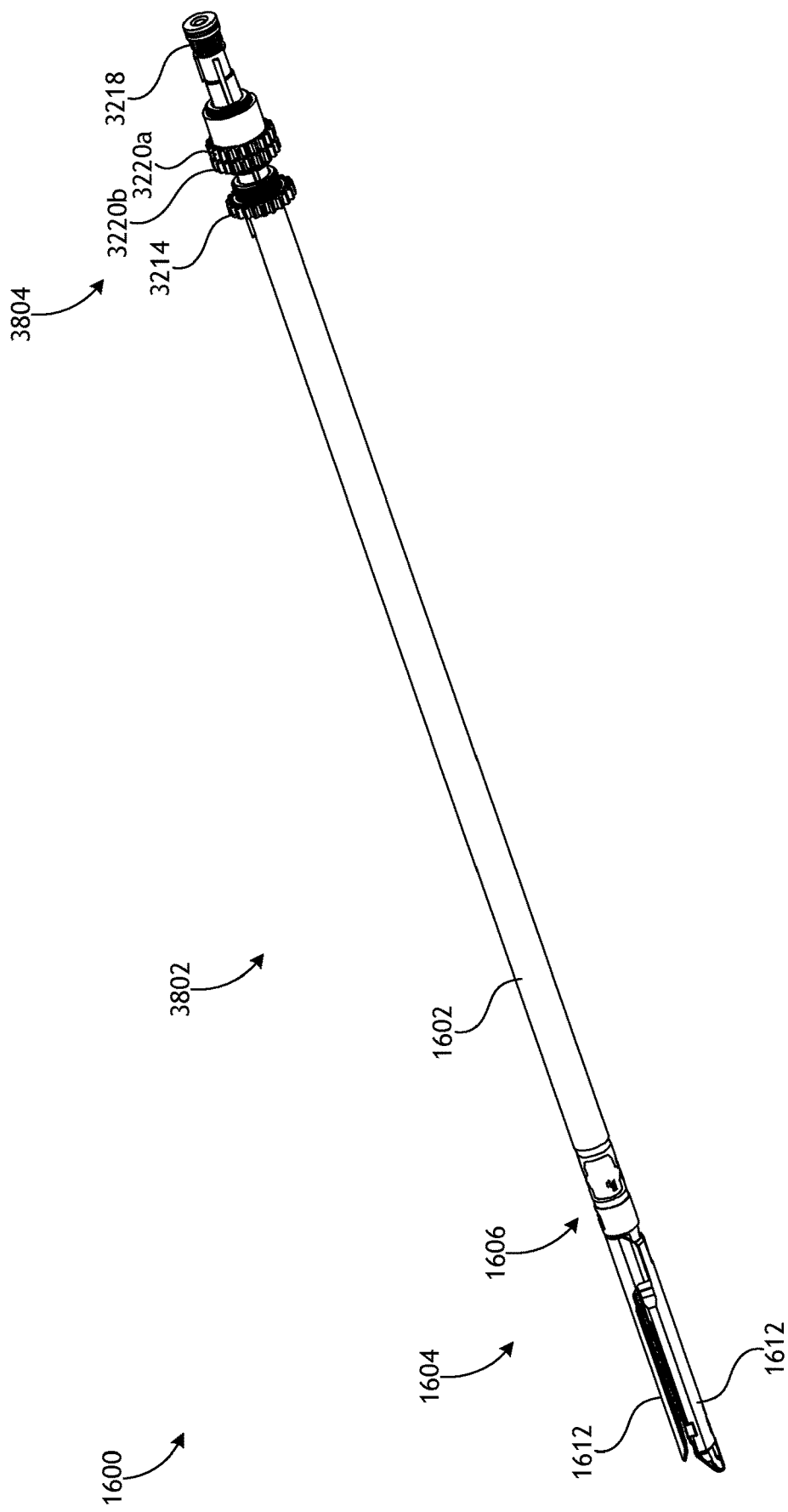
FIG. 38 illustrates a core assembly of the surgical tool, according to various other embodiments.
Figure 39:
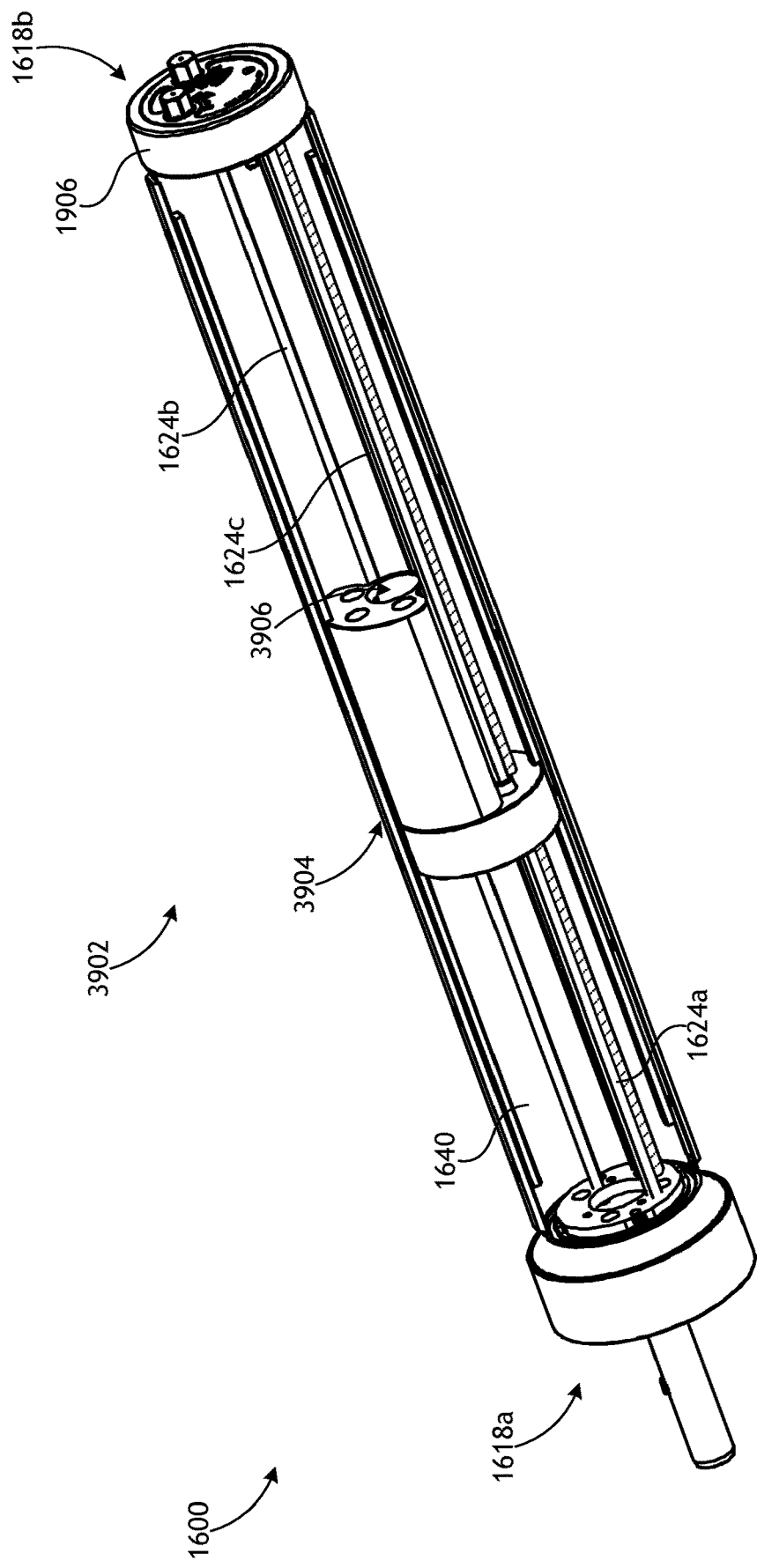
FIG. 39 illustrates an exemplary stage assembly on which the core assembly of FIG. 38 may be mounted.

FIGS. 38 and 39 illustrate another example of the surgical tool 1600 incorporating a handle sub-assembly or handle core 3802 configured to be dropped into a stage assembly 3902, according to various embodiments. In FIG. 38, the core 3802 is illustrated when removed from the stage assembly 3902 (FIG. 39), whereas FIG. 39 illustrates the stage assembly 3902 without the core 3802 (FIG. 38) installed therein. The handle core 3802 (hereinafter, the handle 3802) is an assembly that generally comprises the instrumentation componentry and therapeutic and/or diagnostic features of the surgical tool 1600. Thus, as illustrated, the core 3802 may include a drive end 3804, the elongate shaft 1602 which extends from the drive end 3804, the end effector 1604, the wrist 1606, the jaws 1610,1612, and the various operational engagement features configured to affect movement and functionality of the end effector 1604 when engaged by the stage assembly 3902. The drive end 3804 includes the various drive elements configured to manipulate the various functionality of the end effector 1604, such as opening and closing of the jaws 1610,1612, articulation of the wrist 1606, and firing of the end effector 1604. Here, the drive end 3804 includes the driven gear 3214 of the first activating mechanism 1638a (FIG. 32), the pair of internally threaded driven gears 3220a,b of the second activating mechanism 1638b, and the driven gear 3218 of the third activating mechanism 1638c. As shown in FIG. 39, the stage assembly 3902 includes a carriage or cart 3904, configured to translate between the first and second ends 1618a,b as described herein. Accordingly, the carriage 3904 may be referred to as the elevator. The carriage 3904 includes a central opening or bore 3906. When the removable cap 1906 is removed, the core 3802 may be dropped into the stage assembly 3902, with the elongate shaft 1602 being inserted, along the longitudinal axis $A_1$ (FIG. 16), through the bore 3906 and through an opening at the first end 1618a of the stage assembly 3902 leading into the alignment nozzle 1812 (FIG. 16), such that the drive end 3804 is positioned within the bore 3906 and thereby operatively coupling the various drive elements of the drive end 3804 with the associated splines 1624a-c. In this manner, when the drive end 3804 is engaged within the bore 3906 of the carriage 3904, the driven gear 3214 of the first activating mechanism 1638a will be coupled with the first spline 1624a, the pair of internally threaded driven gears 3220a,b of the second activating mechanism 1638b will be coupled with the second spline 1624b, and the driven gear 3218 of the third activating mechanism 1638c will be coupled with the third spline 1624c. Thus, the core 3802 may be installed on the stage assembly 3902 by axially inserting the core 3802 into and through the stage assembly 3902.

Figure 41:
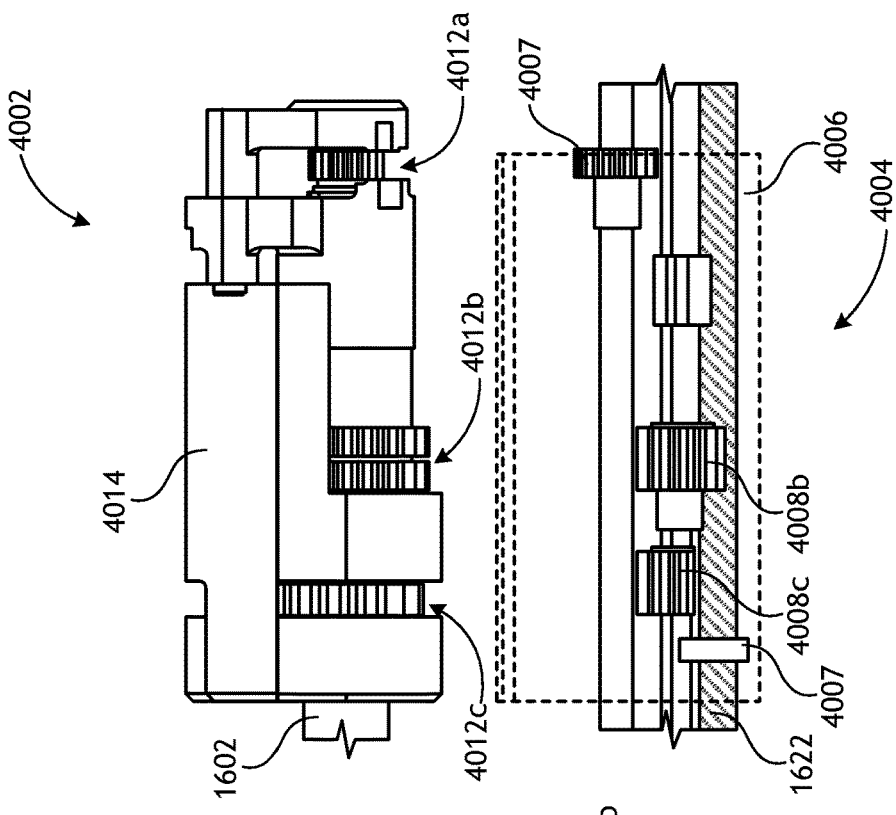
FIG. 41 is a cross-sectional side view of a portion of the handle sub-assembly and the stage sub-assembly shown in FIG. 40.
Figure 40:
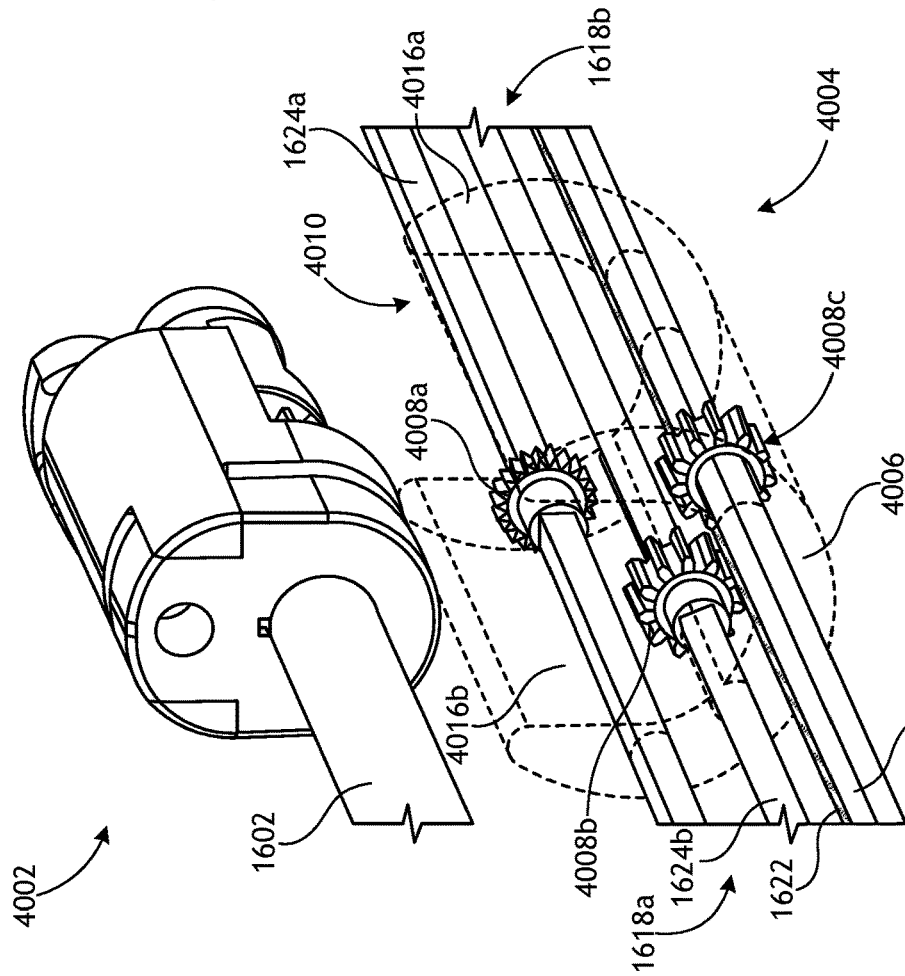
FIG. 40 illustrates the surgical tool incorporating yet another alternate handle sub-assembly configured to be dropped on or angled into a stage sub-assembly, according to various embodiments.

FIGS. 40 and 41 illustrate another example of the surgical tool 1600 incorporating a handle sub-assembly or handle core 4002 configured to be dropped or angled into a stage sub-assembly 4004, according to various embodiments. FIG. 40 is an isometric view of a portion of the handle core 4002 (hereinafter, the core 4002) when removed from the stage sub-assembly 4004, according to various embodiments, and FIG. 41 is a side view of the portion of the core 4002 and the stage sub-assembly 4004 shown in FIG. 40.

In the illustrated embodiment, the stage sub-assembly 4004 includes a carriage or kart 4006 configured to translate between the first and second ends 1618a,b (FIGS. 36 and 38). Thus, the carriage 4006 may include a carriage nut 4007 that is operatively engaged with the lead screw 1622 such that rotation of the lead screw 1622 translates the carriage 4006 along the lead screw 1622. As illustrated, the splines 1624a-c extend through the carriage 4006. Thus, the carriage 4006 may include spline channels extending therethrough for operatively receiving the splines 1624a-c such that the splines 1624a-c may rotate within the spline channels of the carriage 4006 as the carriage 4006 translates along the lead screw 1622. In the illustrated embodiment, the splines 1624a-c and their corresponding spline channels are arranged within a lower one-hundred and eighty degrees of the stage sub-assembly 4004 and the carriage 4006 to facilitate installation of the core 4002 onto the stage sub-assembly 4004.

Drive gears 4008a-c may be rotatably mounted to the carriage 4006 and slidingly arranged on each of the splines 1624a-c such that the drive gears 4008a-c may slide along the respective spline 1624a-c while rotating in unison with the associated spline 1624a-c. The drive gears 4008a-c may be constrained by the carriage 4006 such that they may rotate with their respective spline 1624a-c while translating with the carriage 4006. Here, the drive gears 4008a-c are aligned with a corresponding spline channel to slidingly receive their corresponding splines 1624a-c. The drive gears 4008a-c rotate in unison with their respective spline 1624a-c while being axially constrained relative to the carriage 4006 such that they may slide over the splines 1624a-c as the carriage 4006 translates. Thus, the first drive gear 4008a is configured to slide axially along while rotating in unison with the first spline 1624a, the second drive gear 4008b is configured to slide axially along while rotating in unison with the second spline 1624b, and the third drive gear 4008c is configured to slide axially along while rotating in unison with the third spline 1624c.

The carriage 4006 may be configured to provide a trough 4010 (or space or void) within which the core 4002 may be mounted. In the illustrated example, the carriage 4006 defines a trough 4010 sized and shaped to receive the core 4002. Here, the carriage 4006 constrains the core 4002 once mounted in the trough 4010, such that the carriage 4006 carries the core 4002 as it translates. While the carriage 4006 is illustrated having a generally U-shaped geometry, it may exhibit different geometries, without departing from the present disclosure. For example, the carriage 4006 may include a circular shaped opening for receiving a drive end with drive elements of a drop-in core, such as the core 3802 described with reference to FIGS. 38-39.

The drive gears 4008a-c of the carriage 4006 are each configured to drive, engage, and interact with a corresponding activating mechanism 4012a-c of the core 4002. The activating mechanisms 4012a-c may be arranged at various locations along the axial length of a drive housing or body 4014 of the core 4002. In the illustrated example, the first activating mechanism 4012a is located at or near a proximal end of the body 4014, the third activating mechanism 4012c is located at or near a distal end of the body 4014, and the second activating mechanism 4012b is located between the first and third activating mechanisms 4012a,c. As will be appreciated, the activating mechanism 4012a-c may be located differently, depending on the application.

In some embodiments, one or more of the drive gears 4008a-c (and/or their teeth or cogs) may extend into the trough 4010 to engage (intermesh) the corresponding activating mechanism 4012a-c of the core 4002. In other embodiments, however, one or more of the drive gears 4008a-c may be recessed within the body of the carriage 4006 and the corresponding activating mechanisms 4012a-c may extend to engage the drive gears 4008a-c. In the illustrated example, the first drive gear 4008a, which is slidingly arranged on the first spline 1624a, is configured to mesh with the first activating mechanism 4012a such that rotation of the first spline 1624a correspondingly actuates the first activating mechanism 4012a and thereby carries out a first function of the surgical tool 1600 (e.g., to fire a cutting element). The second drive gear 4008b, which is slidingly arranged on the second spline 1624b, is configured to mesh with the second activating mechanism 4012b such that rotation of the second spline 1624b correspondingly actuates the second activating mechanism 4012b and thereby carries out a second function of the surgical tool 1600 (e.g., to articulate the wrist 1606 of FIG. 35). Lastly, the third drive gear 4008c, which is slidingly arranged on the third spline 1624c, is configured to mesh with the third activating mechanism 4012c such that rotation of the third spline 1624c correspondingly actuates the third activating mechanism 4012c and thereby carries out a third function of the surgical tool 1600 (e.g., to open or close the jaws 1610, 1612 of FIG. 35).

Various means may be utilized to retain the body 4014 of the core 4002 within the carriage 4006 of the stage sub-assembly 4004. In some examples, the carriage 4006 includes a pair of sidewalls 4016a,b on either side of the trough 4010, and the sidewalls 4016a,b may be biased or otherwise angled inward so as to retain the body 4014 when the body 4014 is inserted therein. In such embodiments, the core 4002 may be received within the trough 4010 via a snap-fit or interference fit engagement. However, other means may be utilized to releasably secure the body 4014 to the carriage 4006, for example, various types of mechanical fasteners, snaps, magnets, Velcro, etc. In other embodiments, a closure band or shroud portion may rotate about the shroud 1640 (FIG. 35) to constrain and enclose the body 4014 on the carriage 4006.

FIGS. 42A-42D depict various alternative embodiments of the shroud 1640 that may form part of the surgical tool 1600 of FIG. 16. More specifically, FIGS. 42A-42D illustrate example shroud assemblies configured to open and close such that a handle core or handle sub-assembly (e.g., the core 3602, 3802, 4002 of FIGS. 36-37, FIGS. 38-39, and/or FIGS. 40-41, respectively) may be easily installed on a stage sub-assembly (e.g., the stage sub-assembly 3604, 3804, 4004 of FIGS. 36-37, FIGS. 38-39, and/or FIGS. 40-41, respectively).

FIG. 42A illustrates a shroud assembly 4200 wherein the shroud 1640 thereof defines an opening 4202 configured to receive a handle sub-assembly, according to one or more embodiments. In the illustrated example, the opening 4202 in the shroud 1640 corresponds to the shape of a handle sub-assembly intended to be inserted (introduced) into the shroud 4204. Thus, the opening 4202 includes an enlarged portion 4204 corresponding in size and shape to the body of the handle sub-assembly (e.g., the body 3614, 3814, 4014 of FIGS. 36-37, FIGS. 38-39, and FIGS. 40-41, respectively) and a narrow portion 4206 that extends distally from the enlarged portion and is sized and shaped to receive the shaft 1602 (FIGS. 36, 38, and 40) and the end effector 1604 (FIGS. 36, 38, and 40) of the handle sub-assembly. Accordingly, the handle sub-assembly may be dropped or angled into the stage sub-assembly through the opening 4202.

In some embodiments, a secondary shroud may be provided to selectively cover the opening 4202, such that the handle sub-assembly may be fully enclosed and/or sealed from the ambient environment when installed on the stage sub-assembly. For example, FIGS. 42B-42D illustrate different embodiments of the shroud assembly 4200 having a secondary shroud configured to selectively enclose and seal the opening 4202 in the shroud 1640.

FIG. 42B illustrates another embodiment of the shroud assembly 4200, according to one or more embodiments. In particular, FIG. 42B illustrates an example of the shroud assembly 4200 having a secondary shroud 4210 configured to slide over the opening 4202 in the shroud 1640. In the illustrated embodiment, the shroud 1640 is generally cylindrical in shape and the secondary shroud 4210 is an arcuate member having a curvature substantially similar to the curvature of the shroud 1640 and sized to occlude the opening 4202 in the shroud 1640. In some embodiments, the secondary shroud 4210 is provided with a curvature that is generally concentric with the shroud 1640 when the secondary shroud 4212 is slidingly attached (or coupled) to the shroud 1640.

The secondary shroud 4210 may be able to move (slide) relative to the inner or outer circumference of the shroud 1640. In the illustrated embodiment, the secondary shroud 4212 is slidingly disposed over an exterior surface (i.e., the outer circumference) of the shroud 1640 such that the secondary shroud 4212 may circumferentially revolve (rotate) over the shroud in a closure direction C; however, in other embodiments, the secondary shroud 4212 may be slidingly disposed within an interior (i.e., the inner circumference) of the shroud 1640 such that the secondary shroud 4212 circumferentially revolves (rotates) within the shroud 1640. In this manner, the secondary shroud 4210 may overlap a portion of the shroud 1640 by sliding on the perimeter or circumference of the shroud 1640 and thereby expose or occlude the opening 4202.

In some embodiments, the secondary shroud 4210 may slide or revolve on the shroud 1640 between an open position, where the opening 4202 is at least partially exposed, and a closed position, where the secondary shroud 4210 occludes the opening 4202. Here, the secondary shroud 4210 is shown in an open position such that the opening 4202 is exposed, but the secondary shroud 4210 may be angularly rotated and slid circumferentially relative to the shroud 1640 in the closure direction C to cover the opening 4202. Thus, the secondary shroud 4210 may be circumferentially revolvable (rotatable) relative to the shroud 1640 between open and closed positions.

FIG. 42C illustrates another embodiment of the shroud assembly 4200, according to one or more embodiments. In particular, FIG. 42C illustrates an example of the shroud assembly 4200 having a secondary shroud 4212 pivotably attached to the shroud 1640. More specifically, the secondary shroud 4212 may be pivotably attached to the shroud 1640 at a hinge 4213 that allows the secondary shroud 4212 to pivot or rotate relative to the shroud 1640 between open and closed positions. The hinge 4213 pivotably attaches the secondary shroud 4212 to the shroud 1640 at a distal location of the shroud 1640 such that the secondary shroud 4212 may be pivoted upward to an open position, where at least a portion of the opening 4202 is sufficiently exposed for dropping or angling the handle sub-assembly into the opening 4202. Thereafter, the secondary shroud 4212 may be pivoted downward into a closed position to occlude and possibly seal the opening 4202. In the illustrated embodiment, the secondary shroud 4212 is shown in an open position, where the opening 4202 is exposed for the handle sub-assembly to be angled or dropped there-into, but the secondary shroud 4212 may be pivoted downward in the closure direction C to thereby close the shroud assembly 4200 and cover the opening 4202.

FIG. 42D illustrates another example embodiment of the shroud assembly 4200 having a secondary shroud 4214 configured to slide axially over the shroud 1640 to expose or occlude the opening 4202, according to one or more embodiments. In the illustrated embodiment, the secondary shroud 4214 is a tubular-shaped member arranged to slide axially over the shroud 1640. In particular, the secondary shroud 4214 may slide proximally into an open position where the opening 4202 is at least partially exposed, or the secondary shroud 4214 may slide distally into a closed position where the secondary shroud 4214 at least partially covers the opening 4202. In the illustrated embodiment, the secondary shroud 4214 is axially slidable over an external surface of the shroud 1640, but in other embodiments, the secondary shroud 4214 may be axially slidable (telescope) within an interior of the shroud 1640. Here, the secondary shroud 4214 is illustrated in an open position, where the opening 4202 is exposed for the handle sub-assembly to be angled or dropped there-into, but the secondary shroud 4214 may be axially slid in the closure direction C to thereby close the shroud assembly 4200 and cover the opening 4202. Thus, the secondary shroud 4214 may be configured to be axially slidable (or telescoping) relative to the shroud 1640 between open and closed positions.

4. Implementing Systems and Terminology.

Implementations disclosed herein provide systems, methods and apparatus for instruments for use with robotic systems. It should be noted that the terms "couple," "coupling," "coupled" or other variations of the word couple as used herein may indicate either an indirect connection or a direct connection. For example, if a first component is "coupled" to a second component, the first component may be either indirectly connected to the second component via another component or directly connected to the second component.

The methods disclosed herein comprise one or more steps or actions for achieving the described method. The method steps and/or actions may be interchanged with one another without departing from the scope of the claims. In other words, unless a specific order of steps or actions is required for proper operation of the method that is being described, the order and/or use of specific steps and/or actions may be modified without departing from the scope of the claims.

As used herein, the term "plurality" denotes two or more. For example, a plurality of components indicates two or more components. The term "determining" encompasses a wide variety of actions and, therefore, "determining" can include calculating, computing, processing, deriving, investigating, looking up (e.g., looking up in a table, a database or another data structure), ascertaining and the like. Also, "determining" can include receiving (e.g., receiving information), accessing (e.g., accessing data in a memory) and the like. Also, "determining" can include resolving, selecting, choosing, establishing and the like.

The phrase "based on" does not mean "based only on," unless expressly specified otherwise. In other words, the phrase "based on" describes both "based only on" and "based at least on."

As used herein, the terms "generally" and "substantially" are intended to encompass structural or numeral modification which do not significantly affect the purpose of the element or number modified by such term.

To aid the Patent Office and any readers of this application and any resulting patent in interpreting the claims appended herein, applicants do not intend any of the appended claims or claim elements to invoke 35 U.S.C. 112(f) unless the words "means for" or "step for" are explicitly used in the particular claim.

The foregoing previous description of the disclosed implementations is provided to enable any person skilled in the art to make or use the present invention. Various modifications to these implementations will be readily apparent to those skilled in the art, and the generic principles defined herein may be applied to other implementations without departing from the scope of the invention. For example, it will be appreciated that one of ordinary skill in the art will be able to employ a number corresponding alternative and equivalent structural details, such as equivalent ways of fastening, mounting, coupling, or engaging tool components, equivalent mechanisms for producing particular actuation motions, and equivalent mechanisms for delivering electrical energy. Thus, the present invention is not intended to be limited to the implementations shown herein but is to be accorded the widest scope consistent with the principles and novel features disclosed herein.

What is claimed is:

1. A method of assembling a surgical tool, comprising:
   providing a handle having a first end, a second end, and a lead screw and at least one spline extendable between the first and second ends;
   rotating the lead screw in a first direction and thereby translating an elevator layer of a carriage proximally along a longitudinal axis of the handle, wherein the elevator layer is movably mounted to the lead screw at a carriage nut;
   removably coupling one or more additional layers of the carriage to the elevator layer, the one or more additional layers including one or more activating mechanisms operable to control the surgical tool, wherein an elongate shaft extends distally from the one or more additional layers and an end effector is arranged at a distal end of the elongate shaft;
   penetrating the elevator layer with the end effector and the elongate shaft upon coupling the one or more additional layers to the elevator layer; and
   rotating the lead screw in a second direction opposite the first direction and thereby translating the carriage distally along the longitudinal axis.

2. The method of claim 1, further comprising coupling a cap to the second end.

3. The method of claim 2, wherein coupling the cap to the second end further comprises:
   receiving an end of the at least one spline in at least one spline coupling provided on the cap upon coupling the cap to the second end; and
   receiving an end of the lead screw in a stage coupling provided on the cap upon coupling the cap to the second end.

4. The method of claim 1, wherein a drive gear and an activating mechanism are housed in the carriage and operatively coupled together such that rotation of the drive gear correspondingly actuates the activating mechanism, the method further comprising:
   inserting the at least one spline through the drive gear and thereby operatively coupling the drive gear to the at least one spline such that the drive gear is rotatable with rotation of the at least one spline.

5. The method of claim 4, further comprising:
   rotating the at least one spline by actuating a drive input arranged at the first end and operatively coupled to the at least one spline to thereby rotate the drive gear; and
   actuating the activating mechanism as the drive gear rotates.

6. The method of claim 5, further comprising:
   mating an instrument driver with the handle at the first end, the instrument driver being arranged at an end of a robotic arm;
   mating a drive output of the instrument driver with the drive input as the instrument driver is mated to the handle; and
   actuating the drive output to rotate the drive input and thereby actuate the activating mechanism.

7. The method of claim 6, wherein mating the instrument driver with the handle at the first end comprises inserting the shaft and the end effector through a central aperture defined longitudinally through the instrument driver.

8. The method of claim 1, further comprising advancing at least a portion of the elevator layer past the second end before removably coupling the one or more additional layers of the carriage to the elevator layer.

9. The method of claim 1, further comprising penetrating the first end with the end effector and the shaft as the carriage translates distally.

10. The method of claim 1, further comprising removing a cap from the second end to expose a floor of the elevator layer before removably coupling the one or more additional layers of the carriage to the elevator layer.

11. The method of claim 1, wherein one or more snaps extend from the one or more additional layers for engaging corresponding opening in the elevator layer, the method further comprising inserting the one or more snaps of the one or more additional layers into the corresponding openings in the elevator layer and thereby securing the one or more additional layers on the elevator floor.

12. The method of claim 11, further comprising retaining the one or more snaps of the one or more additional layers into the corresponding openings in the elevator layer as the carriage distally translates.

13. The method of claim 12, wherein the handle includes a shroud within which the carriage translates, the method further comprising advancing the elevator layer such that the elevator floor and the corresponding openings extend outside of the shroud before removably coupling the one or more additional layers of the carriage to the elevator layer.

14. The method of claim 13, further comprising:
    securing the one or more snaps of the one or more additional layers within the corresponding openings in the elevator layer as the carriage pulls the one or more snaps and corresponding openings into the shroud.

15. The method of claim 1, further comprising detaching the one or more additional layers from the elevator layer and thereby removing the one or more additional layers, the elongate shaft, and the end effector from the handle.

16. The method of claim 15, wherein the one or more additional layers comprise one or more first additional layers, the one or more activating mechanisms comprise one or more first activating mechanisms, the elongate shaft comprises a first elongate shaft, and the end effector comprises a first end effector, the method further comprising:
    removably coupling one or more second additional layers of the carriage to the elevator layer, the one or more second additional layers including one or more second activating mechanisms operable to control the surgical tool, wherein a second elongate shaft extends distally from the one or more second additional layers and a second end effector is arranged at a distal end of the second elongate shaft; and
    penetrating the elevator layer with the second end effector and the second elongate shaft upon coupling the one or more second additional layers to the elevator layer.

* * * * *